(12) United States Patent
Sakamoto et al.

(10) Patent No.: US 7,579,186 B1
(45) Date of Patent: Aug. 25, 2009

(54) HUMAN MONOCLONAL ANTIBODY AGAINST TGF-β TYPE II RECEPTOR AND MEDICINAL USE THEREOF

(75) Inventors: Shinji Sakamoto, Kanagawa (JP); Masafumi Kamada, Kanagawa (JP)

(73) Assignee: Amgen Fremont Inc., South San Francisco, CA (US)

( * ) Notice: Subject to any disclaimer, the term of this patent is extended or adjusted under 35 U.S.C. 154(b) by 364 days.

(21) Appl. No.: 10/130,034

(22) PCT Filed: Nov. 17, 2000

(86) PCT No.: PCT/JP00/08129

§ 371 (c)(1),
(2), (4) Date: Aug. 23, 2002

(87) PCT Pub. No.: WO01/36642

PCT Pub. Date: May 25, 2001

(30) Foreign Application Priority Data

Nov. 18, 1999 (JP) ................................ 11-328681
Nov. 8, 2000 (JP) .............................. 2000-340216

(51) Int. Cl.
*C12N 5/06* (2006.01)
*C07K 16/28* (2006.01)
(52) U.S. Cl. ............... 435/325; 530/388.1; 530/388.15; 530/388.22
(58) Field of Classification Search .............. 424/143.1, 424/142.1, 93.21; 530/388.1, 387.1, 350, 530/402; 435/7.1; 514/411, 44
See application file for complete search history.

(56) References Cited

U.S. PATENT DOCUMENTS

| | | | | |
|---|---|---|---|---|
| 5,147,798 A | * | 9/1992 | Lampkin et al. | ............ 435/372 |
| 5,693,607 A | * | 12/1997 | Segarini et al. | ................ 514/2 |
| 5,824,655 A | * | 10/1998 | Border | ......................... 514/44 |
| 6,037,139 A | * | 3/2000 | Greenspan et al. | ............ 435/23 |
| 6,096,878 A | | 8/2000 | Honjo et al. | ............. 536/23.53 |
| 6,201,108 B1 | | 3/2001 | Lin et al. | ............... 530/388.22 |

FOREIGN PATENT DOCUMENTS

WO WO 91/10741 7/1991
WO WO 94/26895 11/1994
WO WO 01/66140 9/2001

OTHER PUBLICATIONS

Muda, A. et al. Nephrol. Dial. Transplant. (1998), vol. 13, pp. 279-284.*
Alberts et al. Molecular Biology of the Cell, 1989, pp. 1013-1014.*
Hall et al. Biochem. J. 1996, vol. 316, pp. 303-310.*
Peters et al., Kidney Int. 1998 54(5), pp. 1570-1580.*
Herrera, G. Kidney Internat. 40:509-513, 1991 'C-erb B-2 amplification in cystic renal disease'.*
Cao, Y. et al. "TGF-β1 Mediates 70-kDa Heat Shock Protein Induction due to Ultraviolet Irradiation in Human Skin Fibroblasts" *Eur. J. Physiol.* 438:239-44 (1999).
Lagadec, P. et al. "Evidence for Control of Nitric Oxide Synthesis by Intracellular Transforming Growth Factor-β1 in Tumor Cells" *Amer. J. Path.* 154:1867-76 (1999).
Kasuga, H. et al. "Effects of Anti-TGF-beta Type II Receptor Antibody on Experimental Glomerulonephritis" *Kidney Int.* 60:1745-55 (2001).
European Search Report for EP 00976330, dated Jun. 4, 2004.
Rudikoff et al. "Single amino acid substitution altering antigen-binding specificity." *Proc. Natl. Acad. Sci. USA* 79:1979-1983 (1982).
Border et al., "Suppression of experimental glomerulonephritis by antiserum against transforming growth factor beta1," *Nature* 346:371-374 (Jul. 26, 1990).
Brown et al., "Antibodies to the Type II TGF Beta Receptor Block Cell Activation and Migration during Atrioventricular Cushion Transformation in the Heart," *Developmental Biology* 174:248-257 (1996).
Fortunel et al., "Release from Quiescence of Primitive Human Hematopoietic Stem-Progenitor Cells by Blocking Their Surface TGF-Beta Type II Receptor in a Short-Term In Vitro Assay" *Stem Cells*, 18:102-111 (2000).
Meikle et al., "Transforming Growth Factor Beta-1 and Beta-2 and Type II Receptor Functional Regulation of ALVA-101 Human Prostate Cancer Cells," *Metabolism*, 48(9):1075-1081 (1999).
Moustakas et al., "The Transforming Growth Factor Beta Receptors Types I, II and III Form Hetero-oligomeric Complexes in the Presence of Ligand," *J. Biol. Chem.*, 268(30):22215-22218 (1993).
George, et al., "In vivo inhibition of rat stellate cell activation by soluble transforming growth factor β type II receptor: A potential new therapy for hepatic fibrosis", *PNAS*, (Oct. 26, 1999) 96(22):12719-12724.

* cited by examiner

*Primary Examiner*—Marianne P Allen
(74) *Attorney, Agent, or Firm*—Knobbe Martens Olson & Bear LLP

(57) ABSTRACT

Various human monoclonal antibodies that bind to human TGF-β type II receptor to inhibit the signal transduction of human TGF-β signal into cells are produced by immunizing human antibody-producing transgenic mice generated by genetic engineering techniques with the soluble human TGF-β type II receptor. Further, these human monoclonal antibodies were demonstrated to be effective for preventing and treating various diseases induced by human TGF-β in various organs (for example, tissue fibrosis).

29 Claims, 17 Drawing Sheets

Figure 4

| Clone name of anti-TβRII human monoclonal antibody | Isotype | Inhibitory activity on cell-growth induced by TGF-β | Inhibitory activity on cell-growth suppression induced by TGF-β | Inhibitory activity on fibronectin production induced by TGF-β | Inhibitory activity on CTGF production induced by TGF-β |
|---|---|---|---|---|---|
| TR2B19 | Human IgG2/κ | ○ | | ○ | ○ |
| TR2B64 | Human IgG2/κ | ○ | | ○ | ○ |
| TR2B209 | Human IgG2/κ | ○ | | ○ | ○ |
| TR2B518 | Human IgG2/κ | ○ | | ○ | ○ |
| TR2D245 | Human IgG2/κ | ○ | | ○ | ○ |
| TR4B16 | Human IgG4/κ | ○ | ○ | | |
| TR4C175 | Human IgG4/κ | ○ | ○ | | |
| TR4D204 | Human IgG4/κ | ○ | ○ | | |
| TR4D455 | Human IgG4/κ | ○ | ○ | | |
| TR4D465 | Human IgG4/κ | ○ | ○ | | |

SEQUENCE LISTING

```
<160> NUMBER OF SEQ ID NOS: 25

<210> SEQ ID NO 1
<211> LENGTH: 787
<212> TYPE: DNA
<213> ORGANISM: Homo sapiens
<220> FEATURE:
<221> NAME/KEY: misc_feature
<222> LOCATION: 145, 202, 205, 219, 222, 282, 313, 315, 377, 445, 468,
      475, 713, 763, 776, 784
<223> OTHER INFORMATION: n = A,T,C or G

<400> SEQUENCE: 1
atgggtcggg ggctgctcag gggcctgtgg ccgctgcaca tcgtcctgmt gyarggyuua      60
rggyutrruh svautggacg cgtatcgcca gcacgatccc accgcacgtt cagaagtcgg     120
tttrthrarg aasrthrrrh svagnyssrv aaataacgac atgatagtca ctgacaacaa     180
```

-continued

```
cggtgcagtc aagtttccaa snasnasmtv athrasasna sngyaavays hrcaactgtg    240
taaattttgt gatgtgagat tttccacctg tgacaaccag gnucysyshc ysasvaargh    300
srthrcysas asngnaaatc ctgcatgagc aactgcagca tcacctccat ctgtgagaag    360
ccayssrcys mtsrasncys srthrsrcys guysrcagga agtctgtgtg gctgtatgga    420
gaaagaatga cgagaacata acagnguvac ysvaaavatr argysasnas guasnthrct    480
agagacagtt tgccatgacc ccaagctccc ctaccatgac tttattugut hrvacyshsa    540
srysurtyrh sashctggaa gatgctgctt ctccaaagtg cattatgaag gaaaaaaaaa    600
aguguasaaa asrryscysm tysguysysy scctggtgag actttcttca tgtgttcctg    660
tagctctgat gagtgcaatr gyguthrhhm tcyssrcyss rsrasgucys asngacaaca    720
tcatcttctc agaagaatat aacaccagca atcctgacas asnhsrgugu tyrasnthrs    780 rasnras                                                              787
```

<210> SEQ ID NO 2
<211> LENGTH: 159
<212> TYPE: PRT
<213> ORGANISM: Homo sapiens

<400> SEQUENCE: 2

```
Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp
145                 150                 155
```

<210> SEQ ID NO 3
<211> LENGTH: 759
<212> TYPE: DNA
<213> ORGANISM: Homo sapiens
<220> FEATURE:
<221> NAME/KEY: misc_feature
<222> LOCATION: 126, 135, 291, 300, 465, 472, 529, 534, 636
<223> OTHER INFORMATION: n = A,T,C or G

<400> SEQUENCE: 3

```
atggaactgg ggctccgctg ggttttcctt gttgctattt tagaaggtmt guugyuargt     60
rvahuvaaau gugygtccag tgtgaggtgc agctggtgga gtctggggga ggcctggtca    120
agvagncysg uvagnuvagu srgygygyuv ayscctgggg ggtccctgag actctcctgt    180
```

-continued

```
gcagcctctg gattcacctt crgygysrua rgusrcysaa aasrgyhthr hagtagcttt    240
agcatgaact gggtccgcca ggctccaggg aaggggctgs rsrhsrmtas ntrvaarggn    300
aargyysgyu gagtgggtct catccattag tagtagtagt agttacatat actacacagu    360
trvasrsrsr srsrsrsrty rtyrtyrthr gactcagtga agggccgatt caccatctcc    420
agagacaacg ccaagaacas srvaysgyar ghthrsrarg asasnaaysa sntcactgta    480
tctgcaaatg aacagcctga gagccgagga cacggctgtg srutyrugnm tasnsruarg    540
aaguasthra avatattact gtgcgagagg gtactggggg tttgactact ggggccaggg    600
atyrtyrcys aaarggytyr trgyhastyr trgygngyac cctggtcacc gtctcctcag    660
cttccaccaa gggcccatcc gtcttcthru vathrvasrs raasrthrys gyrsrvahcc    720
cctggcgccc tgctccagga gcacruaarc yssrargsr                           759
```

<210> SEQ ID NO 4
<211> LENGTH: 152
<212> TYPE: PRT
<213> ORGANISM: Homo sapiens

<400> SEQUENCE: 4

```
Met Glu Leu Gly Leu Arg Trp Val Phe Leu Val Ala Ile Leu Glu Gly
 1               5                  10                  15

Val Gln Cys Glu Val Gln Leu Val Glu Ser Gly Gly Gly Leu Val Lys
            20                  25                  30

Pro Gly Gly Ser Leu Arg Leu Ser Cys Ala Ala Ser Gly Phe Thr Phe
        35                  40                  45

Ser Ser Phe Ser Met Asn Trp Val Arg Gln Ala Pro Gly Lys Gly Leu
    50                  55                  60

Glu Trp Val Ser Ser Ile Ser Ser Ser Ser Ser Tyr Ile Tyr Tyr Thr
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Gly Tyr Trp Gly Phe Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Cys Ser Arg Ser
145                 150
```

<210> SEQ ID NO 5
<211> LENGTH: 669
<212> TYPE: DNA
<213> ORGANISM: Homo sapiens
<220> FEATURE:
<221> NAME/KEY: misc_feature
<222> LOCATION: 58, 77, 225, 307, 392, 399, 457, 462, 630
<223> OTHER INFORMATION: n = A,T,C or G

<400> SEQUENCE: 5

```
tgccgagtgc agtgtggagt ctgggggagc gtcgtccagc ctgggaagcy sargvagncy     60
sgyvatrgys rvavagnrgy ystccctgag actctcctgt gcagcgtctg gattcacctt    120
cagtagctat sruargusrc ysaaaasrgy hthrhsrsrt yrggcatgca ctgggtccgc    180
caggctccag gcaaggggct ggagtgggtg gymthstrva arggnaargy ysgyugutrv    240
agcagttata tggtatgatg gaagtaataa atactatgca gactccgtga avatrtyras    300
```

| | | | | | |
|---|---|---|---|---|---|
| gysrasnyst | yrtyraaaass | rvaaagggcc | gattcaccat | ctccagagac | aattccaaga | 360 |
| acacgctgta | tysgyarght | hrsrargasa | snsrysasnt | hrutyrctgc | aaatgaacag | 420 |
| cctgagagcc | gaggacacgg | ctgtgtatta | ctgtugnmta | snsruargaa | guasthraav | 480 |
| atyrtyrcys | gcgagagggg | gtatagcagt | ggcgtctgga | ctctactact | accgtatgaa | 540 |
| arggygyaav | aaasrgyuty | rtyrtyrarg | mtgacgtctg | gggccaagga | ccacggtcca | 600 |
| ccttctcctc | agcttccacc | asvatrgygn | gyrargsrth | rhsrsraasr | thraagggcc | 660 |
| catcysgyr | | | | | | 669 |

<210> SEQ ID NO 6
<211> LENGTH: 131
<212> TYPE: PRT
<213> ORGANISM: Homo sapiens

<400> SEQUENCE: 6

Cys Arg Val Gln Cys Gly Val Trp Gly Ser Val Val Gln Pro Gly Lys
 1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ile Ala Val Ala Ser Gly Leu Tyr Tyr Tyr Arg Met
            100                 105                 110

Asp Val Trp Gly Gln Gly Pro Arg Ser Thr Phe Ser Ser Ala Ser Thr
        115                 120                 125

Lys Gly Pro
    130

<210> SEQ ID NO 7
<211> LENGTH: 722
<212> TYPE: DNA
<213> ORGANISM: Homo sapiens
<220> FEATURE:
<221> NAME/KEY: misc_feature
<222> LOCATION: 72, 135, 140, 300, 443, 447, 523, 685, 690
<223> OTHER INFORMATION: n = A,T,C or G

<400> SEQUENCE: 7

| | | | | | |
|---|---|---|---|---|---|
| atggggtcaa | ccgccatcct | cgccctcctc | ctggctgttc | tccaaggamt | gysrthraau | 60 |
| aauuuaavau | gngygtctgt | gccgaggtgc | agctggtgca | gtctggagca | gaggtgaaaa | 120 |
| agvacysaag | uvagnuvagn | srgyaaguva | ysysccccggg | gagtctctga | agatctcctg | 180 |
| taagggttct | ggatacagct | ttrgygusru | yssrcysysg | ysrgytyrsr | haccagctac | 240 |
| tggatcggct | gggtgcgcca | gatgcccggg | aaaggcctgt | hrsrtyrtrg | ytrvaarggn | 300 |
| mtrgyysgyu | gagtggatgg | ggatcatcta | tcctggtgac | tctgatacca | gatacagcgu | 360 |
| trmtgytyrr | gyassrasth | rargtyrsrc | cgtccttcca | aggccaggtc | accatctcag | 420 |
| ccgacaagtc | catcagcrsr | hgngygnvat | hrsraaasys | srsraccgcc | tacctgcagt | 480 |
| ggagcagcct | gaaggcctcg | gacaccgcca | tgthraatyr | ugntrsrsru | ysaasrasth | 540 |

```
raamttatta ctgtgcgagg gtgggggggt gtagtggtgg tagctgctac ctctyrtyrc    600
ysaaargvag ygycyssrgy gysrcystyr utggggccag ggaaacctgg tcaccgtctc    660
ctcagcttcc accaagggct rgygngyasn uvathrvasr sraasrthry sgyccatccr    720 sr                                                                  722

<210> SEQ ID NO 8
<211> LENGTH: 146
<212> TYPE: PRT
<213> ORGANISM: Homo sapiens

<400> SEQUENCE: 8

Met Gly Ser Thr Ala Ile Leu Ala Leu Leu Ala Val Leu Gln Gly
 1               5                  10                  15

Val Cys Ala Glu Val Gln Leu Val Gln Ser Gly Ala Glu Val Lys Lys
             20                  25                  30

Pro Gly Glu Ser Leu Lys Ile Ser Cys Lys Gly Ser Gly Tyr Ser Phe
         35                  40                  45

Thr Ser Tyr Trp Ile Gly Trp Val Arg Gln Met Pro Gly Lys Gly Leu
     50                  55                  60

Glu Trp Met Gly Ile Ile Tyr Pro Gly Asp Ser Asp Thr Arg Tyr Ser
 65                  70                  75                  80

Pro Ser Phe Gln Gly Gln Val Thr Ile Ser Ala Asp Lys Ser Ile Ser
                 85                  90                  95

Thr Ala Tyr Leu Gln Trp Ser Ser Leu Lys Ala Ser Asp Thr Ala Met
            100                 105                 110

Tyr Tyr Cys Ala Arg Val Gly Gly Cys Ser Gly Gly Ser Cys Tyr Leu
        115                 120                 125

Trp Gly Gln Gly Asn Leu Val Thr Val Ser Ser Ala Ser Thr Lys Gly
    130                 135                 140

Pro Ser
145

<210> SEQ ID NO 9
<211> LENGTH: 750
<212> TYPE: DNA
<213> ORGANISM: Homo sapiens
<220> FEATURE:
<221> NAME/KEY: misc_feature
<222> LOCATION: 127, 132, 136, 155, 304, 386, 471, 478, 536, 541
<223> OTHER INFORMATION: n = A,T,C or G

<400> SEQUENCE: 9
atggagtttg gctgagctg gttttcctc gttgctcttt taagaggtmt guhgyusrtr     60
vahuvaaauu arggygtcca gtgtcaggtg cagctggtgg agtctggggg aggcgtggtc   120
cagvagncys gnvagnuvag usrgygygyv avagncctgg gaggtccctg agactctcct  180
gtgcagcgtc tggattcacc ttcrgyargs ruargusrcy saaaasrgyh thrhagtagc  240
tatggcatgc actgggtccg ccaggctcca ggcaaggggc tgsrsrtyrg ymthstrvaa  300
rggnaargyy sgyugagtgg gtggcagtta tatggtatga tggaagtaat aaatactatg  360
cagutrvaaa vatrtyrasg ysrasnysty rtyraagact ccgtgaaggg ccgattcacc  420
atctccagag acaattccaa gaacassrva ysgyarghth rsrargasas nsrysasnac  480
gctgtatctg caaatgaaca gcctgagagc cgaggacacg gctgtgthru tyrugnmtas  540
nsruargaag uasthraava tattactgtg cgagagaggg gatgactacg gtgaccccta  600
```

```
ctactacgty rtyrcysaaa rggugymtth rthrvathrr thrthrthrg tatgqacgtc    660 tggggccaag gaccacggtc accgtctcct cacttccvat rthrsrgyaa ysashsgyhs    720
arguuthrsr accaagggcc cgthrysgyr                                    750
```

<210> SEQ ID NO 10
<211> LENGTH: 148
<212> TYPE: PRT
<213> ORGANISM: Homo sapiens

<400> SEQUENCE: 10

```
Met Glu Phe Gly Leu Ser Trp Val Phe Leu Val Ala Leu Leu Arg Gly
 1               5                  10                  15
Val Gln Cys Gln Val Gln Leu Val Glu Ser Gly Gly Gly Val Val Gln
            20                  25                  30
Pro Gly Arg Ser Leu Arg Leu Ser Cys Ala Ala Ser Gly Phe Thr Phe
        35                  40                  45
Ser Ser Tyr Gly Met His Trp Val Arg Gln Ala Pro Gly Lys Gly Leu
    50                  55                  60
Glu Trp Val Ala Val Ile Trp Tyr Asp Gly Ser Asn Lys Tyr Tyr Ala
65                  70                  75                  80
Asp Ser Val Lys Gly Arg Phe Thr Ile Ser Arg Asp Asn Ser Lys Asn
                85                  90                  95
Thr Leu Tyr Leu Gln Met Asn Ser Leu Arg Ala Glu Asp Thr Ala Val
            100                 105                 110
Tyr Tyr Cys Ala Arg Glu Gly Met Thr Thr Val Thr Pro Thr Thr Thr
        115                 120                 125
Val Trp Thr Ser Gly Ala Lys Asp His Gly His Arg Leu Leu Thr Ser
    130                 135                 140
Thr Lys Gly Pro
145
```

<210> SEQ ID NO 11
<211> LENGTH: 712
<212> TYPE: DNA
<213> ORGANISM: Homo sapiens
<220> FEATURE:
<221> NAME/KEY: misc_feature
<222> LOCATION: 64, 138, 145, 284, 292, 304, 306, 384, 525, 548, 601,
      606, 712
<223> OTHER INFORMATION: n = A,T,C or G

<400> SEQUENCE: 11

```
atggacatga gggtccccgc tcagctcctg ggctcctgc tgctctggmt asmtargvar    60
aagnuugyuu uutrttccca ggtgccaggt gtgacatcca gatgacccag tctccatcct   120
cchrgyaaar gcysasgnmt thrgnsrrsr srctgtctgc atctgtagga cagagtca     180 ccatcacttg ccgggcaagt usraasrvag yasargvath rthrcysarg aasrcagggc   240
attagaaatg atttaggctg gtatcagcag aaaccaggga agngyarga snasugytrt    300 yrgngnysrg yysgcccta agcgcctgat ctatgctgca tccagtttgc aaagtggggt    360
caarysargu tyraaaasrs rugnsrgyva ccatcaaggt tcagcggcag tgcatctggg   420
acagaattca ctctcacars rarghsrgys raasrgythr guhthruthr atcagcagcc   480
tgcagcctga agattttgca acttattact gtctacagsr srugnrguas haathrtyrt   540
yrcysugnca taatagtaac ccgctcactt tcggcggagg gaccaaggtg gagatchsas   600
nsrasnruth rhgygygyth rysvaguaaa cgaactgtgg ctgcaccatc tgtcttcatc   660
```

```
ttcccgccat ctgatysarg thrvaaaaar srvahhrrsr asgagcaggu gn          712
```

<210> SEQ ID NO 12
<211> LENGTH: 146
<212> TYPE: PRT
<213> ORGANISM: Homo sapiens

<400> SEQUENCE: 12

```
Met Asp Met Arg Val Pro Ala Gln Leu Leu Gly Leu Leu Leu Leu Trp
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asp Leu Gly Trp Tyr Gln Gln Lys Pro Gly Lys
    50                  55                  60

Ala Pro Lys Arg Leu Ile Tyr Ala Ala Ser Ser Leu Gln Ser Gly Val
65                  70                  75                  80

Pro Ser Arg Phe Ser Gly Ser Ala Ser Gly Thr Glu Phe Thr Leu Thr
                85                  90                  95

Ile Ser Ser Leu Gln Pro Glu Asp Phe Ala Thr Tyr Tyr Cys Leu Gln
            100                 105                 110

His Asn Ser Asn Pro Leu Thr Phe Gly Gly Gly Thr Lys Val Glu Ile
        115                 120                 125

Lys Arg Thr Val Ala Ala Pro Ser Val Phe Ile Phe Pro Pro Ser Asp
    130                 135                 140

Glu Gln
145
```

<210> SEQ ID NO 13
<211> LENGTH: 654
<212> TYPE: DNA
<213> ORGANISM: Homo sapiens
<220> FEATURE:
<221> NAME/KEY: misc_feature
<222> LOCATION: 55, 60, 143, 292, 295, 300, 313, 315, 319, 544, 553, 555
<223> OTHER INFORMATION: n = A,T,C or G

<400> SEQUENCE: 13

```
atggtgttgc agacccagtc ttcattctct gttgctctgg atctctggmt vaugnthrgn   60
srsrhsrvaa auasutrtgc ctacgggaca tcgtgatgac ccagtctcca gactccctgg  120
ctgtgcysua rgasvamtth rgnsrrassr uaavatctct gggcgagagg ccaccatcaa  180
ctgcaagtcc agccagagtg ttasrugygu argrrsrthr aasrraaarg vautacaggt  240
ccaacaataa gaactactta gcttggtacc agcagaaaca gtyrargsra snasnysasn  300
tyruaatrty rgngnysgng acagcctcct aagctgctca ttactggcat ctacccggaa  360
gccgggtass ruusrcyssr uuaasrthra rgysrgycct gaccgattca gtggcagcgg  420
gtctgggaca gattcactct caccarasar ghsrgysrgy srgythrass rusrrtcagc  480
cgcctgcagg ctgatgatgt ggcagttata ctgtcagcaa tgtsraaaac ysargumtmt  540
trgnutyrcy sgngncysta tagtgctcct gtcacttcgg cggaggacag tgacatcaaa  600
cgaacttyrs raarvathrs raaguassra sysargthrg tggctgcava aaaa         654
```

<210> SEQ ID NO 14
<211> LENGTH: 131
<212> TYPE: PRT
<213> ORGANISM: Homo sapiens

<400> SEQUENCE: 14

Met Val Leu Gln Thr Gln Ser Ser Phe Ser Val Ala Leu Asp Leu Trp
1               5                   10                  15

Cys Leu Arg Asp Ile Val Met Thr Gln Ser Pro Asp Ser Leu Ala Val
            20                  25                  30

Ser Leu Gly Glu Arg Pro Pro Ser Thr Ala Ser Pro Ala Arg Val Leu
        35                  40                  45

Tyr Arg Ser Asn Asn Lys Asn Tyr Leu Ala Trp Tyr Gln Gln Lys Gln
    50                  55                  60

Asp Ser Leu Leu Ser Cys Ser Leu Leu Ala Ser Thr Arg Lys Pro Gly
65                  70                  75                  80

Pro Asp Arg Phe Ser Gly Ser Gly Ser Gly Thr Asp Ser Leu Ser Pro
                85                  90                  95

Ser Ala Ala Cys Arg Leu Met Met Trp Gln Leu Tyr Cys Gln Gln Cys
            100                 105                 110

Tyr Ser Ala Pro Val Thr Ser Ala Glu Asp Ser Asp Ile Lys Arg Thr
        115                 120                 125

Val Ala Ala
    130

<210> SEQ ID NO 15
<211> LENGTH: 674
<212> TYPE: DNA
<213> ORGANISM: Homo sapiens
<220> FEATURE:
<221> NAME/KEY: misc_feature
<222> LOCATION: 59, 143, 228, 287, 295, 309, 364, 369, 380, 598, 613
<223> OTHER INFORMATION: n = A,T,C or G

<400> SEQUENCE: 15
atgaggctcc ctgctcagct cctggggctg ctaatgctct gggtctctmt arguraagnu     60
ugyuumtutr vasrggatcc agtggggatg ttgtgatgac tcagtctcca ctctccctgc    120
ccgysrsrgy asvavamtth rgnsrrusru rgtcacccct ggagagccgg cctccatctc    180
ctgcaggtct agtcagagcv athrrgygur aasrsrcysa rgsrsrgnsr ctcctgcata    240
gtaatggata caactatttg gattggtacc tgcagaaguu hsssrasngyt yrasntyrua    300 strtyrugny sccagggcag tctccacagc tcctgatctt tttgggttct aatcgggccr    360
gygnsrrgnu uhugysrasn argaatccgg ggtccctgac aggttcagtg gcagtggatc    420
aggcacagat tttsrgyvar asarghsrgy srgysrgyth rashacactg aaaatcagca    480
gagtggaagc tgaagatgtt ggggtttatt tcthruyssr argvaguaag uasvagyvat    540
yrhtgcatgc aagttttacc acttcctccg accttcggcc aagggacacg acysmtgnva    600
ururrthrhg ygngythrar gctggagatt aaacgaactg tggctgcacc atctuguysa    660
rgthrvaaaa arsr                                                     674

<210> SEQ ID NO 16
<211> LENGTH: 139
<212> TYPE: PRT
<213> ORGANISM: Homo sapiens

<400> SEQUENCE: 16

Met Arg Leu Pro Ala Gln Leu Leu Gly Leu Leu Met Leu Trp Val Ser
1               5                   10                  15

Gly Ser Ser Gly Asp Val Val Met Thr Gln Ser Pro Leu Ser Leu Pro
            20                  25                  30

```
Val Thr Pro Gly Glu Pro Ala Ser Ile Ser Cys Arg Ser Ser Gln Ser
            35                  40                  45

Leu Leu His Ser Asn Gly Tyr Asn Tyr Leu Asp Trp Tyr Leu Gln Lys
     50                  55                  60

Pro Gly Gln Ser Pro Gln Leu Leu Ile Phe Leu Gly Ser Asn Arg Ala
 65                  70                  75                  80

Ser Gly Val Pro Asp Arg Phe Ser Gly Ser Gly Ser Gly Thr Asp Phe
                 85                  90                  95

Thr Leu Lys Ile Ser Arg Val Glu Ala Glu Asp Val Gly Val Tyr Phe
            100                 105                 110

Cys Met Gln Val Leu Pro Leu Pro Pro Thr Phe Gly Gln Gly Thr Arg
            115                 120                 125

Leu Glu Ile Lys Arg Thr Val Ala Ala Pro Ser
            130                 135
```

<210> SEQ ID NO 17
<211> LENGTH: 654
<212> TYPE: DNA
<213> ORGANISM: Homo sapiens
<220> FEATURE:
<221> NAME/KEY: misc_feature
<222> LOCATION: 141, 210, 309, 316, 383, 395, 457, 552, 620
<223> OTHER INFORMATION: n = A,T,C or G

<400> SEQUENCE: 17

```
atgaggctct gctcagctct ggctgctatg tctggatacc tgtccagtmt argucyssra      60
auaaaamtsr gytyrusrsr gcagatattg tgatgaccca gactcactct ctctgtcgtc     120
accctggaaa asvamtthrg nthrhssruc ysarghsrgy cagacggctc catctcctgc     180
aagtctagtc agagcctctt gcttggtggn thraarsrra asruvaarga asrcysuvaa     240
tggaagacta tatgtattgg tacctgcaga agccaggcca gcctccamtg uastyrmtty     300
rtrtyrugny srgygnrrca cctcctgatg tatgcagttc caaccggtt tctggagtgc     360
cagatahsuu mttyraavar asnarghugu cysgnggttc agtggcagcg ggtcaggaca     420
gattcacact gaaaatcagc cgggysrvaa aaagygnasa rghthruyss rarggtggag     480
gctgaaggat gttggcatta ttactgcatg caagtataca gcvaguaagu gycystrhst     540
yrtyrcysmt gnvatyrsrt ctcggacgtt cggccagggg tccagtggaa tcaaacgaac     600
tgtggctsra rgthrhgygn gysrsrgyys argthrvaaa gcaccatcta arsr           654
```

<210> SEQ ID NO 18
<211> LENGTH: 131
<212> TYPE: PRT
<213> ORGANISM: Homo sapiens

<400> SEQUENCE: 18

```
Met Arg Leu Cys Ser Ala Leu Ala Ala Met Ser Gly Tyr Leu Ser Ser
 1               5                  10                  15

Ala Asp Ile Val Met Thr Gln Thr His Ser Leu Cys Arg His Pro Gly
             20                  25                  30

Gln Thr Ala Pro Ser Pro Ala Ser Leu Val Arg Ala Ser Cys Leu Val
         35                  40                  45

Met Glu Asp Tyr Met Tyr Trp Tyr Leu Gln Lys Pro Gly Gln Pro Pro
     50                  55                  60

His Leu Leu Met Tyr Ala Val Pro Asn Arg Phe Leu Glu Cys Gln Ile
 65                  70                  75                  80
```

```
Gly Ser Val Ala Ala Gly Gln Asp Arg Phe Thr Leu Lys Ile Ser Arg
                85                  90                  95

Val Glu Ala Glu Gly Cys Trp His Tyr Tyr Cys Met Gln Val Tyr Ser
            100                 105                 110

Ser Arg Thr Phe Gly Gln Gly Ser Ser Gly Ile Lys Thr Val Ala
        115                 120                 125

Ala Pro Ser
    130

<210> SEQ ID NO 19
<211> LENGTH: 45
<212> TYPE: DNA
<213> ORGANISM: Artificial Sequence
<220> FEATURE:
<223> OTHER INFORMATION: Artificially synthesized primer sequence

<400> SEQUENCE: 19
aactggaagc ttcagcggcc gcagagattt ttttttttt ttttt              45

<210> SEQ ID NO 20
<211> LENGTH: 14
<212> TYPE: DNA
<213> ORGANISM: Artificial Sequence
<220> FEATURE:
<223> OTHER INFORMATION: Artificially synthesized adaptor sequence

<400> SEQUENCE: 20
aattcgcctc gtgg                                               14

<210> SEQ ID NO 21
<211> LENGTH: 10
<212> TYPE: DNA
<213> ORGANISM: Artificial Sequence
<220> FEATURE:
<223> OTHER INFORMATION: Artificially synthesized adaptor sequence

<400> SEQUENCE: 21
ccacgaggcg                                                    10

<210> SEQ ID NO 22
<211> LENGTH: 22
<212> TYPE: DNA
<213> ORGANISM: Artificial Sequence
<220> FEATURE:
<223> OTHER INFORMATION: Artificially synthesized probe sequence

<400> SEQUENCE: 22
tcttgtagtt gttctccggc tg                                      22

<210> SEQ ID NO 23
<211> LENGTH: 23
<212> TYPE: DNA
<213> ORGANISM: Artificial Sequence
<220> FEATURE:
<223> OTHER INFORMATION: Artificially synthesized probe sequence

<400> SEQUENCE: 23
gtctgctttg ctcagcgtca ggg                                     23

<210> SEQ ID NO 24
<211> LENGTH: 21
<212> TYPE: DNA
<213> ORGANISM: Artificial Sequence
<220> FEATURE:
<223> OTHER INFORMATION: Artificially synthesized primer sequence
```

```
<400> SEQUENCE: 24
caccggttcg gggaagtagt c                                                      21

<210> SEQ ID NO 25
<211> LENGTH: 20
<212> TYPE: DNA
<213> ORGANISM: Artificial Sequence
<220> FEATURE:
<223> OTHER INFORMATION: Artificially synthesized primer sequence

<400> SEQUENCE: 25
gttccagatt tcaactgctc                                                        20
```

HUMAN MONOCLONAL ANTIBODY AGAINST TGF-β TYPE II RECEPTOR AND MEDICINAL USE THEREOF

TECHNICAL FIELD

The present invention relates to: human monoclonal antibodies or a portion thereof, which can bind to the type II receptor of human transforming growth factor-β (TGF-β) (hereinafter referred to as "TGF-β type II receptor" or "TβRII"); cells producing the human monoclonal antibodies; pharmaceutical compositions comprising the human monoclonal antibodies; and pharmaceutical compositions comprising substances that bind to the TGF-β type II receptor to inhibit or suppress the signal transduction through the receptor (for example, antibodies or chemically synthesized low-molecular-weight compounds that bind to the TGF-β type II receptor, etc.).

BACKGROUND ART

Two types of factors found during the search of growth factors for fibroblast cells of normal rats as molecules enhancing the transformation of normal cells were given names as transforming growth factor-α (TGF-α) and transforming growth factor-β (TGF-β). Subsequent studies have revealed that TGF-α is a molecule belonging to the epidermal growth factor (EGF) family, whereas TGF-β is produced from almost all types of cells and further the receptor therefor is expressed in a wide variety of organs and cells (Biol. Signals., Vol. 5, p. 232, 1996 and Pulmonary Fibrosis, Vol. 80 of Lung Biology in Health and Disease Series, ed. by Phan et al, p. 627, Dekker, New York, 1995).

TGF-β has the activity to regulate cell differentiation and growth. The cell growth-promoting activity of TGF-β largely depends on the type of cell (Roberts et al, The transforming growth factor-βs, In Peptide Growth Factors and Their Receptors, Part I, ed. by Sporn, M. B. & Roberts, A. B. Springer-Verlag, Berlin, 1990, p. 419-472). For example, it has been clarified that the factor shows cell growth-promoting activity to mesangial cells, such as fibroblast cells and vascular smooth muscle cells, whereas it serves not as a growth-promoting factor but as a growth-suppressing factor on a variety of cells including epithelial cells, vascular endothelial cells, and hemocytes. TGF-β has been further revealed to possess not only cell growth modulating functions but also various functions including immune system regulation; enhancement of the extracellular matrix (ECM) protein accumulation, such as collagen, fibronectin, and tenascin (Adv. Immunol., Vol. 55, p. 181, 1994 and Seminars in Cell Biol., Vol. 5, p. 389, 1994); and so on.

Recently, it has been clarified that the mechanism for the diversified functions of TGF-β depends on the distinctive structure of TGF-β receptors and the signal transduction thereby.

TGF-β is a protein with a molecular weight of about 25-kDa. Two peptide strands form a dimer. Five types of isoforms exist for TGF-β: i.e., TGF-β1, TGF-β2, and TGF-β3 in mammals; TGF-β4 in chicken; and TGF-β5 in frog. These isoforms exhibit a homology of about 70% to one another.

Among these TGF-β species, the function of TGF-β1 has been extensively analyzed. TGF-β1 plays extremely important roles in the process of wound healing in biological tissues (New Engl. J. Med., Vol. 331, p. 1286, 1994 and J. Cell. Biol., Vol. 119, p. 1017, 1992). In the site of tissue wounded, rapid and dynamic biological reactions including infiltration of inflammatory cells and fibroblast cells, production of ECM and vascularization, and cell growth for the subsequent tissue regeneration occur to repair the injured tissue.

First, bleeding starts at the infliction of a wound, and then, TGF-β and PDGF (platelet-derived growth factor) are produced by platelets together with the activation of ECM-bound inactive TGF-β at the wound site. By exposure to a high concentration of thus produced TGF-β, cells migrated to the wound site and cells at the wound site secrete growth factors and cytokines, such as FGF (fibroblast growth factor), TNF (tumor necrosis factor), and IL-1 (interleukin-1); and fibroblast cells also synthesize and secrete ECM.

Further, for example, increased production of platelet-derived growth factor (PDGF), connective tissue growth factor (CTGF; also celled Hcs24) (J. Cell Biology, Vol. 114, No. 6, p. 1285-1294, 1991; Int. J. Biochem. Cell Biol. Vol. 29, No. 1, p. 153-161, 1997; Circulation, Vol. 95, No. 4, p. 831-839, 1997; Cell Growth Differ., Vol. 7, No. 4, p. 469-480, 1996; J. Invest. Dermatol., Vol. 106, No. 4, p. 729-733, 1996; J. Invest. Dermatol., Vol. 105, No. 2, p. 280-284, 1995; J. Invest. Dermatol., Vol. 105, No. 1, p. 128-132, 1995; and international publication WO 96/38172)), and fibronectin are observed in fibroblast cells and mesangial cells.

Further, TGF-β1 is believed to contribute to the wound healing by suppressing the production of proteases and enhancing the production of inhibitors against the enzymes, and further, by enhancing the synthesis of integrins, that participate in the adhesion of ECM to cells, promoting the production and deposition of ECM. In addition, TGF-β also exhibits an immuno-suppressing activity by suppressing the functions of T lymphocytes and B lymphocytes to inhibit the synthesis of TNF and IL-1.

The mechanism for the regulation of TGF-β expression has not been fully clarified, but the expression is expected to be regulated by the binding of TGF-β itself to proteoglycan, i.e. ECM (Nature, Vol. 346, p. 281, 1990 and Nature, Vol. 360, p. 361, 1992). More specifically, it has been believed that, the overexpression of TGF-β is suppressed by a negative regulation by ECM, whose production is enhanced by TGF-β itself, while TGF-β promotes the wound healing. Therefore, abnormalities in the negative regulation may lead to the overexpression of TGF-β, and thus can result in a morbid state, such as tissue fibrosing (fibrosis).

On the other hand, in pulmonary fibrosis and nephrosclerosis, in spite of sufficient deposit of ECM the concentration of TGF-β is retained high and leads to the progress of the morbid states, such as fibrosis (Kidney Int. Vol. 45, p. 916, 1994 and J. Clin. Invest., Vol. 92, p. 632, 1993). The unceasing infliction of tissue injury has been presumed to continuously transduce signals to express TGF-β, suppress the above-mentioned negative regulation signal for TGF-β expression, or cause both events synergistically in pulmonary fibrosis and nephrosclerosis.

Nephrosclerosis is a terminal state of many types of kidney diseases, such as chronic glomerulonephritis and diabetic nephropathy, which is characterized by the proliferation of mesangial cells and the production of ECM. Aberrant expression patterns of TGF-β have been found in kidney of nephrosclerosis patients (J. Clin. Invest., Vol. 90, p. 1, 1992 and Proc. Natl. Acad. Sci. USA, Vol. 86, p. 1056, 1989). Further, in an experimental model for nephritis, which is induced by an anti-Thy-1 antibody, the administration of anti-TGF-β antibody was shown to suppress the progress of nephritis. This suggests that TGF-β participates in the onset of morbid state of nephrosclerosis (Nature, Vol. 346, p. 371, 1990).

On the other hand, TGF-β is expressed at high concentration in lung of subjects with pulmonary fibrosis induced by bleomycin administration or sudden pulmonary fibrosis; suggesting the relation of TGF-α in the onset of pulmonary fibrosis.

Further, expression of TGF-β was detected at collagen-deposited sites in tissues biopsy obtained from chronic hepatitis patients and cirrhosis patients. Furthermore, ECM deposition and TGF-β expression are also reported in vascular restenosis; arthritis, such as rheumatoid arthritis; keloid of skin; and so on.

These findings have suggested the possibility that TGF-β is associated with the onsets of morbid states of various types of tissue fibrosing (fibrosis). Thus, experimental attempts of therapy for tissue fibrosis are made by suppressing the function of TGF-β using antisense pharmaceuticals and gene therapy (Kidney Int., Vol. 50, p. 148, 1996).

Signal transduction into cells through the binding of TGF-β to TGF-β receptor initiates the above-mentioned expression of various functions of TGF-β and the onsets of various morbid states of tissue fibroses due to TGF-β.

Three types of TGF-β receptors have been identified from mammals including human and rat, which structures have been already revealed. The three are: the type I receptor (molecular weight=about 53 kDa; GenBank Accession No: L11695; Cell, Vol. 75, No. 4, p. 681, 1993; hereinafter referred to as "TGF-β type I receptor" or "TβRII"); the type II receptor (molecular weight=about 70 kDa; GenBank Accession No: M85079; Cell, Vol. 68, No. 4, p. 775, 1992; hereinafter referred to as "TGF-β type II receptor" or "TβRI"); and the type III receptor (molecular weight=about 200 to 300 kDa; GenBank Accession No: L07594; Cell, Vol. 67, No. 4, p. 785, 1991; Cell, Vol. 67, No. 4, p. 797, 1991; and Biochem. Biophys. Res. Commun. Vol. 189, No. 1, p. 356, 1992; hereinafter referred to as "TGF-β type III receptor" or "TβRIII") (Adv. Imm., Vol. 55, p. 181, 1994).

The roles of the receptors have been revealed by functional analysis using artificially established TGF-β-resistant variant, derived from mink lung epithelium cell line MvlLu. Among the three receptors, TGF-β type I receptor and TGF-β type II receptor were demonstrated to be important and essential for the signal transduction of TGF-β (J. Biol. Chem., Vol. 265, p. 18518, 1990 and J. Biol. Chem., Vol. 266, p. 9108, 1991). On the other hand, TGF-β type III receptor is not essential for the signal transduction of TGF-β, and plays an indirect role in the transduction.

TGF-β type III receptor is a transmembrane protein consisting of 849 amino acids, which includes an extracellular domain (761 amino acids), transmembrane domain (24 amino acids) and cytoplasmic domain (43 amino acids). The cytoplasmic domain of the TGF-β type III receptor is rich in serine (Ser)/threonine (Thr) residues, which correspond to 40% or more of the total amino acids.

TGF-β type I receptor is a transmembrane protein consisting of 503 amino acids, which includes an extracellular domain (101 amino acids), transmembrane domain (22 amino acids) and cytoplasmic domain (356 amino acids).

Similarly, TGF-β type II receptor is a transmembrane protein consisting of 567 amino acids, which includes a signal sequence (23 amino acids), extracellular domain (136 amino acids), transmembrane domain (30 amino acids), and cytoplasmic domain (378 amino acids).

TGF-β type I and TGF-β type II receptors are single-transmembrane proteins whose extracellular domains are relatively short and which have a serine/threonine kinase structure containing two kinase domains. Further, the cytoplasmic domain contains an aspartic acid (Asp)-linked sugar chain, and the domain of the TGF-β type I receptor and TGF-β type II receptor have 10 cysteine (Cys) residues and 12 Cys residues, respectively, which provide a characteristic protein tertiary structure.

A region rich in glycine (Gly), serine (Ser), and threonine (Thr), dubbed "Gdomain", is observed adjacent to the kinase domain in the cytoplasmic region of a TGF-β type I receptor. The TGF-β type II receptor has a similar structure to that of TGF-β type I receptor but lacks the GS domain.

The kinase domains of TGF-β type I receptor and TGF-β type II receptor have been demonstrated to share a homology of about 43%, and are both protein kinases specific to serine/threonine. Further, reaction of the two serine/threonine kinase domains have been revealed essential for the TGF-β signal transduction into cells (J. Biol. Chem., Vol. 269, p. 30753, 1994).

Both of TGF-β type I receptor and TGF-β type II receptor are essential for the signal transduction of TGF-β into cells. The TGF-β type II receptor can bind to TGF-β by itself, whereas the TGF-β type I receptor cannot bind to TGF-β alone. The formation of a complex of the TGF-β type I and type II receptors on the cell surface is important for the signal transduction of TGF-β into cells.

The binding of TGF-β to a TGF-β type II receptor has been reported to lead to the formation of a hetero-tetramer complex of the TGF-β type II receptor and TGF-β type I receptor on cell surface (J. Biol. Chem., Vol. 269, p. 20172, 1994). Specifically, when the TGF-β type I receptor and the TGF-β type II receptor form a complex in the presence of TGF-β, the TGF-β type I receptor serves as a substrate forTGF-β type II receptor and the GS domain thereof is phosphorylated by the TGF-β type II receptor to activate the TGF-β type I receptor. As a result, other intracellular substrates are phosphorylated and allows a further downstream transduction of the TGF-β signaling (Nature, Vol. 370, p. 341, 1994).

The TGF-β signaling pathway downstream of TGF-β type I receptor has not yet been fully elucidated, but recently, signaling molecules located downstream of the TGF-β type I receptor have been identified: (1) signaling molecules consisting of eight isoforms, collectively called "Smad" (S Mothers against Dpp), mediating the signal transduction of TGF-β (Nature, Vol. 381, p. 620, 1996; Cell, Vol. 86, p. 543, 1996; Nature, 383, p. 168, 1996; and Nature, Vol. 383, p. 832, 1996); and (2) a signaling molecule called TAK1 (TGF-β activated kinase-1) (Science, Vol. 270, p. 2008, 1995). Smad2 and Smad3 have been reported that they bind to the TGF-β type I receptor, which had been activated by forming a complex with the TGF-β type II receptor; are phosphorylated by the kinase domain of the TGF-β type II receptor; are released from the TGF-β type II receptor to form a complex with Smad4 (DPC4); and, then, translocate into the nucleus (Cell, Vol. 87, p. 1215, 1996 and EMBO J., Vol. 16, No. 17, 1997). The Smad2/Smad4 or Smad3/Smad4 complex translocated into the nucleus are suggested to function as a transcription activating factor by binding to a DNA-binding protein (transcription factor), so that gene expression is regulated (Nature, Vol. 383, p. 832, 1996 and Nature, Vol. 390, p. 465, 1997).

TAK1 has been demonstrated to be associated with the signal transduction of TGF-β, functioning as a MAPKKK in the cascade of MAP kinase.

As described above, TGF-β is closely involved in the onsets of nephrosclerosis; various tissue fibroses, such as pulmonary fibrosis and cirrhosis; as well as the onset of various morbid states, such as chronic hepatitis, rheumatoid arthritis, vascular restenosis, and keloid of skin. The onsets of these morbid states may result from TGF-β signal transduction into cells mediated by TGF-β receptor.

Accordingly, this raises the possibility that the morbid states can be treated or prevented by regulating, in particular suppressing, the transduction of TGF-β signal into cells.

An attempt to suppress the morbid states by suppressing TGF-β signal transduction is in practice to treat nephritis, and such, by suppressing the function of TGF-β using antibodies against TGF-β or antisense nucleic acids of the TGF-β gene, in which the TGF-β is a target.

However, treatment of diseases by suppressing functions of TGF-α receptors, particularly TGF-β type II receptor, which is the binding partner of TGF-β, hasn't been reported; in other words, there is no report on therapy for the diseases by inhibiting the signal transduction of TGF-β into cells mediated by the TGF-β type II receptor, in which the TGF-β type II receptor is a target.

Further, no report is published on therapeutic approach for diseases, which approach comprises the inhibition of the signal transduction of TGF-β mediated by TGF-β type II receptor using antibodies against the TGF-β type II receptor.

Polyclonal antibodies derived from non-human mammals, such as rabbit and goat, are the only antibodies reported as antibodies against human TGF-β type II receptor. So far, the preparation of human-derived monoclonal antibodies and attempts of therapy for various diseases using human monoclonal antibody, not to mention monoclonal antibodies against human TGF-β type II receptor have been reported.

DISCLOSURE OF THE INVENTION

TGF-β has been suggested to be closely associated with various diseases and symptoms, for example, the onsets of various tissue fibroses, such as nephrosclerosis, pulmonary fibrosis, and cirrhosis, as well as chronic hepatitis, rheumatoid arthritis, vascular restenosis, keloid of skin, and so on.

Because the function of TGF-β is expressed by the transduction of the TGF-β signal into cells mediated by the binding of the TGF-β to TGF-β type II receptor, it is expected that the morbid states can be treated or prevented by suppressing the signal transduction of TGF-β mediated by the TGF-β type II receptor using a substance that binds to the TGF-β type II receptor, for example, antibodies against the TGF-β type II receptor.

Specifically, an object of the present invention is to provide a monoclonal antibody against human TGF-β type II receptor, particularly human monoclonal antibody against human TGF-β type II receptor, which is extremely useful to treat various diseases described above, such as tissue fibrosis; pharmaceutical composition comprising a substance that binds to the TGF-β type II receptor to suppress or inhibit the signal transduction into cells mediated by the receptor (for example, the above-mentioned monoclonal antibodies against human TGF-β type II receptor, chemically synthesized low-molecular-weight compounds, etc.); and therapeutic methods to treat various diseases thereby (e.g., various kidney diseases (e.g., nephritis, kidney fibrosis, nephrosclerosis, etc.), various tissue fibroses such as kidney fibrosis and pulmonary fibrosis, cirrhosis, rheumatoid arthritis, skin keloid, etc.).

The present inventors strenuously studied on human monoclonal antibodies against human TGF-β type II receptor to achieve the above-mentioned objective. The present inventors thus succeeded, for the first time in the world, in preparing various human monoclonal antibodies that bind to human TGF-β type II receptor, particularly various monoclonal antibodies that bind to human TGF-β type II receptor to inhibit the signal transduction of human TGF-β into cells, by immunizing transgenic mice which was created to produce human antibodies using recombinant technology, with soluble recombinant human TGF-β type II receptor.

Further, the present inventors found that a substance that binds to the TGF-β type II receptor, represented by the present human monoclonal antibody that binds to the human TGF-β type II receptor (other examples include chemically synthesized low-molecular-weight compounds and antisense nucleic acids) not only significantly inhibits the signal transduction of human TGF-β into cells mediated by the human TGF-β type II receptor, but also had a therapeutic effect on various diseases (e.g., kidney diseases (for example, nephritis, kidney fibrosis, and nephrosclerosis); various tissue fibroses, such as kidney fibrosis and pulmonary fibrosis; cirrhosis; rheumatoid arthritis; keloid of skin; etc.), and thus completed the present invention.

As the monoclonal antibodies of the present invention are from human, they have no antigenicity to the human host, which is a major therapeutic problem (side effect) in medical treatment with antibody pharmaceuticals comprising antibodies derived from non-human mammals, such as mice. This means the antibodies of the present invention do not induce severe host immune rejection caused by HAMA (human anti-mouse antigenicity), and, therefore, dramatically elevates the value of the antibody as a pharmaceutical.

Further, a substance that binds to TGF-β type II receptor to suppress or inhibit the signal transduction into cells mediated by the receptor, which is represented by the human monoclonal antibody of the present invention that binds to the human TGF-β type II receptor (other examples include chemically synthesized low-molecular-weight compounds and compounds isolated from animals, plants, bacteria, microorganisms, etc.), and also a pharmaceutical composition comprising the substance are useful as a pharmaceutical for treating or preventing various types of diseases caused by the action of TGF-β by suppressing or inhibiting the onset and/or progress of the diseases. Such diseases are exemplified by kidney diseases (kidney fibrosis, nephritis, renal failure, nephrosclerosis, etc.); lung diseases (e.g., pulmonary fibrosis, pneumonia, etc.); liver diseases (e.g., liver tissue fibrosis, cirrhosis, hepatitis, etc.); skin diseases (e.g., wound, scleroderma, psoriasis, keloid, etc.) arthritis (e.g., rheumatoid arthritis, osteoarthritis, etc.); vascular diseases (e.g., vascular restenosis, rheumatic vasculitis, etc.); tissue fibroses in various organs (including tissue fibrosis accompanied by various cancers); arteriosclerosis (including accompanying tissue fibrosis); and so on.

Specifically, the present invention provides the following:

(1) a human monoclonal antibody that binds to ahuman TGF-β type II receptor, or a portion of the antibody;

(2) the human monoclonal antibody or a portion thereof according to (1), wherein the human monoclonal antibody has the activity to inhibit the signal transduction into cells induced by binding of a human TGF-β to the human TGF-β type II receptor;

(3) the human monoclonal antibody or a portion thereof according to (1), wherein the human monoclonal antibody has the character selected from the group consisting of:

(a) suppressing the cell growth of human osteosarcoma cell line MG-63 (ATCC CRL-1427) that is induced by the stimulus with a human TGF-β1;

(b) suppressing the human TGF-β1 stimulus-induced suppression of cell growth of human lung cancer cell line A549 (ATCC CCL-185); and (c) suppressing the production of a fibronectin or connective tissue growth factor by human osteosarcoma cell line MG-63 (ATCC CRL-1427) that is induced by the stimulus with a human TGF-β1;

(4) the human monoclonal antibody or a portion thereof according to any one of (1) to (3), wherein the human monoclonal antibody is from a transgenic non-human mammal that produces human antibodies;

(5) the human monoclonal antibody or a portion thereof according to (4), wherein said human monoclonal antibody is produced by immunizing a transgenic non-human mammal that produces human antibodies with cells expressing a human TGF-β type II receptor or, the entire human TGF-β type II receptor molecule or a portion thereof;

(6) the human monoclonal antibody or a portion thereof according to (4) or (5), wherein the transgenic non-human mammal is a transgenic mouse;

(7) the human monoclonal antibody or a portion thereof according to any one of (1) to (6), wherein a V region DNA encoding a heavy chain variable region of the human monoclonal antibody is derived from a V gene segment selected from the group consisting of DP-54 (3-07), DP-73 (5-51) and DP-77 (3-21);

(8) the human monoclonal antibody or a portion thereof according to any one of (1) to (6), wherein a V region DNA encoding a light chain variable region of the human monoclonal antibody is derived from a V gene segment selected from the group consisting of A30, DPK-15 (A19), DPK-24 (B-3) and DPK-28 (A18);

(9) the human monoclonal antibody or a portion thereof according to any one of (1) to (8), wherein a V region DNA encoding a heavy chain variable region of the human monoclonal antibody is derived from a V gene segment selected from the group consisting of DP-54 (3-07), DP-73 (5-51) and DP-77 (3-21) and wherein a V region DNA encoding a light chain variable region of the human monoclonal antibody is derived from a V gene segment selected from the group consisting of A30, DPK-15 (A19) DPK-24 (B-3) and DPK-28 (A18);

(10) the human monoclonal antibody or a portion thereof according to (1), wherein a heavy chain variable region of the human monoclonal antibody comprises the amino acid sequence selected from the group consisting of:

(a) the amino acid sequence from residues 21 to 117 of SEQ ID NO: 4;

(b) the amino acid sequence from residues 21 to 117 of SEQ ID NO: 4, wherein one or more amino acids have been deleted, substituted, inserted, or added;

(c) the amino acid sequence from residues 2 to 98 of SEQ ID NO: 6;

(d) the amino acid sequence from residues 2 to 98 of SEQ ID NO: 6, wherein one or more amino acids have been deleted, substituted, inserted, or added;

(e) the amino acid sequence from residues 21 to 116 of SEQ ID NO: 8;

(f) the amino acid sequence from residues 21 to 116 of SEQ ID NO: 8, wherein one or more amino acids have been deleted, substituted, inserted, or added;

(g) the amino acid sequence from residues 21 to 117 of SEQ ID NO: 10; and (h) the amino acid sequence from residues 21 to 117 of SEQ ID NO: 10, wherein one or more amino acids have been deleted, substituted, inserted, or added;

(11) the human monoclonal antibody or a portion thereof according to (1), wherein a light chain variable region of the human monoclonal comprises any one of the amino acid sequence selected from the group consisting of:

(a) the amino acid sequence from residues 23 to 117 of SEQ ID NO: 12;

(b) the amino acid sequence from residues 23 to 117 of SEQ ID NO: 12, wherein one or more amino acids have been deleted, substituted, inserted, or added;

(c) the amino acid sequence from residues 21 to 116 of SEQ ID NO: 14;

(d) the amino acid sequence from residues 21 to 116 of SEQ ID NO: 14, wherein one or more amino acids have been deleted, substituted, inserted, or added;

(e) the amino acid sequence from residues 22 to 120 of SEQ ID NO: 16;

(f) the amino acid sequence from residues 22 to 120 of SEQ ID NO: 16, wherein one or more amino acids have been deleted, substituted, inserted, or added;

(g) the amino acid sequence from residues 18 to 113 of SEQ ID NO: 18; and (h) the amino acid sequence from residues 18 to 113 of SEQ ID NO: 18, wherein one or more amino acids have been deleted, substituted, inserted, or added;

(12) a cell producing the human monoclonal antibody according to any one of (1) to (11);

(13) the cell according to (12), wherein the cell is a fused cell produced by fusing a B cell from a mammal that produces the human monoclonal antibody with a myeloma cell derived from a mammal;

(14) the cell according to (12), wherein the cell is a recombinant cell, which has been transformed by either or both of DNA encoding the heavy chain and DNA encoding the light chain of the human monoclonal antibody;

(15) a pharmaceutical composition comprising the human monoclonal antibody or a portion thereof according to any one of (1) to (11), and a pharmaceutically acceptable carrier;

(16) the pharmaceutical composition according to (15), wherein the pharmaceutical composition is used to inhibit the signal transduction into cells induced by binding of a human TGF-β to a human TGF-β type II receptor;

(17) a pharmaceutical composition for suppressing a tissue fibrosis, which comprises a substance that binds to a human TGF-β type II receptor so that the signal transduction into cells through the receptor is suppressed or inhibited, and a pharmaceutically acceptable carrier;

(18) the pharmaceutical composition according to (17), wherein the substance is the human monoclonal antibody or a portion thereof according to any one of (1) to (11);

(19) the pharmaceutical composition according to (17) or (18), wherein the tissue fibrosis is fibrosis in the lung, liver, kidney, or skin;

(20) the pharmaceutical composition according to (19), wherein the tissue fibrosis is fibrosis in the kidney;

(21) a pharmaceutical composition to treat or prevent kidney diseases, which comprises a substance that binds to a human TGF-β type II receptor so that the signal transduction into cells through the receptor is suppressed or inhibited, and a pharmaceutically acceptable carrier;

(22) the pharmaceutical composition according to (22), wherein the substance is the human monoclonal antibody or a portion thereof according to any one of (1) to (11);

(23) a pharmaceutical composition used to suppress or treat nephrosclerosis, pulmonary fibrosis, cirrhosis, vascular restenosis, arteriosclerosis, psoriasis, scleroderma, atopy, keloid, or arthritis, which comprises a substance that binds to a human TGF-β type II receptor so that the signal transduction into cells through the receptor is suppressed or inhibited, and a pharmaceutically acceptable carrier; and

(24) the pharmaceutical composition according to (23), wherein the substance is the human monoclonal antibody or a portion thereof according to any one of (1) to (11).

The present invention is described in detail herein below by defining terms used herein.

Herein, "mammal" include human, bovine, goat, rabbit, mouse, rat, hamster, and guinea pig; preferably human, rabbit, rat, hamster, and mouse; and particularly preferably human, rat, hamster, and mouse.

The term "mammal except human" and "non-human mammal" herein refer to the same meaning indicating all the above-defined mammals except human.

"Amino acid" used in the present invention refer to any amino acid existing in nature and preferably the following amino acids presented by alphabetical triplets or single letter codes used to represent amino acids:

(Gly/G) glycine, (Ala/A) alanine, (Val/V) valine, (Leu/L) leucine, (Ile/I) isoleucine, (Ser/S) serine, (Thr/T) threonine, (Asp/D) aspartic acid, (Glu/E) glutamic acid, (Asn/N) asparagine, (Gln/Q) glutamine, (Lys/K) lysine, (Arg/R) arginine, (Cys/C) cysteine, (Met/M) methionine, (Phe/F) phenylalanine, (Tyr/Y) tyrosine, (Trp/W) tryptophan, (His/H) histidine, and (Pro/P) proline.

As used herein, the term "human TGF-α type II receptor" (also referred to as "TβRII") refers to human TGF-β type II receptor with the structure and function previously described in reports as shown above (for example, Cell, Vol. 68, No. 4, p. 775-785, 1992; Adv. Immunol., Vol. 55, p. 181-220, 1994; GenBank Accession No.:M85079).

A native human TGF-β type II receptor has the structural properties and features as described below.

Human TGF-β type II receptor is a transmembrane protein consisting of 567 amino acids, comprising an extracellular domain (136 amino acids), a transmembrane domain (30 amino acids), and a cytoplasmic domain (378 amino acids). Further, TGF-β type II receptor is a single-transmembrane protein whose extracellular domain is relatively short in size and which has the serine/threonine kinase structure containing two kinase domains. Further, the cytoplasmic domain contains an aspartic acid (Asp)-linked sugar chain, and this domain has 12 cysteine (Cys) residues which provide a characteristic tertiary structure.

The kinase domain of TGF-β type II receptor is a protein kinase specific to serine/threonine and shares a homology of about 43% with that of the TGF-β type I receptor. This kinase domain is essential for the signal transduction of TGF-β into cells (J. Biol. Chem., Vol. 269, p. 30753, 1994).

TGF-β type II receptor is a very important molecule which transduces TGF-β signals into the cell in concert with TGF-β type I receptor. The TGF-β type II receptor binds to TGF-β by itself. Binding of TGF-β to the TGF-β type II receptor has been demonstrated to cause the formation of a hetero-tetramer complex of the TGF-β type II receptor and the TGF-β type I receptor on cell surface (J. Biol. Chem., Vol. 269, p. 20172, 1994). Once the complex consisting of the two receptors is formed in the presence of TGF-β, the TGF-β type II receptor phosphorylates the GS domain (see above) of the TGF-β type I receptor and thereby activates the TGF-β type I receptor. As a result, other intracellular substrates are phosphorylated to further transduce the TGF-β signal downstream (Nature, Vol. 370, p. 341, 1994).

In addition, the "human TGF-β type II receptor" of this invention (also referred to as "TβRII") includes mutants of the natural human TGF-β type II receptor, which has substantially the same amino acid sequence as that of the native primary structure (amino acid sequence) described in the above-mentioned reports.

Herein, the term "mutants of the natural human TGF-β type II receptor having substantially the same amino acid sequence" refers to the following mutant proteins.

Specifically, such proteins include a mutant protein having an amino acid sequence wherein one or more amino acids, preferably 1 to 10 amino acids, particularly preferably 1 to 5 amino acids, in the amino acid sequence of the natural human TGF-β type II receptor, are substituted, deleted and/or modified, and a mutant protein having an amino acid sequence wherein one or more amino acids, preferably 1 to 10 amino acids, particularly preferably 1 to 5 amino acids, are added to the amino acid sequence, so long as the protein has substantially the same biological properties as the natural human TGF-β type II receptor.

Furthermore, a mutant having a combination of two or more of the above alterations including substitution, deletion, modification, and addition is also included.

The human TGF-β type II receptor of the present invention can be produced by methods known in the technical field, such as recombinant technology, chemical synthesis, and cell culture, or by modified methods thereof.

The human TGF-β type II receptor (also referred to as "TβRII") of the present invention also includes "a portion" of the human TGF-β type II receptor. The term "a portion" herein refers to a polypeptide comprising any arbitrary partial amino acid sequence derived from the above-defined human TGF-β type II receptor.

Preferably, it refers to the extracellular domain of human TGF-β type II receptor defined above, or an arbitrary part thereof.

"A portion" of the human TGF-β type II receptor (preferably, the extracellular domain of the human TGF-β type II receptor or any portion thereof) can be produced according to methods known in the technical field, or modified methods thereof, including recombinant technology and chemical synthesis. It can also be produced by appropriately digesting the human TGF-β type II receptor isolated by the cell culture method with proteases and such.

The "human monoclonal antibody" of this invention is a human monoclonal antibody that binds to the human TGF-β type II receptor defined above.

More specifically, a human monoclonal antibody includes a human immunoglobulin whose all the regions including the variable region and constant region of the heavy chain (H chain) and the variable region and constant region of the light chain (L chain) constituting the immunoglobulin are from genes encoding a human immunoglobulin. The L chain includes the human κ chain and the human λ chain.

A human monoclonal antibody that binds to the human TGF-β type II receptor of the present invention is a monoclonal antibody having any one of the features selected from the group consisting of (1) to (11) described above.

More specifically, the term "monoclonal antibody" refers to various monoclonal antibodies with various properties and industrial utilities described below in the examples and as indicated in the drawings.

As a preferable embodiment, a human monoclonal antibody of the present invention is a human monoclonal antibody that binds to the human TGF-β type II receptor, described in any one of (2) to (11) above.

In a more preferred embodiment, a human monoclonal antibody of the invention is a human monoclonal antibody that binds to the human TGF-β type II receptor according to any one of (7) to (11) of the present invention.

In a particularly preferred embodiment, a human monoclonal antibody of the invention is either the human monoclonal antibody binding to the human TGF-β type II receptor of (10) or (11) of the present invention.

A "human monoclonal antibody" of the present invention can be prepared by immunizing a human antibody-producing transgenic non-human mammal with any one of the immunogens (antigens) below:

(i) naturally occurring cells or artificially established cell lines expressing the above-defined human TGF-β type II receptor on the cell surface;

(ii) recombinant cells, which have been prepared by DNA recombinant technology to express the above-defined human TGF-β type II receptor on the cell surface;

(iii) cell lysate prepared by solubilizing the cells of (i) or (ii), or polypeptide fragments of human TGF-β type II receptor purified from the cell lysate;

(iv) recombinant cells, which have been prepared by DNA recombinant technology to express a portion of the above-defined human TGF-β type II receptor (particularly, the extracellular domain or an arbitrary peptide thereof are preferred) as a soluble polypeptide;

(v) culture supernatant obtained by culturing the recombinant cells of (iv), or the extracellular domain polypeptide of the human TGF-β type II receptor purified from the culture supernatant (soluble human TGF-β type II receptor) and (vi) chemically synthesized partial human TGF-β type II receptor (particularly, the extracellular domain or an arbitrary peptide thereof are preferred).

Further, a human monoclonal antibody of the present invention can also be obtained from the culture supernatant of the "recombinant cells" of the present invention, which cells produce recombinant human monoclonal antibodies. The recombinant cells are prepared using DNA recombinant technology by transforming host cells with cDNAs encoding respective heavy chain and light chain of the human monoclonal antibody of the present invention.

Further, a human monoclonal antibody of the present invention may be any one of the isotypes including IgG (IgG1, IgG2, IgG3, and IgG4), IgM, IgA (IgA1 and IgA2), IgD, or IgE; preferably IgG (IgG1, IgG2, IgG3, and IgG4); and more preferably IgG1, IgG2, or IgG4. IgG4 is particularly preferred.

A human monoclonal antibody of the present invention can be produced by immunizing human antibody-producing transgenic non-human mammals, such as the human antibody-producing transgenic mice described below, with any one of the immunogens (antigens) described above as (i) to (vi). Such human monoclonal antibodies can be prepared by conventional methods for preparing monoclonal antibodies.

Specifically, human antibody producing transgenic non-human mammals are immunized, for example, with an antigen mentioned above together with Freund's adjuvant, if necessary. Polyclonal antibodies can be obtained from the serum obtained from the immunized animal. Monoclonal antibodies are produced as follows. Hybridomas (fused cells) are produced by fusing the antibody-producing cells obtained from the immunized animal and myeloma cells incapable of producing autoantibodies. Then the hybridomas are cloned, and clones producing the monoclonal antibodies showing specific affinity to the antigen used for immunizing the mammal are screened.

More specifically, a monoclonal antibody can be produced as follows. Immunizations are done by injecting or implanting once or several times an immunogen of any one of (i) to (iii) above, if necessary, with Freund's adjuvant, subcutaneously, intramuscularly, intravenously, through the footpad, or intraperitoneally into the human antibody-producing transgenic non-human mammal (particularly preferred are the "human antibody-producing transgenic mouse" described below) Usually, immunizations are performed once to four times every one to fourteen days after the first immunization. Antibody-producing cells are obtained from the immunized mammal in about one to five days after the last immunization. The number of times and interval of the immunizations can be appropriately altered according to the properties of the used immunogen.

Hybridomas (fused cells) that secrete human monoclonal antibodies can be prepared according to the method by Köhler and Milstein (Nature, Vol. 256, pp. 495-497 (1975)) and to modified method thereof. Namely, hybridomas are prepared by fusing antibody-producing cells from spleen, lymph node, bone marrow, or tonsil of the human antibody-producing transgenic non-human mammal immunized as mentioned above, preferably spleen, with myelomas without autoantibody-producing ability, which are derived from, preferably, mammal, such as mouse, rat, guinea pig, hamster, rabbit, or human, or more preferably, mouse, rat, or human.

For example, mouse-derivedmyeloma P3/X63-AG8.653 (653, ATCC No. CRL1580), P3/NSI/1-Ag4-1 (NS-1), P3/X63-Ag8.U1 (P3U1), SP2/0-Ag14 (Sp2/0, Sp2), PAI, F0, or BW5147; rat-derived myeloma 210RCY3-Ag.2.3.; or human-derived myeloma U-266AR1, GM1500-6TG-α1-2, UC729-6, CEM-AGR, D1R11, or CEM-T15 can be used as a myeloma for the cell fusion.

Monoclonal antibody producing cells (e.g., hybridoma) can be screened by cultivating the cells, for example, in microtiter plates and by measuring the reactivity of the culture supernatant in the well wherein the growth of hybridoma is observed, to the immunogen used for the immunization mentioned above, for example, by an enzyme immunoassay, such as radio immunoassay (RIA) and enzyme-linked immuno-solvent assay (ELISA).

Monoclonal antibody can be produced from hybridoma by cultivating the hybridoma in vitro or in vivo, such as in the ascites of mouse, rat, guinea pig, hamster, or rabbit, preferably mouse or rat, more preferably mouse, and isolating the antibody from the resulting culture supernatant or ascites fluid of a mammal.

Furthermore, monoclonal antibody can be obtained in a large quantity by cloning genes encoding a monoclonal antibody from a hybridoma or "recombinant cell" producing a recombinant human monoclonal antibody of the present invention described below, generating transgenic animal, such as bovine, goat, sheep, or pig wherein the genes encoding the monoclonal antibody is integrated into its endogenous genome using transgenic animal generating technique, and recovering the monoclonal antibody derived from the human monoclonal antibody gene from milk of the transgenic animals (Nikkei Science, April, pp. 78-84 (1997)).

Cultivation of monoclonal antibody-producing cells in vitro can be performed depending on the property of cells to be cultured, on the object of a test/study, and on various culture, using known nutrient media or any nutrient media derived from known basal media for growing, maintaining, and storing the hybridomas to produce monoclonal antibodies in the culture supernatant.

Examples of basal media are low calcium concentration media, such as Ham'F12 medium, MCDB153 medium, and low calcium concentration MEM medium; and high calcium concentration media, such as MCDB104 medium, MEM medium, D-MEM medium, RPMI1640 medium, ASF104 medium, and RD medium. The basal media can contain, for example, sera, hormones, cytokines, and/or various inorganic or organic substances depending on the objective.

Monoclonal antibodies can be isolated and purified from the culture supernatant or ascites mentioned above by saturated ammonium sulfate precipitation, euglobulin precipitation method, caproic acid method, caprylic acid method, ion exchange chromatography (DEAE or DE52), affinity chromatography using anti-immunoglobulin column or protein A column.

The human monoclonal antibodies of the present invention also includes a monoclonal antibody comprising the heavy chain and/or the light chain wherein either or both of the chains have deletions, substitutions or additions of one or more amino acids in the sequences thereof.

The term "one or more amino acids" herein means one or more amino acid residues, specifically indicates one to ten amino acid residues, preferably one to five amino acid residues.

The partial modification (deletion, substitution, insertion, and addition) of the amino acid sequence described above can be introduced into the human monoclonal antibodies of the present invention by partially modifying the nucleotide sequence encoding the amino acid sequence. The partial modification of the nucleotide sequence can be performed by conventional methods like site-specific mutagenesis (Proc. Natl. Acad. Sci. USA, Vol. 81, p. 5662-5666, 1984).

The "human antibody-producing transgenic non-human mammal" of the present invention, in particular, the preferable embodiment, human antibody-producing transgenic mouse, can be prepared according to methods in the literature (Nature Genetics, Vol. 7, p. 13-21, 1994; Nature Genetics, Vol. 15, p. 146-156, 1997; Published Japanese Translation of International Publication No. Hei 4-504365; Published Japanese Translation of International Publication No. Hei 7-509137; Nikkei Science, June, p40-50, 1995; International Publication WO94/25585; Nature, Vol. 368, p. 856-859, 1994; Published Japanese Translation of International Publication No. Hei 6-500233; etc.).

The human antibody-producing transgenic mice can be produced, specifically, for example, via the following processes; other human antibody-producing non-human transgenic mammals can be produced in the same manner.

(1) A process for preparing knockout mice whose endogenous immunoglobulin heavy chain gene locus has been functionally inactivated, which the inactivation can be accomplished by substituting at least a portion of the endogenous mouse immunoglobulin heavy chain gene locus for a drug-resistance gene (the neomycin resistance gene, etc.) through homologous recombination;

(2) A process for preparing knockout mice whose endogenous immunoglobulin light chain gene locus (a K chain gene locus in particular) has been functionally inactivated, which the inactivation is accomplished by substituting at least a portion of the endogenous mouse immunoglobulin light chain gene locus for a drug-resistance gene (the neomycin resistance gene, etc.) through homologous recombination;

(3) A process for preparing transgenic mice wherein a desired portion of the human immunoglobulin heavy chain gene locus has been integrated into a mouse chromosome using a vector, such as yeast artificial chromosome (YAC) vector, capable of transporting mega base genes;

(4) A process for preparing transgenic mice wherein a desired portion of the human immunoglobulin light chain (a κ gene in particular) gene locus has been integrated into a mouse chromosome using a vector, such as YAC vector, capable of transporting mega base genes;

(5) A process for preparing transgenic mice wherein both the mouse endogenous heavy chain and light chain gene loci have been functionally inactivated and both desired portions of the human immunoglobulin heavy chain and light chain genes loci have been integrated in a chromosome, which preparation is achieved by crossbreeding, in arbitrary order, the knockout mice and the transgenic mice described above in (1) to (4).

The knockout mice mentioned above can be prepared by substituting any suitable region of the mouse endogenous immunoglobulin gene locus for a foreign marker gene (neomycin resistance gene, etc.) through homologous recombination so that the immunoglobulin gene locus can be inactivated so as not to cause a rearrangement of the gene locus. For example, the method designated as positive-negative selection (PNS) can be used for the inactivation by homologous recombination (Nikkei Science, May edition, p. 52-62, 1994).

The functional inactivation of the immunoglobulin heavy chain locus can be achieved, for example, by introducing a lesion into a portion of the J region or a portion of the C region (the Cμ region, for example). The functional inactivation of the immunoglobulin light chain (κ chain, for example) can also be achieved, for example, by introducing a lesion into a portion of the J region, a portion of the C region, or a region extending from the J region to the C region.

The transgenic mouse can be prepared according to conventional methods used for producing transgenic animals (for example, see "Newest Manual of Animal Cell Experiment", LIC press, Chapter 7, pp. 361-408, (1990)). Specifically, for example, a transgenic mouse can be produced as follows. Hypoxanthine-guanine phosphoribosyl transferase (HPRT)—negative embryonic stem cells (ES cells) obtained from a normal mouse blastocyst is fused by spheroplast fusion method with a yeast cell containing an YAC vector, wherein the gene encoding human immunoglobulin heavy chain locus or light chain locus, or its fragment and a HPRT gene have been inserted. ES cells wherein the foreign gene has been integrated into the mouse endogenous genome are screened by the HAT selection method. Then, the ES cells screened are microinjected into a fertilized egg (blastocyst) obtained from another normal mouse (Proc. Natl. Acad. Sci. USA, Vol. 77, No. 12, pp. 7380-7384 (1980); U.S. Pat. No. 4,873,191). The blastocyst is transplanted into the uterus of another normal mouse as the foster mother. Then, chimeric transgenic mice are born from the foster mother mouse. By mating the chimeric transgenic mice with normal mice, heterozygous transgenic mice are obtained. By mating the heterozygous transgenic mice with each other, homozygous transgenic mice are obtained according to Mendel's laws.

The term "portion of a monoclonal antibody" used herein refers to a partial region of the human monoclonal antibody of the present invention as mentioned above, and specifically, includes F(ab')$_2$, Fab', Fab, Fv (variable fragment of antibody), sFv, dsFv (disulfide stabilized Fv), or dAb (single domain antibody) (Exp. Opin. Ther. Patents, Vol. 6, No. 5, pp. 441-456 (1996)).

"F(ab')$_2$" and "Fab'" can be produced by treating immunoglobulin (monoclonal antibody) with a protease, such as pepsin and papain, and refers to antibody fragments generated by digesting immunoglobulin near the disulfide bonds existing between the hinge regions in each of the two H chains. For example, papain cleaves IgG upstream of the disulfide bonds existing between the hinge regions in each of the two H chains to generate two homologous antibody fragments in which an L chain composed of $V_L$ (L chain variable region) and $C_L$ (L chain constant region), and an H chain fragment composed of $V_H$ (H chain variable region) and $C_H\gamma1$ ($\gamma_1$ region in the constant region of H chain) are connected at their C terminal regions through a disulfide bond. Each of these two homologous antibody fragments is called Fab'. Pepsin also cleaves IgG downstream of the disulfide bonds existing between the hinge regions in each of the two H chains to generate an antibody fragment slightly larger than the fragment wherein the two above-mentioned Fab' are connected at the hinge region. This antibody fragment is called F(ab')$_2$.

The term "monoclonal antibody-producing cell" or "recombinant cell" producing the recombinant human monoclonal antibody of this invention refers to any cell producing the above-described human monoclonal antibody of this invention.

Specific examples include cells as below:

(1) human monoclonal antibody-producing B cells that are obtainable from the above-described human antibody-producing transgenic non-human mammal, which animal can be produced by immunizing the animal with the above-defined immunogen (antigen);

(2) the above-described hybridoma (fused cell) prepared by fusing the human monoclonal antibody producing B cells described above with myelomas derived from mammal; and (3) a recombinant cell that produces a recombinant human monoclonal antibody obtained by transforming other cell than the B cell and hybridoma (e.g. Chinese hamster ovarian (CHO) cell, Baby hamster kidney (BHK) cell, etc.) with genes (either the heavy chain-encoding gene or the light chain-encoding gene, or both) encoding the human monoclonal antibody isolated from the human monoclonal antibody producing B cell or hybridoma.

The recombinant human monoclonal antibody-producing recombinant cells of (3) refer to recombinant cells producing recombinant products of the human monoclonal antibody produced by B cells of (1) or hybridomas of (2).

The "substance" of the present invention, specifically "substance that binds to a human TGF-β type II receptor so that the signal transduction into cells through the receptor is suppressed or inhibited", encompasses naturally occurring substances and artificially prepared arbitrary substances.

Further, the substance includes an arbitrary substance which competitively binds to human TGF-β type II receptor with the in-vivo ligand, TGF-β, of the receptor.

The substances can be categorized into "proteinaceous substance" and "non-proteinaceous substance".

The "proteinaceous substance" includes polypeptides, polyclonal antibodies, monoclonal antibodies, and a portion of the monoclonal antibody.

When the substance is an antibody, a monoclonal antibody is preferable. When the substance is a monoclonal antibody, it includes not only monoclonal antibodies derived from a non-human mammal but also recombinant chimeric monoclonal antibody, recombinant humanized monoclonal antibody, and the above-mentioned "human monoclonal antibody".

When the substance is a polypeptide other than antibody, it includes an arbitrary polypeptide, fragments of the polypeptide (oligopeptides), fused polypeptide, and chemically modifications thereof. The oligopeptide includes a peptide consisting of 5 to 30 amino acids, preferably 5 to 20 amino acids. The chemically modified peptide can be designed depending on various purposes, such as to increase the half-life in blood when it is administered to a living body or to enhance resistance to degradation or absorption in the digestive tract when it is administered orally.

The "non-proteinaceous substance" includes arbitrary chemically-synthesized compounds or arbitrary chemical substances isolated from animals and plants (for example, plants, microorganisms, bacteria, insects, fishes, and crustaceans). Specifically, such a substance is a compound with a molecular weight of about 100 to 1000 Da or smaller, preferably a compound with a molecular weight of about 100 to 800 Da, more preferably a compound with a molecular weight of 100 to 600 Da.

The term "pharmaceutical composition" as referred to in the present invention means a composition useful as a pharmaceutical comprising as an active ingredient a human monoclonal antibody that binds to the human TGF-β type II receptor of the present invention or a portion thereof, or the above-mentioned "substance that binds to a human TGF-β type II receptor so that the signal transduction into cells through the receptor is suppressed or inhibited", as well as comprising a "pharmaceutically acceptable carrier"

The "pharmaceutically acceptable carrier" includes excipients, diluents, expanders, disintegrating agents, stabilizers, preservatives, buffer, emulsifiers, aromatics, colorants, sweeteners, viscosity increasing agents, flavors, dissolving agents, or other additives.

Using one or more of such carriers, a pharmaceutical composition can be formulated into tablets, pills, powders, granules, injections, solutions, capsules, troches, elixirs, suspensions, emulsions, or syrups.

The pharmaceutical composition can be administered orally or parenterally. Other forms for parenteral administration include solutions for external application, suppositories for rectal administration, and pessary, prescribed by usual methods, which comprises one or more active ingredient.

The dosage can vary depending on the age, sex, weight, and symptoms of a patient, effect of treatment, administration route, period of treatment, or the kind of active ingredient (protein or antibody mentioned above) contained in the pharmaceutical composition. Usually, the pharmaceutical composition can be administered to an adult in a dose of 10 μg to 1000 mg (or 10 μg to 500 mg) per one administration. Depending on various conditions, a lower dosage may be sufficient in some cases, and a higher dosage may be necessary in other cases.

In particular, an injection can be produced by dissolving or suspending the antibody in a non-toxic, pharmaceutically acceptable carrier, such as physiological saline or commercially available distilled water for injections, by adjusting the concentration to 0.1 μg antibody/ml carrier to 10 mg antibody/ml carrier.

The injection thus produced can be administered to a human patient in need of treatment in a dose of 1 μg to 100 mg/kg body weight, preferably 50 μg to 50 mg/kg body weight, once or more times a day. Examples of administration routes are medically appropriate administration routes, such as intravenous injection, subcutaneous injection, intradermal injection, intramuscular injection, or intraperitoneal injection, preferably intravenous injection.

The injection can be also prepared into a non-aqueous diluent (for example, propylene glycol; polyethylene glycol; vegetable oil, such as olive oil; and alcohols, such as ethanol), suspension, or emulsion.

The injection can be sterilized by filtration with a bacteria-non-penetratable filter, by mixing bacteriocide, or by irradiation. The injection can be prepared at the time of use. Namely, it is freeze-dried to make a sterile solid composition, and can be dissolved in sterile distilled water for injection or another solvent before use.

The pharmaceutical compositions of the present invention are useful to inhibit the transduction of the TGF-β signal into cells mediated by the TGF-β type II receptor, which signal is associated with various morbid states and the onsets of diseases.

Further, the pharmaceutical compositions of the present invention are useful as pharmaceuticals for treating or preventing diseases by suppressing or inhibiting the onset and/or progress of various diseases: for example, kidney diseases (kidney fibrosis, nephritis, renal failure, nephrosclerosis, etc.); lung diseases (e.g., pulmonary fibrosis, pneumonia, etc.); liver diseases (e.g., liver tissue fibrosis, cirrhosis, hepatitis, etc.); skin diseases (e.g., wound, scleroderma, psoriasis, keloid, etc.); arthritis (e.g., rheumatoid arthritis, osteoarthritis, etc.); vascular diseases (e.g., vascular restenosis, rheumatic vasculitis, etc.); tissue fibroses in various organs (including tissue fibrosis complicated to various cancers), and arteriosclerosis (including complicated tissue fibrosis).

The human monoclonal antibodies of the present invention or pharmaceutical compositions thereof are particularly useful as antibody pharmaceuticals because they do not induce host immunorejection caused by HAMA (human anti-mouse antibody) as the monoclonal antibodies are derived from human.

The therapeutic effects of the pharmaceutical composition of the present invention on various diseases can be examined and evaluated according to conventional methods by administering the composition to known animals as disease models.

For example, evaluation of the therapeutic effect on kidney fibrosis, which is a tissue fibrosis as well as a kidney disease, can be performed by a method using a renal failure model mouse (unilateral ureteral obstruction (UUO) model), in which unilateral ureteral ligation obstructs renal blood filtration in the kidney and results in renal failure in the mouse. After administration of the inventive pharmaceutical composition to the mouse, the examination is achieved by measuring the degree of inhibition of an increase of hydroxyproline production, which is an index of the onset of nephritis and kidney fibrosis induced by the renal failure. A decrease in the hydroxyproline concentration indicates the efficacy of the pharmaceutical composition for the treatment of the kidney disease.

Further, an alternative method comprises administration of a pharmaceutical composition of the present invention to a model rat in which nephritis is induced by administering an antibody against Thy-1, a cell-surface marker, and measuring amounts of protein excreted in the urine, serum creatinine level, and the reduced levels of production of extracellular matrix (fibronectin, type I collagen, etc.), which are all indices of the onsets of nephritis and kidney fibrosis that are induced by functional failure of kidney (Nephron, Vol. 78, p. 453-463, 1998; Kidney Blood Press Res., Vol. 22, p. 5-12, 1999). The reduced amount of protein in the urine, reduced level of serum creatinine, and reduced amounts of fibronectin and type I collagen demonstrate the effect of the pharmaceutical composition for treating kidney diseases.

Using the model animals described in detail in the literature ("Preparation of animals as disease models: Testing and experimental methods for the development of new drugs" p. 34-46,1993, Technological Information Society evaluation can be performed for kidney diseases including, for example, minimal change glomerular disease (for example, minimal change nephrotic syndrome (MCNS)), focal glomerular sclerosis (FGS), membraneous glomerulonephritis (membranous nephropathy (MN)), IgA nephropathy, mesangial proliferative glomerulonephritis, acute post-streptococcal glomerulonephritis (APSGN, crescentic (extracapillary) glomerulonephritis, interstitial nephritis, and acute renal failure.

Using the model animals described in detail in the literature ("Preparation of animals as disease models: Testing and experimental methods for the development of new drugs" p. 229-235, 1993, Technological Information Society), evaluation can be performed for skin diseases including, for example, injuries, keloid, atopy, dermatitis, scleroderma, and psoriasis.

Using the model animals described in detail in the literature ("Preparation of animals as disease models: Testing and experimental methods for the development of new drugs" p. 349-358, 1993, Technological Information Society), evaluation can be performed for liver diseases including, for example, hepatitis (for example, viral hepatitis (type A, type B, type C, type E, etc.)), cirrhosis, and drug induced hepatic injuries.

For example, the effect on arteriosclerosis and restenosis can be evaluated using a restenosis model rat, in which pseudo-restenosis is caused by percutaneous transluminal coronary angioplasty (PTCA) with balloon catheter inserted in the aorta.

A DNA encoding the human TGF-β type II receptor used in the present invention can be prepared by conventional methods: cloning cDNA from mRNA encoding the human TGF-β type II receptor, isolating genomic DNA and splicing it, PCR using the cDNA or mRNA sequence as a template, chemical synthesis, and so on.

A DNA encoding the human TGF-β type II receptor of this invention can be prepared by cleaving (digesting) each DNA encoding the human TGF-β type II receptor as prepared above with an appropriate restriction enzyme, and ligating the obtained DNA fragments, in combination with a linker DNA or Tag if necessary, using an appropriate DNA polymerase and such.

cDNA encoding the human TGF-β type II receptor (hereinafter referred to as the desired protein) can be cloned from mRNA by, for example, the method described below.

First, the mRNA encoding the desired protein is prepared from tissues or cells expressing and producing the desired protein. mRNA can be prepared by isolating total RNA by a known method, such as the guanidine-thiocyanate method (Biochemistry, Vol. 18, p5294, 1979), the hot phenol method, or the AGPC method, and subjecting it to affinity chromatography using oligo-dT cellulose or poly-U Sepharose.

Then, using the mRNA obtained as a template, cDNAs are synthesized, for example, by well-known methods using reverse transcriptase, such as the method by Okayama et al (Mol. Cell. Biol. Vol. 2, p. 161 (1982); ibid. Vol. 3, p. 280 (1983)) or the method by Hoffman et al. (Gene Vol. 25, p. 263 (1983)), and converted into double-stranded cDNAs. A cDNA library is prepared by transforming *E. coli* with plasmid vectors, phage vectors, or cosmid vectors having those cDNAs or by transfecting *E. coli* after in vitro packaging.

The plasmid vectors used in this invention are not limited so long as they are replicated and maintained in hosts. Any phage vector that can be replicated in hosts can also be used. Examples of the cloning vectors usually used are pUC19, λgt10, λgt11, and so on. When the vector is applied to immunological screening as mentioned below, a vector having a promoter that enables to express a gene encoding the desired protein in a host is preferably used.

cDNA can be inserted into a plasmid according to, for example, the method by Maniatis et al. (Molecular Cloning, A Laboratory Manual, second edition, Cold Spring Harbor Laboratory, p. 1.53, 1989). cDNA can be inserted into a phage vector according to, for example, the method by Hyunh et al. (DNA cloning, a practical approach, Vol. 1, p. 49 (1985)). These methods can be simply performed by a commercially available cloning kit (for example, a product from TAKARA). The recombinant plasmid or phage vector thus obtained is introduced into an appropriate host cell, such as a prokaryote (for example, *E. coli*: HB101, DH5α, Y1090, DH10B, MC1061/P3, etc).

Examples of a method for introducing a plasmid into a host are, the calcium chloride method, the calcium chloride/rubidium chloride method, and the electroporation method, described in Molecular Cloning, A Laboratory Manual (second edition, Cold Spring Harbor Laboratory, p. 1.74 (1989)). Phage vectors can be introduced into host cells by, for example, a method in which the phage DNAs are introduced into grown hosts after in vitro packaging. In vitro packaging can be easily performed with a commercially available in vitro packaging kit (for example, a product from STRATAGENE or AMERSHAM).

The cDNA encoding the desired protein can be isolated from the cDNA library so prepared according to the method mentioned above by combining general cDNA screening methods.

For example, a clone comprising the desired cDNA can be screened by a known colony hybridization method (Crunstein et al. Proc. Natl. Acad. Sci. USA, Vol. 72, p. 3961 (1975)) or plaque hybridization method (Molecular Cloning, A Laboratory Manual, second edition, Cold Spring Harbor Laboratory, p. 2.108 (1989)) using $^{32}$P-labeled chemically synthesized oligonucleotides as probes, which correspond to the amino acid sequence of the desired protein. Alternatively, a clone having a DNA fragment encoding a specific region within the desired protein can be screened by amplifying the region by PCR with synthetic PCR primers.

When utilizing a cDNA library prepared using a cDNA expression vector (for example, λgt11 phage vector), the desired clone can be screened by the antigen-antibody reaction using an antibody against the desired protein. A screening method using PCR method is preferably used when many clones are subjected to screening.

The nucleotide sequence of the obtained DNA can be determined by the Maxam-Gilbert method (Maxam et al. Proc. Natl. Acad. Sci. USA, Vol. 74, p. 560 (1977)) or the dideoxynucleotide synthetic chain termination method using phage M13 (Sanger et al. Proc. Natl. Acad. Sci. USA, Vol. 74, pp. 5463-5467 (1977)). The whole or a part of the gene encoding the desired protein can be obtained by excising the clone obtained as mentioned above with restriction enzymes and so on.

Additionally, the DNA encoding the desired protein can be isolated from the genomic DNA derived from the cells expressing the desired protein as mentioned above by following methods.

Such cells are solubilized preferably by SDS or proteinase K, and the DNAs are deproteinized by repeating phenol extraction. RNAs are digested preferably with ribonuclease. The DNAs obtained are partially digested with appropriate restriction enzymes, and the DNA fragments obtained are amplified with appropriate phage or cosmid to generate a library. Then, clones having the desired sequence are detected, for example, by radioactively labeled DNA probes, and the whole or a portion of the gene encoding the desired protein is obtained from the clones by excision with restriction enzymes, etc.

A DNA encoding a desired protein can be prepared by the conventional PCR methods using known mRNA or cDNA of the desired protein as a template (Gene Amplification PCR method, Basics and Novel Development, Kyoritsu Publishers, 1992, etc).

A DNA encoding a desired protein can also be produced by chemical synthesis according to usual methods based on the nucleotide sequence encoding the protein.

The human TGF-β type II receptor of the present invention or a portion thereof (preferably, extracellular domain) can be prepared as a recombinant protein according to a conventional recombinant technology using DNA obtained by digesting the human TGF-β type II receptor-encoding DNA (the cDNA or the genomic DNA comprising introns) prepared by the method indicated above with appropriate restriction enzymes; ligating the resulting DNA fragment(s) encoding the human TGF-β type II receptor, according to need, with a linker DNA or Tag using an appropriate DNA polymerase or other enzymes.

Specifically, the preparation of the protein is illustrated as follows: the DNA construct as prepared above is inserted into a vector, described below in detail, to obtain an expression vector; a host cell, which will be described hereinafter, is transformed with the expression vector to obtain a transformant; the resulting transformant cells are cultured for the production and accumulation of the desired protein in the culture supernatant; the protein accumulated in the culture supernatant can be purified easily by using column chromatography, etc.

An expression vector available for producing the recombinant human TGF-β type II receptor (or extracellular domain thereof) is not particularly limited so long as it can be retained by replication or self-multiplication in various host cell of prokaryotic and/or eukaryotic cells, including plasmid vectors and phage vectors (Cloning Vectors: A laboratory Manual, Elsevier, N.Y., 1985).

The expression vector can be easily prepared by ligating according to conventional methods a DNA encoding the human TGF-β type II receptor (or extracellular domain) with a vector for recombination available in the art (plasmid DNA and bacteriophage DNA). Specific examples of the vectors for recombination are *E. coli*-derived plasmids such as pBR322, pBR325, pUC12, pUC13, and pUC19; yeast-derived plasmids, such as pSH19 and pSH15; and *Bacillus subtilis*-derived plasmids, such as pUB110, pTP5, and pC194. Examples of phages are bacteriophages, such as λ phage; and an animal or insect virus (pVL1393, Invitrogen), such as a retrovirus, vaccinia virus, and nuclear polyhedrosis virus.

A plasmid vector is useful for expressing the DNA encoding the human TGF-β type II receptor of this invention or its soluble extracellular domain, for expressing the human TGF-β type II receptor on host's cell surface, and for producing the soluble extracellular domain of the human TGF-β type II receptor. The plasmid vector is not limited so long as it expresses a gene encoding the human TGF-β type II receptor or its soluble extracellular domain in various prokaryotic and/or eukaryotic host cells and produces the polypeptide. Examples thereof include pMAL C2, pcDNA3.1(-), PEF-BOS (Nucleic Acids Res. Vol. 18, p. 5322 (1990) and so on), pME18S (Experimental Medicine: SUPPLEMENT, "Handbook of Genetic Engineering" (1992) and so on), etc.

When bacteria, particularly *E. coli* are used as host cells, an expression vector generally comprises, at least, a promoter/operator region, an initiation codon, a DNA encoding the protein of the present invention, a termination codon, a terminator region, and a replicon.

When yeast, animal cells, or insect cells are used as hosts, an expression vector preferably comprises, at least, a promoter, an initiation codon, a DNA encoding the human TGF-β type II receptor (or its extracellular domain) of the present invention, and a termination codon. It may also comprise a DNA encoding a signal peptide, enhancer sequence, 5'- and 3'-untranslated regions of the gene encoding the human TGF-β type II receptor of the present invention, splicing junctions, polyadenylation site, selectable marker region, and replicon. The expression vector may also contain, if required, a gene for gene amplification (marker) that is usually used according to purposes.

A promoter/operator region to express the human TGF-β type II receptor (or its extracellular domain) of the present invention in bacteria comprises a promoter, an operator, and a Shine-Dalgarno (SD) sequence (for example, AAGG). For example, when the host belongs to the genus *Escherichia*, it preferably comprises the Trp promoter, the lac promoter, the recA promoter, the λPL promoter, the lpp promoter, the tac promoter, or the like.

Examples of a promoter to express the human TGF-β type II receptor (or its extracellular domain) of the present invention in yeast are the PH05 promoter, the PGK promoter, the GAP promoter, the ADH promoter, and so on. When the host belongs to the genus *Bacillus*, examples thereof are the SL01 promoter, the SP02 promoter, the penP promoter, and so on.

When the host is a eukaryotic cell, such as mammalian cell, examples thereof are SV40-derived promoters, retrovirus promoters, heat shock promoters, and so on. As a matter of course, the promoter is not limited to the above examples. In addition, the use of an enhancer is also effective for the expression.

A preferable initiation codon is, for example, a methionine codon (ATG).

A commonly used termination codon (for example, TAG, TAA, TGA) is exemplified as a termination codon.

Usually, conventional natural or synthetic terminators are used as a terminator region.

A replicon means a DNA that is capable of replicating the whole DNA sequence in host cells, and includes natural plasmids, artificially modified plasmids (DNA fragments prepared from natural plasmids), synthetic plasmids, and so on. Examples of preferable plasmids are pBR322 or its artificial derivatives (DNA fragment prepared by treating pBR322 with appropriate restriction enzymes) for *E. coli*; yeast 2μ plasmid or yeast chromosomal DNA for yeast; and pRSVneo ATCC 37198, pSV2dhfr ATCC 37145, pdBPV-MMTneo ATCC 37224, pSV2neo ATCC 37149, pSV2bsr, and such for mammalian cells.

An enhancer sequence, polyadenylation site, and splicing junction that are usually used in the art, such as those derived from SV40 can also be used.

Usually available selectable markers can be used according to conventional methods. Examples thereof are resistance genes for antibiotics, such as tetracycline, ampicillin, or kanamycin.

Examples of genes for gene amplification are the dihydrofolate reductase (DHFR) gene, the thymidine kinase gene, the neomycin resistance gene, the glutamate synthase gene, the adenosine deaminase gene, the ornithine decarboxylase gene, the hygromycin-B-phosphotransferase gene, the aspartate transcarbamylase gene, etc.

The expression vector of the present invention can be prepared by contiguously and circularly ligating at least the above-mentioned promoter, initiation codon, DNA encoding the protein of the present invention, termination codon, and terminator region, to an appropriate replicon. If desired, appropriate DNA fragments (for example, linkers, other restriction sites) can be used by conventional methods, such as digestion with a restriction enzyme or ligation using T4 DNA ligase.

Transformants of the present invention can be prepared by introducing the expression vector mentioned above into host cells.

Host cells used in the present invention are not limited so long as they are compatible with an expression vector mentioned above and can be transformed. Examples thereof are various cells, such as wild-type cells or artificially established recombinant cells available in the technical field of the present invention (for example, bacteria (*Escherichia* and *Bacillus*), yeast (*Saccharomyces, Pichia*, and such), animal cells, or insect cells).

*E. coli* or animal cells are preferably used. Specific examples are *E. coli* (DH5α, DH10B, TB1, HB101, XL-2Blue, and such); mouse-derived cells (COP, L, C127, Sp2/0, NS-1, NIH 3T3, and such); rat-derived cells, hamster-derived cells (BHK, CHO, and such); monkey-derived cells (COS1, COS3, COS7, CV1, Velo, and such); and human-derived cells (Hela, diploid fibroblast-derived cells, myeloma, Namalwa, and such).

An expression vector can be introduced (transformed (transduced)) into host cells by known methods.

Transformation can be performed, for example, according to the method by Cohen et al. (Proc. Natl. Acad. Sci. USA, Vol. 69, p. 2110 (1972)); the protoplast method (Mol. Gen. Genet., Vol. 168, p. 111 (1979)); or the competent method (J. Mol. Biol., Vol. 56, p. 209 (1971)) when the hosts are bacteria (*E. coli, Bacillus subtilis*, and such); the method by Hinnen et al. (Proc. Natl. Acad. Sci. USA, Vol. 75, p. 1927 (1978)); or the lithium method (J. Bacteriol., Vol. 153, p. 163 (1983)) when the host is *Saccharomyces cerevisiae*; the method by Graham (Virology, Vol. 52, p. 456 (1973)) when the hosts are animal cells; and the method by Summers et al. (Mol. Cell. Biol., Vol. 3, pp. 2156-2165 (1983)) when the hosts are insect cells.

An extracellular domain of the human TGF-β type II receptors (soluble human TGF-β type II receptors) of the present invention can be produced by cultivating transformants (hereinafter, the term includes "transductants") comprising an expression vector prepared as mentioned above in nutrient media.

The nutrient media preferably comprise carbon source, inorganic nitrogen source, or organic nitrogen source necessary for the growth of host cells (transformants) Examples of the carbon source are glucose, dextran, soluble starch, and sucrose; and examples of the inorganic or organic nitrogen source are ammonium salts, nitrates, amino acids, corn steep liquor, peptone, casein, meet extract, soy bean cake, and potato extract. If desired, they may comprise other nutrients (for example, an inorganic salt (for example, calcium chloride, sodium dihydrogenphosphate, and magnesium chloride), vitamins, antibiotics (for example, tetracycline, neomycin, ampicillin, kanamycin, and so on)).

Cultivation is performed by methods known in the art. Cultivation conditions, such as temperature, pH of the media, and cultivation time, are selected appropriately so that the protein of the present invention is produced in large quantities.

Specific media and cultivation conditions depending on host cells are illustrated below, but are not limited thereto.

When the hosts are bacteria, actinomycetes, yeasts, filamentous fungi, liquid media comprising the nutrient source mentioned above are appropriate. A medium with pH 5 to 8 are preferably used.

When the host is *E. coli*, examples of preferable media are LB media, M9 media (Miller et al. Exp. Mol. Genet., Cold Spring Harbor Laboratory, p. 431 (1972)), YT medium, and so on. Using these media, cultivation can be performed usually at 14 to 43° C. for about 3 to 24 hours with aeration and stirring, if necessary.

When the host is *Bacillus*, cultivation can be performed usually at 30 to 40° C. for about 16 to 96 hours with aeration and stirring, if necessary.

When the host is yeast, an example of media is Burkholder minimal media (Bostian, Proc. Natl. Acad. Sci. USA, Vol. 77, p. 4505 (1980)). The pH of the media is preferably 5 to 8. Cultivation can be performed usually at 20 to 35° C. for about 14 to 144 hours with aeration and stirring, if necessary.

When the host is an animal cell, examples of media are MEM media containing about 5 to 20% fetal bovine serum (Science, Vol. 122, p. 501 (1952)), DMEM media (Virology, Vol. 8, p. 396 (1959)), RPMI1640 media (J. Am. Med. Assoc., Vol. 199, p. 519 (1967)), 199 media (Proc. Soc. Exp. Biol. Med., Vol. 73, p. 1 (1950)), HamF12 media, and so on. The pH of the media is preferably about 6 to 8. Cultivation can be performed usually at about 30 to 40° C. for about 15 to 72 hours with aeration and stirring, if necessary.

When the host is an insect cell, an example of media is Grace's media containing fetal bovine serum (Proc. Natl. Acad. Sci. USA, Vol. 82, p. 8404 (1985)). The pH thereof is preferably about 5 to 8. Cultivation can be performed usually at about 20 to 40° C. for 15 to 100 hours with aeration and stirring, if necessary.

An extracellular domain of the human TGF-β type II receptor (soluble human TGF-β type II receptor) of the present invention can be produced by cultivating transformants as mentioned above (in particular animal cells or *E. coli*) and allowing them to secrete the protein into the culture supernatant. Namely, a culture filtrate (supernatant) is obtained by methods, such as filtration or centrifugation of the obtained culture, and the desired protein is purified and isolated from the culture filtrate by methods commonly used in order to purify and isolate natural or synthetic proteins.

Examples of the isolation and purification methods are methods utilizing affinity, such as affinity column chromatography; methods utilizing solubility, such as salting out and solvent precipitation method; methods utilizing the difference in molecular weight, such as dialysis, ultrafiltration, gel filtration, and sodium dodecyl sulfate-polyacrylamide gel electrophoresis; methods utilizing charges, such as ion exchange chromatography and hydroxylapatite chromatography; methods utilizing the difference in hydrophobicity, such as reverse phase high performance liquid chromatography; and methods utilizing the difference in isoelectric point, such as isoelectric focusing.

When the desired protein exists in the periplasm or cytoplasm of cultured transformants, first, the cells are harvested by usual methods, such as filtration or centrifugation, and are suspended in appropriate buffer. After the cell wall and/or cell membrane of the cells and such are disrupted by methods, such as lysis with sonication, lysozyme, and freeze-thawing, the membrane fraction comprising the desired protein is obtained by methods, such as centrifugation or filtration. The membrane fraction is solubilized with a detergent, such as Triton-X100, to obtain the crude extract. Finally, the protein is isolated and purified from the crude extract by usual methods as illustrated above.

lane 1: marker molecule;
lane 2: commercially available soluble recombinant human TβRII; and
lane 3: purified soluble recombinant human TβRII prepared in the present invention.

Figure 3:
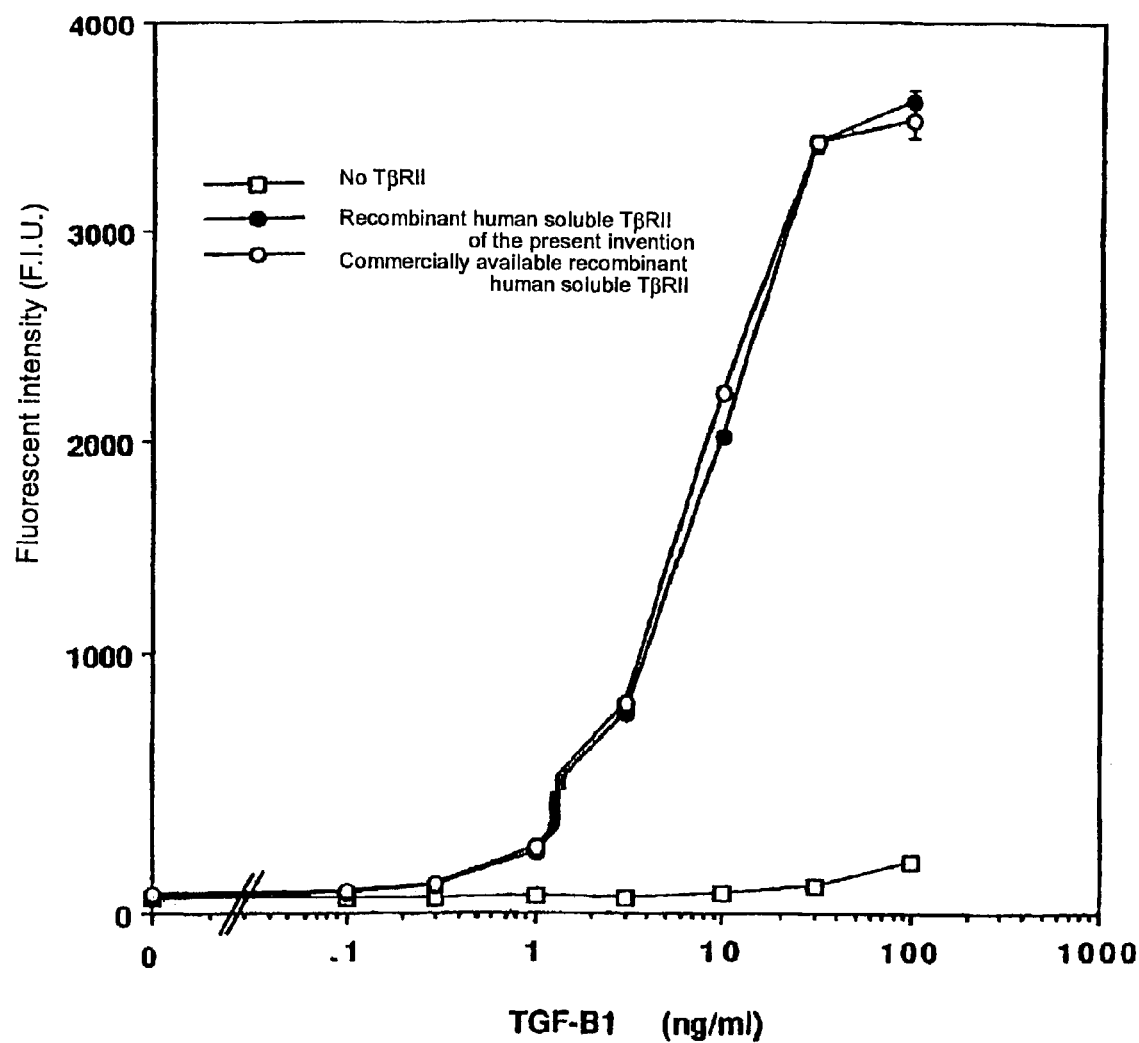

FIG. 3 depicts a graph demonstrating the binding activity of the soluble recombinant human TβRII to human TGF-β1. The ordinate indicates the fluorescent intensity, an index of the binding activity of the soluble recombinant human TβRII to human TGF-β1, and the abscissa indicates the concentration of the added human TGF-β1.

FIG. 4 depicts a table showing the profiles of various human monoclonal antibodies prepared by immunizing human antibody-producing transgenic mice with the soluble recombinant human TβRII. The circle indicate that the antibody showed the inhibitory activity with significant difference in various tests.

Figure 5:
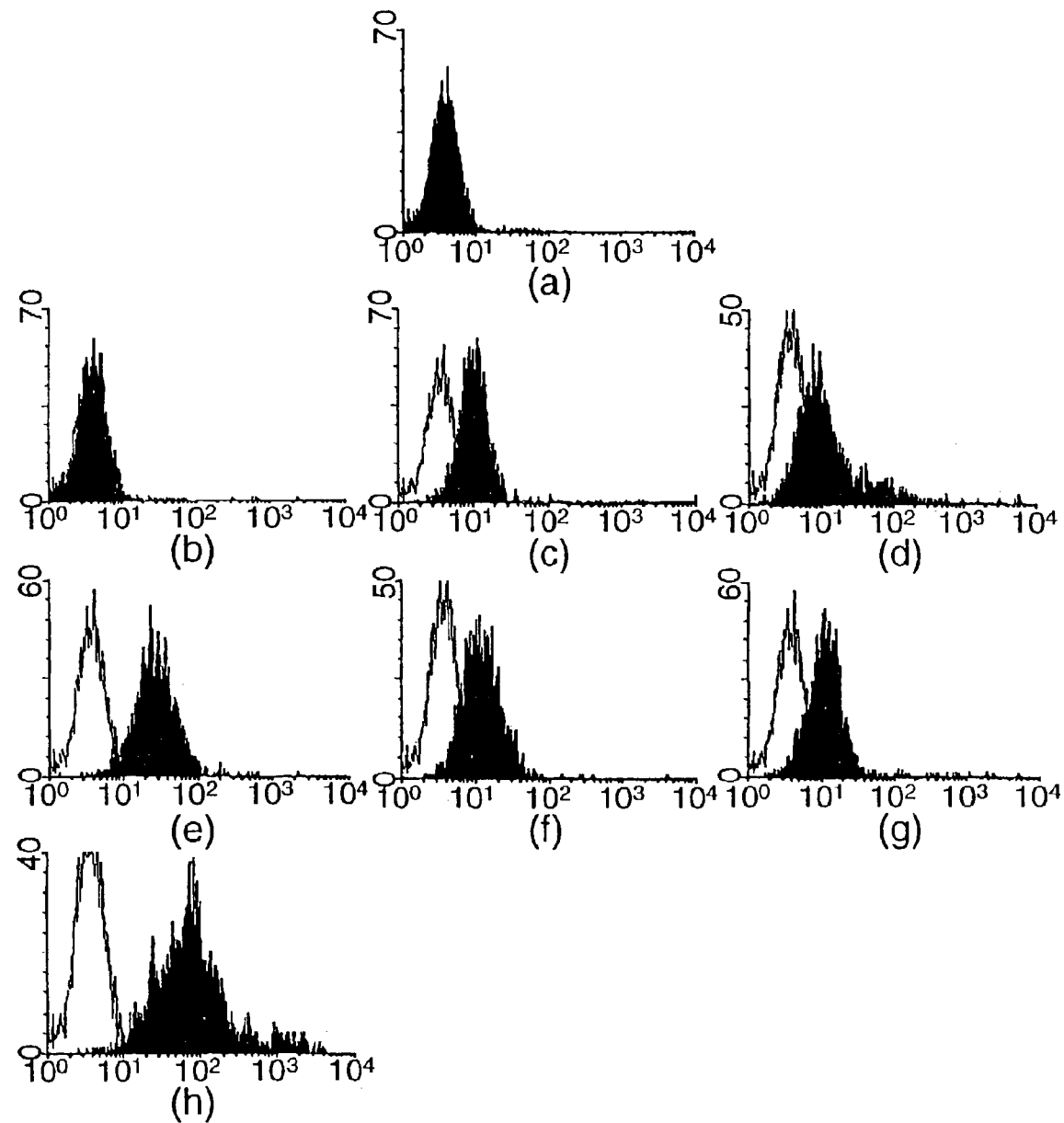

FIG. 5 depicts graphs demonstrating the reactivity (binding activity) of the human anti-human TβRII monoclonal antibodies to human lung cell line NHLF determined by a flow cytometry analysis. Panels (a) to (h) demonstrate the results of test with respective monoclonal antibodies as follows:

panel (a): streptavidin-PE alone without any primary antibody and secondary antibody;
panel (b): human anti-KLH monoclonal antibody as, the primary antibody;
panel (c): commercially available anti-human TβRII polyclonal antibody as the primary antibody;
panel (d): human anti-human TβRII monoclonal antibody TR4C175 as the primary antibody;
panel (e): human anti-human TβRII monoclonal antibody TR4D204 as the primary antibody;
panel (f): human anti-human TβRII monoclonal antibody TR4D455 as the primary antibody;
panel (g): human anti-human TβRII monoclonal antibody TR4D465 as the primary antibody; and
panel (h): human anti-human TβRII monoclonal antibody TR4B16 as the primary antibody.

Figure 6:
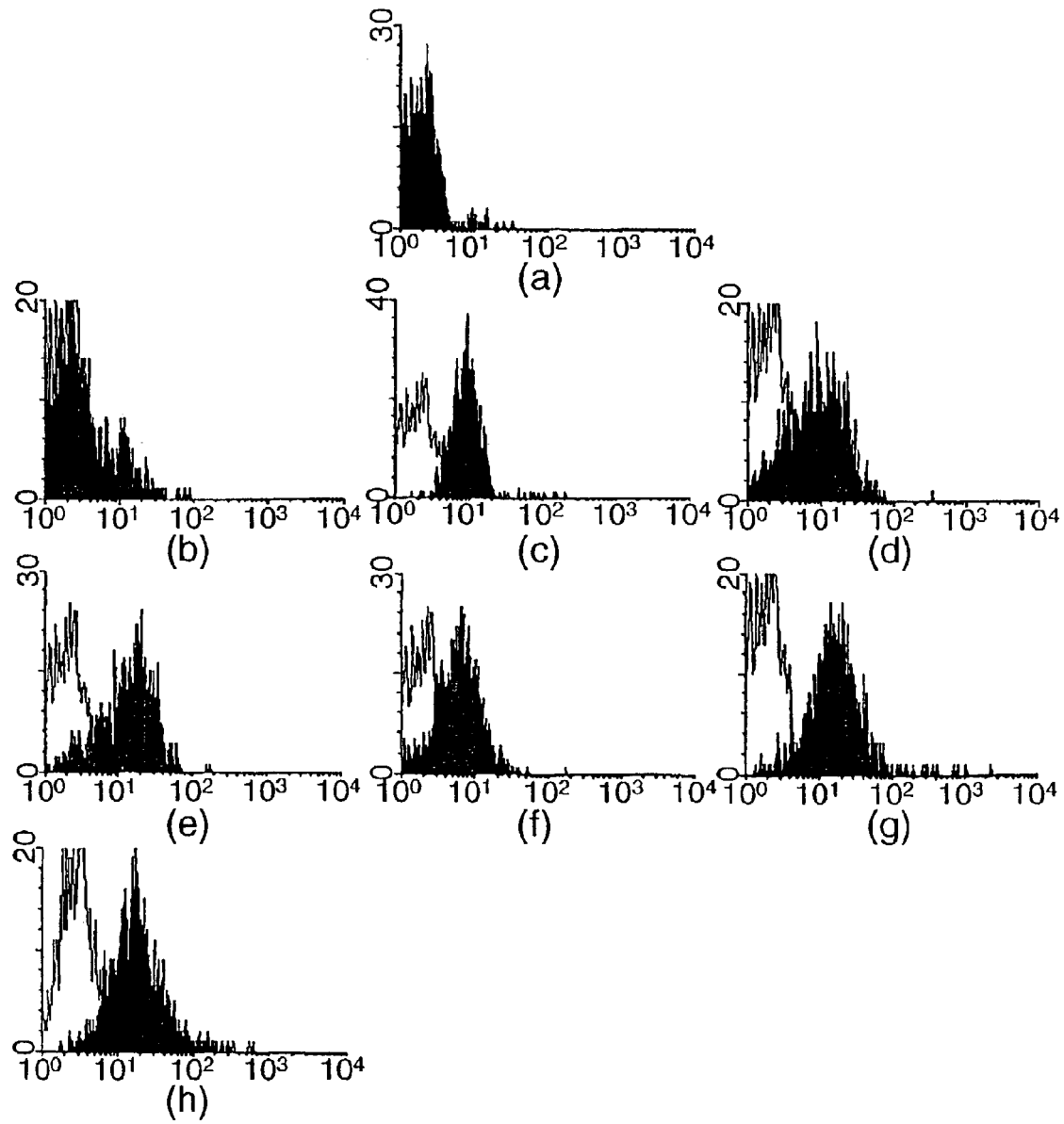

FIG. 6 depicts graphs demonstrating the reactivity (binding activity) of the human anti-human TβRII monoclonal antibodies to rat kidney-derived fibroblast cell line NRK-49F determined by a flow cytometry analysis. Panels (a) to (h) demonstrate the results of test with respective monoclonal antibodies as follows:

panel (a): streptavidin-PE alone without any primary antibody and secondary antibody;
panel (b): human anti-KLH monoclonal antibody as the primary antibody;
panel (c): commercially available anti-human TβRII polyclonal antibody as the primary antibody;
panel (d): human anti-human TβRII monoclonal antibody TR4C175 as the primary antibody;
panel (e): human anti-human TβRII monoclonal antibody TR4D204 as the primary antibody;
panel (f): human anti-human TβRII monoclonal antibody TR4D455 as the primary antibody;
panel (g): human anti-human TβRII monoclonal antibody TR4D465 as the primary antibody; and
panel (h): human anti-human TβRII monoclonal antibody TR4B16 as the primary antibody.

Figure 7:
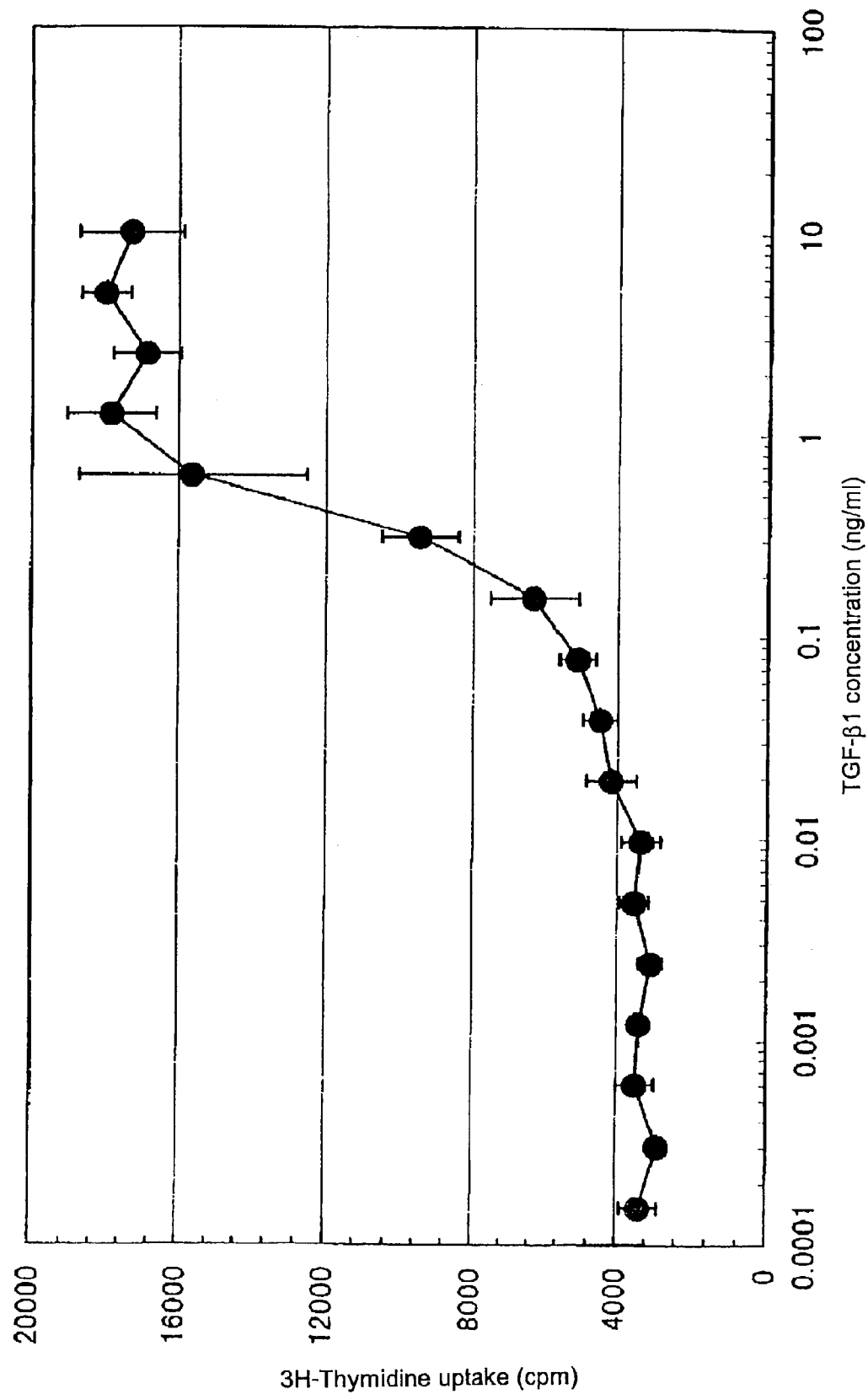

FIG. 7 depicts a graph demonstrating the dose-dependent growth-promoting activity of human TGF-β1 on human osteosarcoma cell line MG-63. The ordinate indicates the amount of [$^3$H]-thymidine uptake of the cells as an index of the degree of the cell growth-promoting activity, and the abscissa indicates the concentration (dose) of human TGF-β1.

Figure 8:
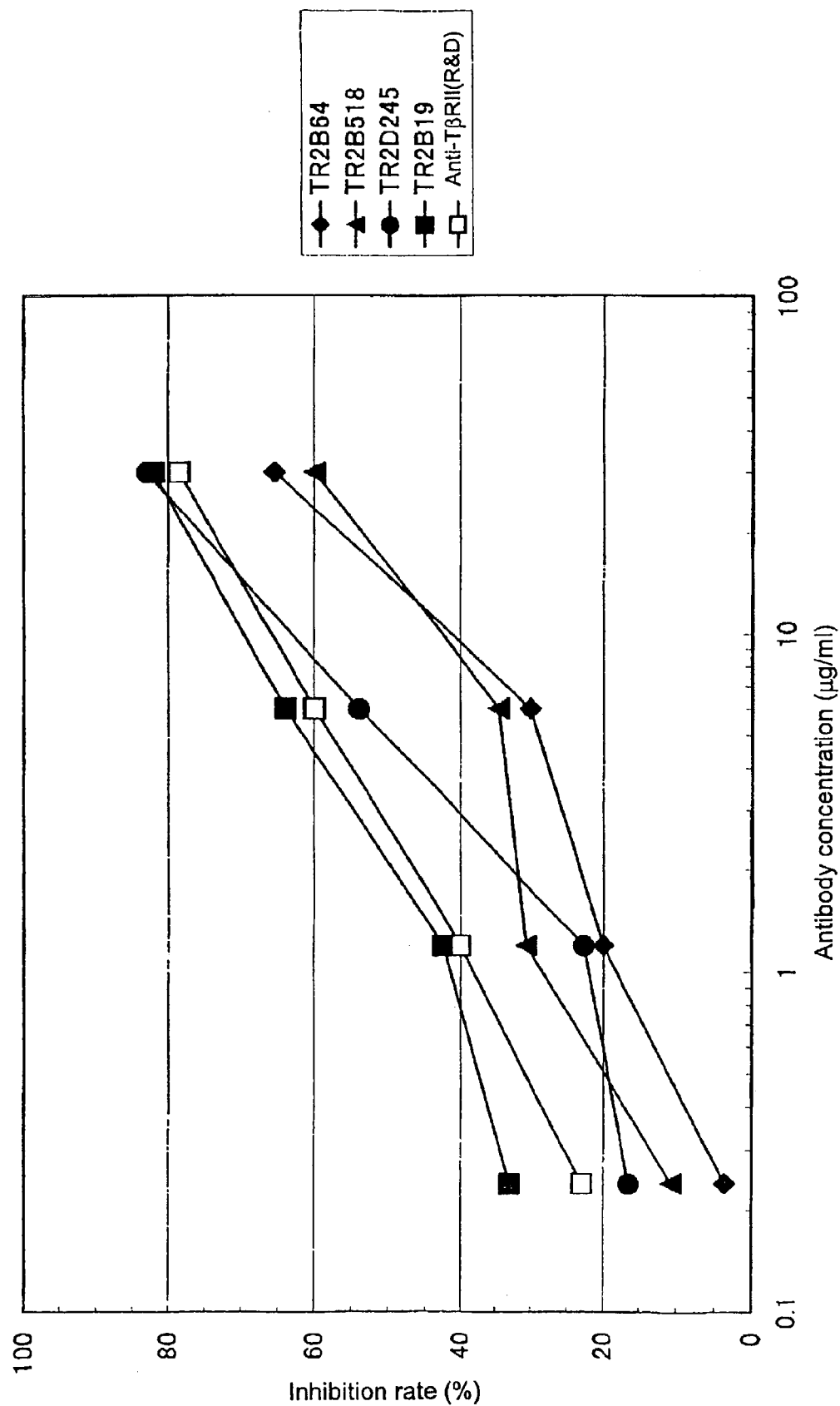

FIG. 8 depicts a graph demonstrating the inhibitory activity of the human anti-human TβRII monoclonal antibody on the cell growth of human osteosarcoma cell line MG-63, wherein the cell growth was induced by the stimulation with human TGF-β1. The ordinate indicates the cell growth inhibition rate and the abscissa indicates the antibody concentration.

Figure 9:
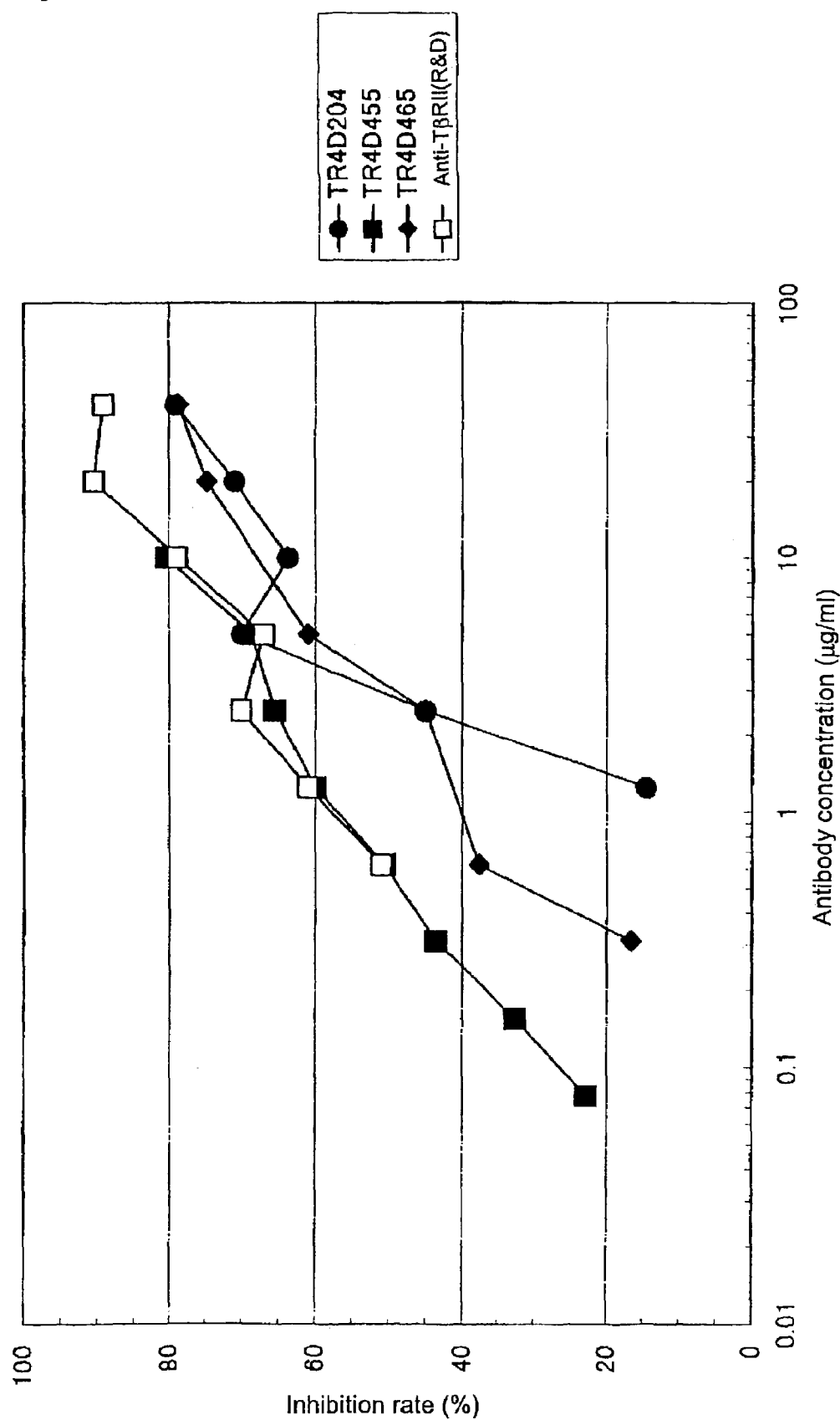

FIG. 9 depicts a graph demonstrating the inhibitory activity of the human anti-human TβRII monoclonal antibody on the cell growth of human osteosarcoma cell line MG-63, wherein the cell growth was induced by the stimulation with human TGF-β1. The ordinate indicates the cell growth inhibition rate and the abscissa indicates the antibody concentration.

Figure 10:
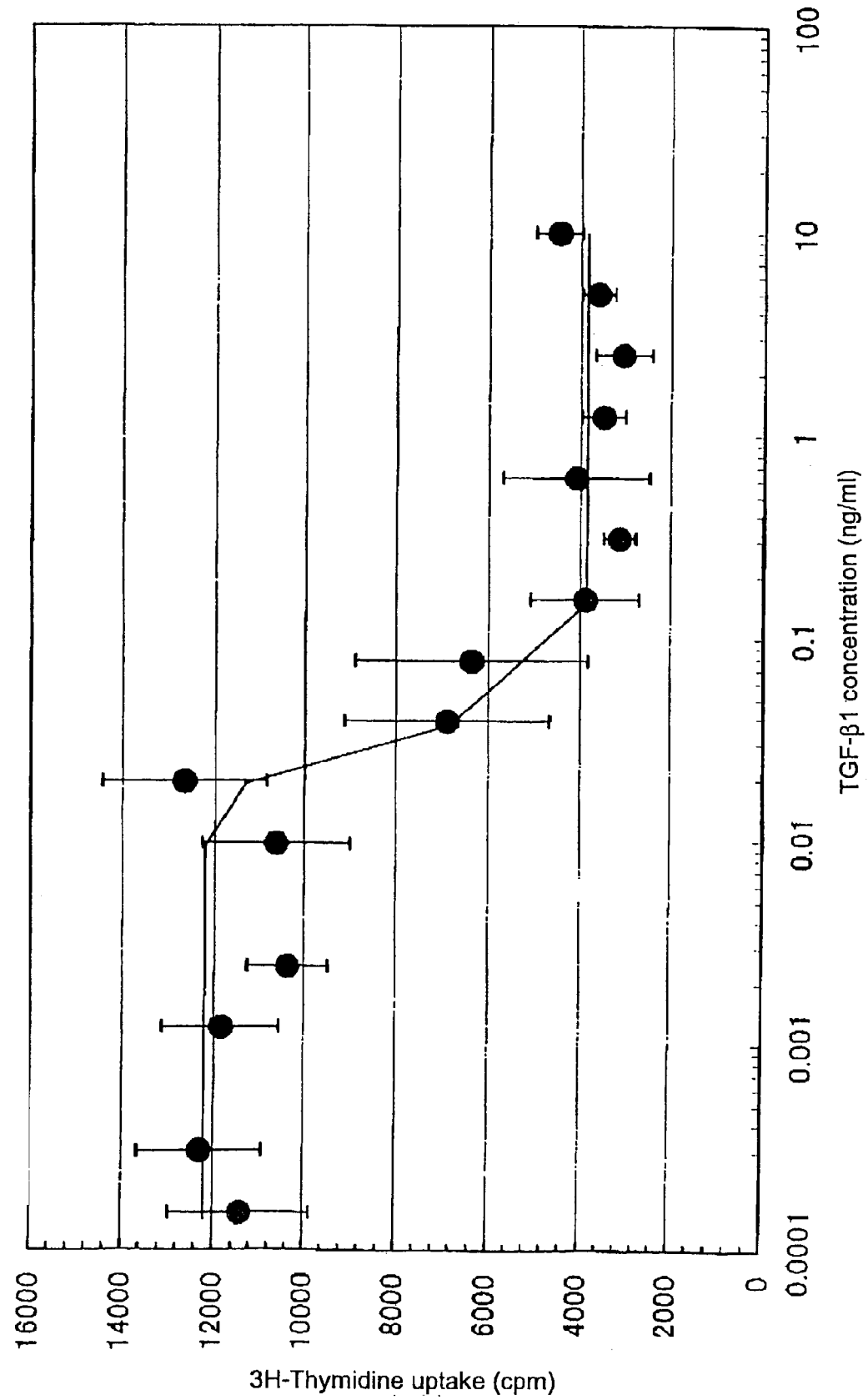

FIG. 10 depicts a graph demonstrating the dose-dependent cell growth-suppressing activity of human TGF-β1 on human lung cancer-derived cell line A-549. The ordinate indicates the amount of [$^3$H]-thymidine uptake of the cells as an index of the degree of the cell growth-promoting activity, and the abscissa indicates the concentration of human TGF-β1.

Figure 11:
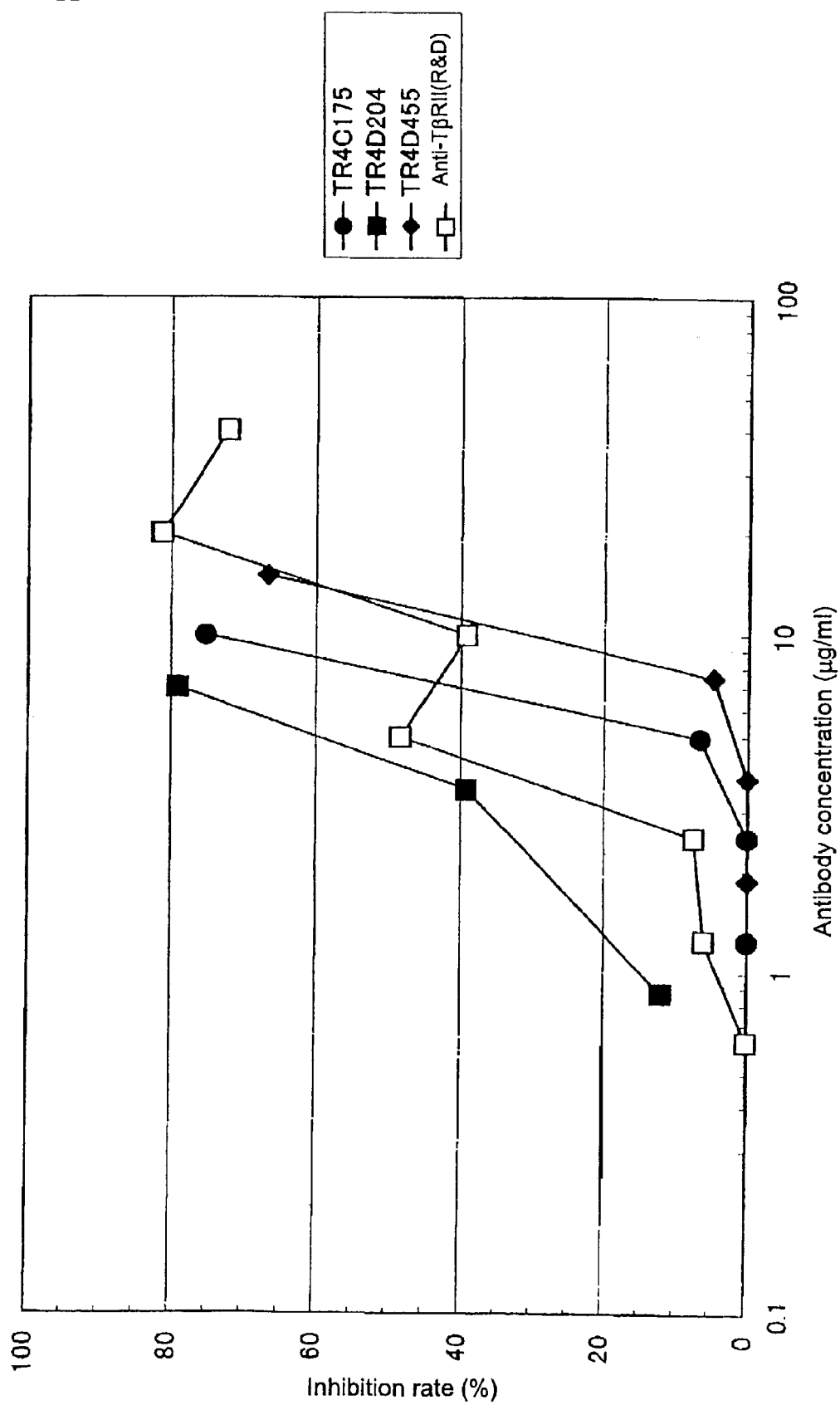

FIG. 11 depicts a graph demonstrating the inhibitory activity of the human anti-human TβRII monoclonal antibody on the human TGF-β1 stimulation-induced suppression of the cell growth of human lung cancer-derived cell line A-549. The ordinate indicates the inhibition rate on the cell growth suppression and the abscissa indicates the antibody concentration (dose).

Figure 12:
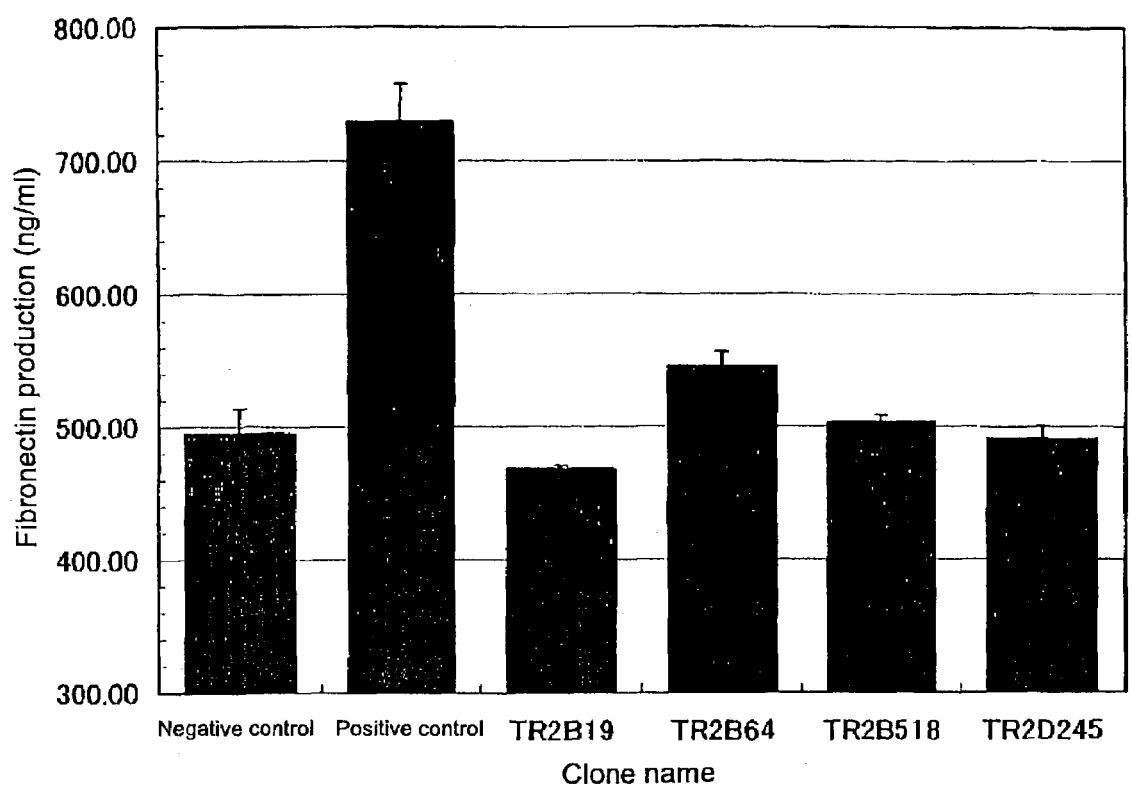

FIG. 12 depicts a graph demonstrating the inhibitory activity of the human anti-human TβRII monoclonal antibody on fibronectin production by human cells, which production is induced by the stimulation with human TGF-β1. The ordinate indicates the amount of the produced fibronectin and the abscissa indicates the type of the antibody.

Figure 13:
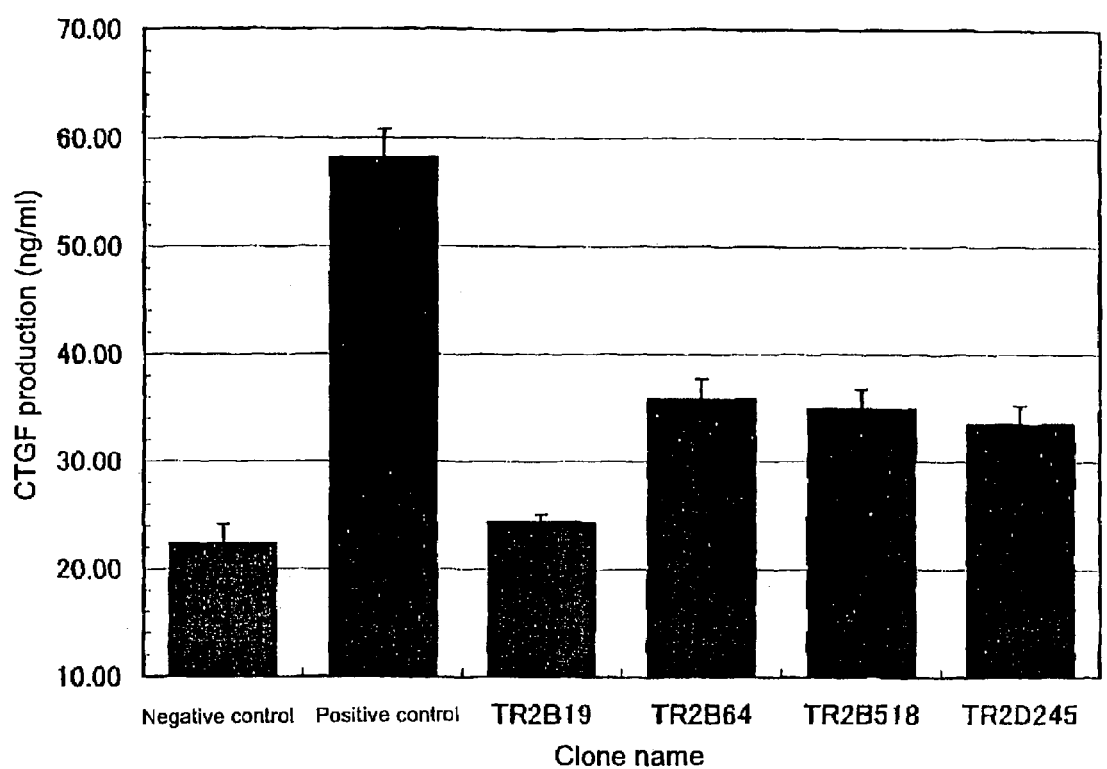

FIG. 13 depicts a graph demonstrating the inhibitory activity of the human anti-human TβRII monoclonal antibody on the production of connective tissue growth factor (CTGF) by human cells, which production is induced by the stimulation with human TGF-β1. The ordinate indicates the amount of the produced CTGF and the abscissa indicates the type of the antibody.

Figure 14:
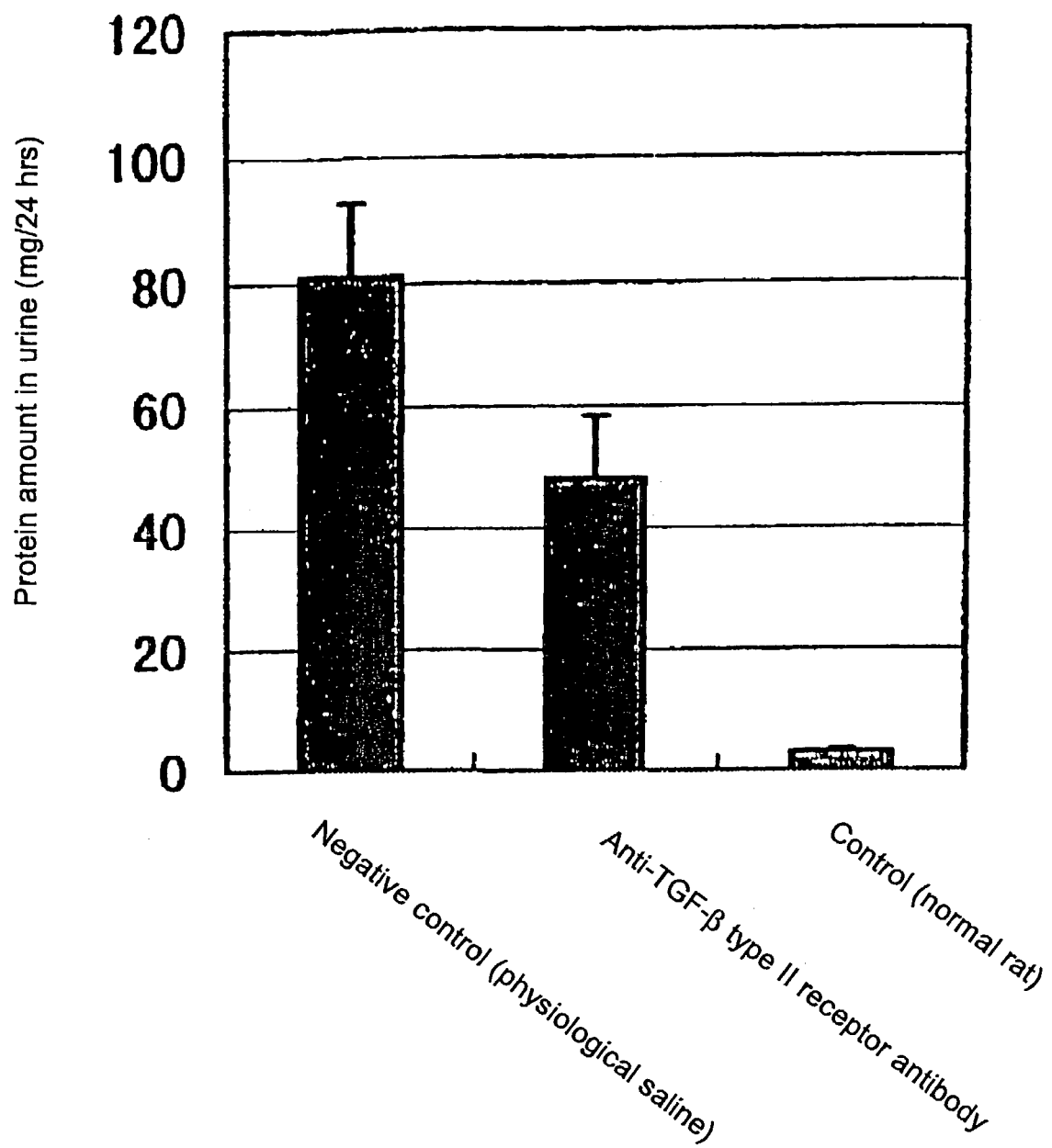

FIG. 14 depicts a graph demonstrating the suppressing effect of the TGF-β type II receptor inhibitor on the increase of protein concentration in the urine as a parameter for kidney disease in the test using a kidney disease model rat.

Figure 15:
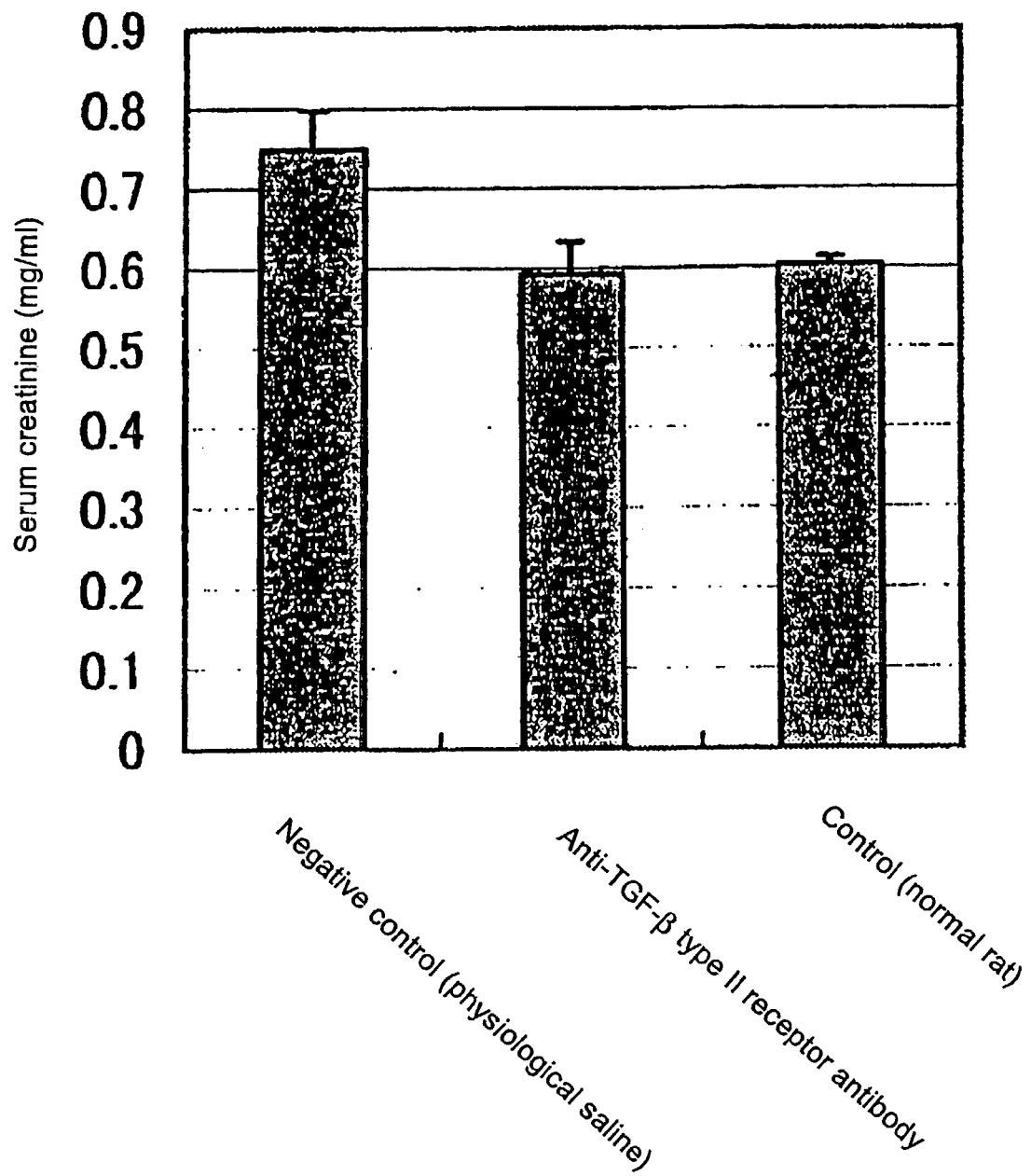

FIG. 15 depicts a graph demonstrating the suppressing effect of the TGF-β type II receptor inhibitor on the increase of serum creatinine level as a parameter for kidney disease in the test using a kidney disease model rat.

Figure 16:
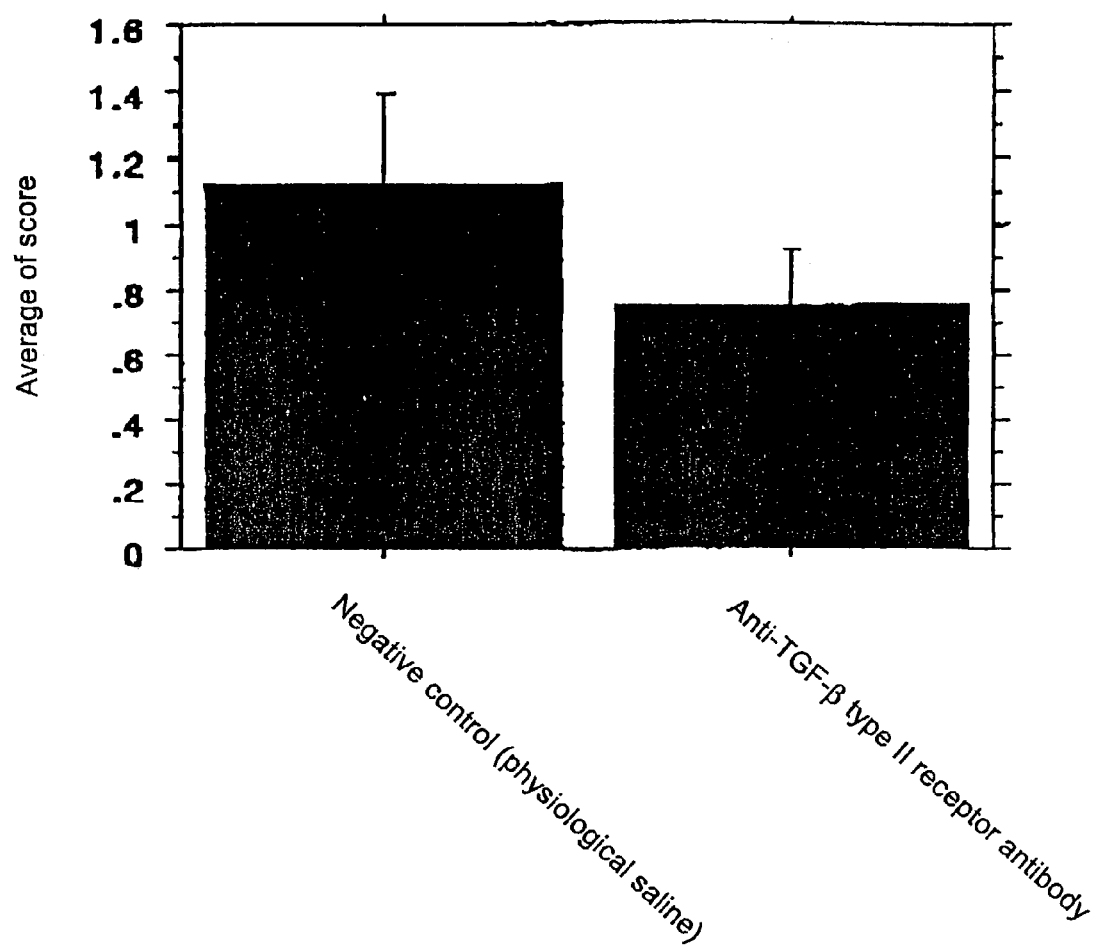

FIG. 16 depicts a graph demonstrating the suppressing effect of the TGF-β type II receptor inhibitor on the increase of the amount of fibronectin in kidney as a parameter for kidney disease in the test using a kidney disease model rat.

Figure 17:
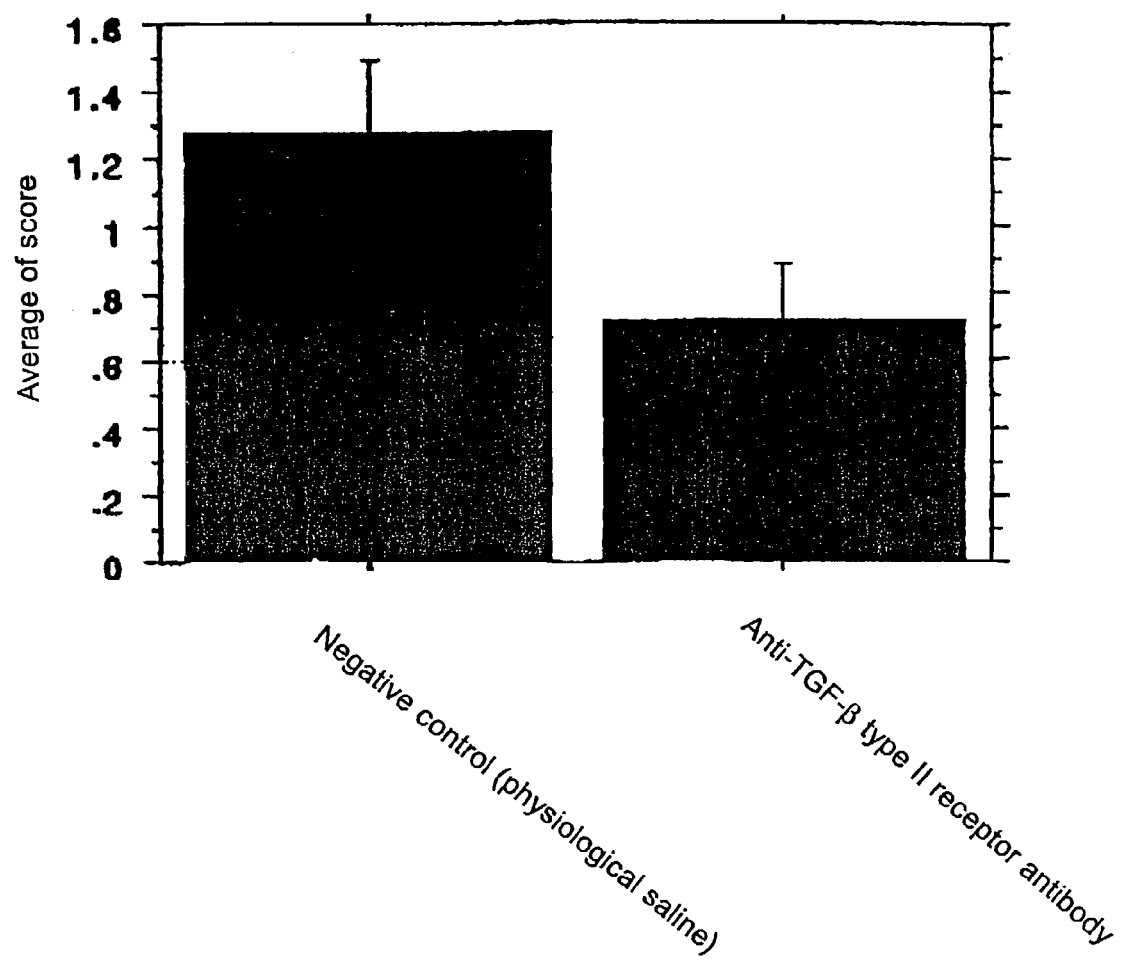

FIG. 17 depicts a graph demonstrating the suppressing effect of the TGF-β type II receptor inhibitor on the increase of the amount of type I collagen in kidney as a parameter for kidney disease in the test using a kidney disease model rat.

BEST MODE FOR CARRYING OUT THE INVENTION

The present invention is illustrated in detail below with reference to Examples, but is not to be construed as being limited thereto.

In some cases in the Examples below, "TGF-β type II receptor" is also referred to as "TβRII".

EXAMPLE 1

Establishment of a Quantitative Method with Sandwich ELISA for Human Soluble TβRII <1-1> Establishment of a Sandwich ELISA System to Quantify Soluble Recombinant Human TβRII Goat anti-human TβRII polyclonal antibody (R&D) was diluted with phosphate buffer, and added to each well of a 96-well ELISA microplate (Corning) at a concentration of 0.1 μg/50 μl/well. The plate was incubated at room temperature for one hour to allow adsorption of the polyclonal antibody.

The plate was washed with phosphate buffer, and then phosphate buffer containing 3% bovine serum albumin (BSA) was added to each well (200 μl/well). The plate was incubated at room temperature for two hours to block the antibody-free space on the well surface of the plate. Then, the plate was washed three times with phosphate buffer.

The assay sample was added to each well of the antibody-immobilized microplate (50 μl/well), and the plate was incubated at room temperature for one hour. Then, the microplate was washed three times with phosphate buffer containing 0.1% Tween20. Biotin-labeled goat anti-human TβRII polyclonal antibody (R&D) (diluted with phosphate buffer containing 1% BSA and 0.1% Tween20) was then added to each well at a concentration of 0.025 μg/50 μl/well. The plate was incubated at room temperature for one hour.

Then, the microplate was washed three times with phosphate buffer containing 0.1% Tween20. 50 μl of streptavidin-β-galactosidase (GIBCO BRL) (diluted 2000-fold with a solution containing 0.5 M NaCl and 20 mM HEPES (containing 1 mg/ml BSA, pH 7.0)) was added to each well. The plate was incubated at room temperature for 30 minutes.

After washing the microplate three times with phosphate buffer containing 0.1% Tween20, 50 μl of 1% 4-methyl-umbelliferyl-β-D-galactoside (Sigma) (diluted with a solution (containing 1 mg/ml BSA, pH 7.0) consisting of 100 mM NaCl, 1 mM MgCl$_2$, and 10 mM phosphate buffer (containing Na and K)) was added to each well. The plate was incubated at room temperature for 15 minutes.

1 M Na$_2$CO$_3$ (100 μl) was added to each well to stop the reaction. The fluorescence intensity at a wavelength of 460 nm (excitation: at 355 nm) was determined with Fluoroscan II microplate fluorometer (Labsystems Inc.). The amount of soluble recombinant human TβRII in the assay sample was determined from the calibration curve prepared in the Example described below.

<1-2> Preparation of the Calibration Curve

Figure 1:
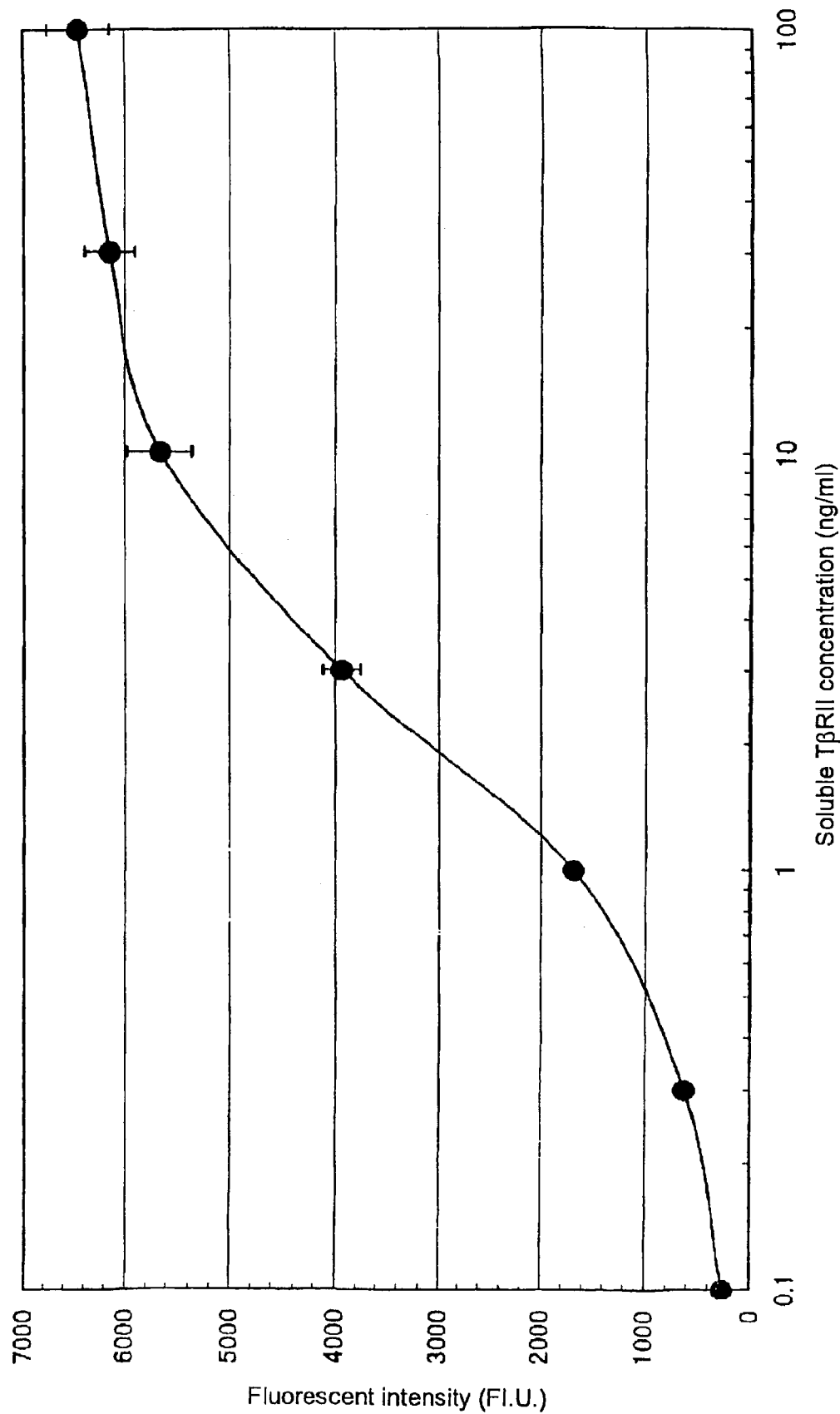
FIG. 1 depicts a calibration curve of the soluble recombinant human TβRII (standard substance) quantified by sandwich ELISA using anti-human TPII polyclonal antibodies. The ordinate indicates fluorescent intensity and the abscissa indicates the concentration of the standard substance.

A calibration curve was prepared with the sandwich ELISA established in Example <1-1> using commercially available soluble recombinant human TβRII (R&D) as a standard. The result is demonstrated in FIG. 1.

The calibration curve had significant differences within a very low concentration range of 0.1-100 ng/ml.

EXAMPLE 2

Preparation of Soluble Recombinant Human TβRII

The cDNA (SEQ ID NO: 1) encoding the extracellular domain of human TβRII (the amino acid sequence from residue 1 to residue 159; SEQ ID NO: 2) was prepared by PCR according to a conventional method.

Specifically, the cDNA was synthesized by PCR according to a conventional method using cDNA prepared from mRNA obtained from human kidney as a template, and primers designed based on human TβRII cDNA (Cell, Vol. 68, p. 775-758, 1992; GenBank Accession No: M85079).

The human TβRII cDNA so prepared containing the coding region was inserted into plasmid pEF-BOS (Unexamined Published Japanese Patent Application No. (JP-A) Hei 2-242687) to prepare an expression vector. The human kidney-derived fibroblast cell line HEK293 (ATCC CRL-1573) was transformed with the vector by electroporation. The transformed cells were cultured in the serum-free medium ASF104 (Ajinomoto) for four days to transiently express the soluble recombinant human TβRII in the cells. The expression of human soluble TβRII was verified by Western blotting using anti-human soluble TβRII polyclonal antibody (R&D).

Figure 2:
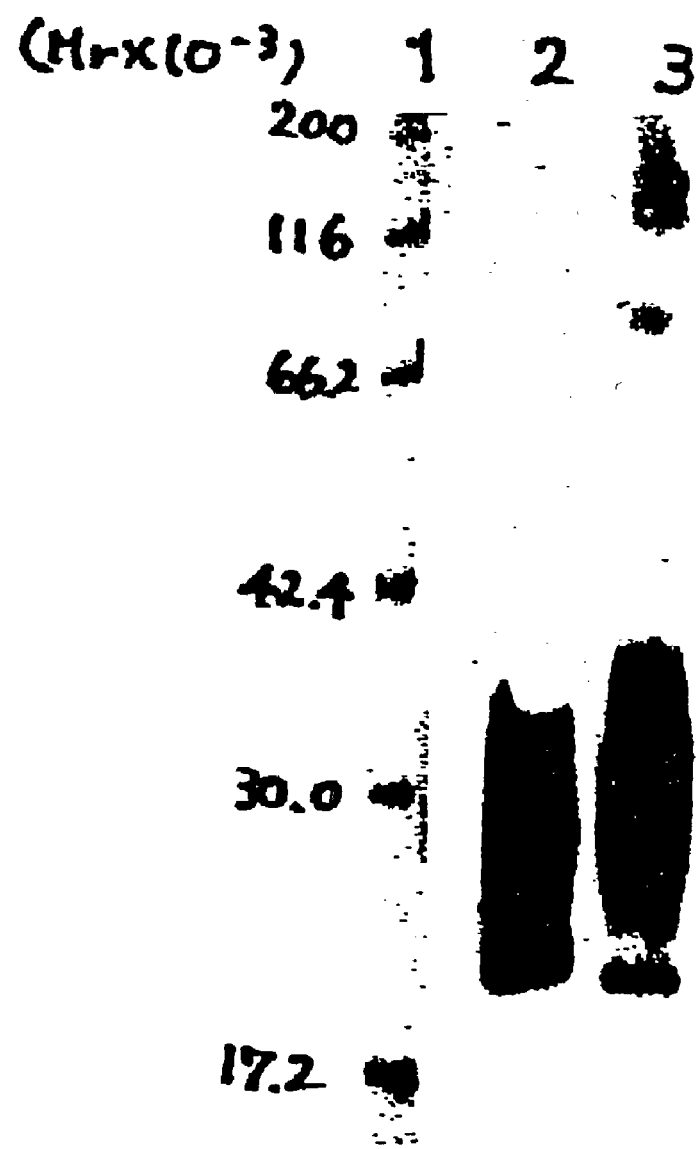
FIG. 2 depicts a electrophoretogram on SDS-polyacrylamide gel demonstrating the result of a Western blot on purified soluble recombinant human TpR11. Lanes 1 to 3 contain respective samples as follows.

The culture supernatant was recovered and concentrated, and then was subjected to column chromatography using the anti-human soluble TβRII polyclonal antibody (R&D). After the elution was washed with phosphate buffer, it was further eluted with 0.1 M glycine-HCl (pH 2.5). The eluted fraction was neutralized with 2 M Tris-HCl (pH 8.83) to obtain the purified human soluble TβRII fraction. The purity of the human soluble TβRII was confirmed by Western blotting using the anti-human soluble TβRII polyclonal antibody (R&D). The result is demonstrated in FIG. 2.

The purified human soluble TβRII was quantified by the sandwich ELISA established in Example 1.

EXAMPLE 3

Test on the Binding Activity of the Purified Human TβRII to TGF-β1

The binding activity of the purified soluble human TβRII prepared in Example 2 to human TGF-β1 was tested as follows.

The soluble recombinant human TβRII was added to each well (0.2 μg/well) of a 96-well ELISA microplate (Corning). The microplates were incubated at room temperature for two hours to adsorb the recombinant soluble human TβRII on the wells. Then, the supernatant was discarded, and a blocking reagent (200 μl; phosphate buffer containing 3% BSA) was added to each well. The plate was incubated at room temperature for two hours to block the TβRII-free space on the well surface of the plate. Each well was washed three times with phosphate buffer containing 0.1% Tween20 (200 μl). Thus, microplates of which wells have been coated with soluble recombinant human TβRII were prepared.

The human TGF-β1 (R&D) was added to each well at various concentrations (100, 50, 25, 12.5, 6.3, and 3.1 ng/ml), and then the plate was incubated for one hour. Each well was washed three times with phosphate buffer containing 0.1% Tween20 (200 μl).

A biotin-labeled goat anti-human TGF-β1 antibody (50 μl; R&D) was added to the plate, and then the plate was incubated at room temperature for one hour.

After the microplate was washed with phosphate buffer containing 0.1% Tween20, a streptavidin-β-galactosidase (50 μl; GIBCO BRL (diluted 2000-fold with a solution containing 0.5 M NaCl, 20 mM HEPES, and 1 mg/ml BSA (pH 7.0))) was added to each well. The plate was incubated at room temperature for 30 minutes.

Then, the microplate was washed with phosphate buffer containing 0.1% Tween20. 50 μl of 1% 4-methyl-umbelliferyl-β-D-galactoside (Sigma) (diluted with a solution (pH 7.0) containing 100 mM NaCl, 1 mM $MgCl_2$, 10 mM phosphate buffer, and 1 mg/ml BSA) was added to each well. The plate was incubated at room temperature for ten minutes. 1 M $Na_2CO_3$ (100 μl) was added to each well to stop the reaction.

The fluorescence intensity at a wavelength of 460 nm (excitation: at 355 nm) was determined with Fluoroscan II microplate fluorometer (Labsystems Inc.).

A positive control experiment was carried out by the same method as described above using a commercially available soluble recombinant human TβRII (R&D). A negative control experiment was carried out by the same method as described above in the absence of any human soluble TβRII (R&D).

The result is shown in FIG. 3, demonstrating that the purified soluble recombinant human TβRII exhibits a concentration-dependent binding activity toward human TGF-β1.

EXAMPLE 4

Preparation of Hybridomas Producing Human Anti-Human TβRII Monoclonal Antibody

Preparation of the Monoclonal Antibodies in this Example was performed by a conventional method described in "Experimental Medicine (supplement): Handbook for Cellular Engineering Technology, eds., T. Kuroki et al., Yodosha, page 66-74, 1992)", and "Introductory Manual for Monoclonal Antibody Experiment (T. Ando et al., Kodansha, 1991)".

The purified soluble recombinant human TβRII prepared in Example 2 was used as the human TβRII immunogen.

The human antibody-producing transgenic mouse, which had been produced by the above-mentioned method was used as the animal to be immunized (Nature Genetics, Vol. 7, p. 13-21, 1994; Nature Genetics, Vol. 15, p. 146-156, 1997; Published Japanese Translation of International Publication No. Hei 4-504365; Published Japanese Translation of International Publication No. Hei 7-509137; NIKKEI SCIENCE, June issue, pp 40-50, 1995).

The cells were cultured in multi-well microplates.

<4-1> Preparation of Hybridomas Producing Human Anti-Human TβRII Monoclonal Antibody For primary immunization (day 0), the soluble recombinant human TβRII prepared in Example 2 together with Freund's complete adjuvant (ICN/CAPPEL) was injected into the footpads of the above-mentioned human antibody-producing transgenic mice (6 μg/animal). The soluble recombinant human TβRII together with Freund's incomplete adjuvant (ICN/CAPPEL) was given to the mice by footpad injection every week after the primary immunization. The booster immunization was performed three times or more in total. Further, the final immunization was carried out only with the soluble recombinant human TβRII by the same procedure two days before the collection of lymph node cells described hereinafter.

The lymph node cells collected from each animal and mouse myeloma cells P3/X63-AG8.653 (ATCC No: CRL-1580) were mixed at a ratio of 5:1. Many hybridomas were prepared by cell fusion using polyethylene glycol 4000 or polyethylene glycol 1500 (GIBCO BRL) as a fusing agent.

Hybridoma selection was carried out by culturing the fused cells in ASF104 medium (Ajinomoto) containing HAT supplemented with 10% FBS and aminopterin.

<4-2> Screening of Hybridomas Producing Monoclonal Antibodies by ELISA

The hybridomas prepared in Example 2 were screened for hybridomas producing human anti-human TβRII monoclonal antibodies by ELISA as described below.

The purified soluble recombinant human TβRII prepared in Example 2 was added to each well of a 96-well ELISA microplate (Corning) (0.2 μg/well). The plate was incubated at room temperature for two hours to adsorb the recombinant soluble human TβRII.

Then, the supernatant was discarded, and a blocking reagent (200 μl; phosphate buffer containing 3% BSA)) was added to each well. The plate was incubated at room temperature for two hours to block spaces of the well surface of the plate where the soluble recombinant human TβRII has not been coated. Each well was washed three times with phosphate buffer (200 μl) containing 0.1% Tween 20. Thus, microplates that have been coated with soluble recombinant human TβRII were prepared.

The supernatant of each hybridoma culture (100 μl) was added to each well, and then the plate was incubated for two hours. Each well was washed three times with phosphate buffer (200 μl) containing 0.1% Tween20.

Then, a peroxidase-labeled goat anti-human immunoglobulin (Fc) antibody (50 μl, American Qualex International Inc.) was added to each well, and the plate was incubated at room temperature for one hour.

After the microplate was washed with phosphate buffer containing 0.1% Tween20, tetramethylbenzidine (3,3',5,5'-tetramethylbenzidine (TMB); 100 μl; BioRad) was added to each well. The plate was incubated at room temperature for 15 minutes.

Then, 2 $NH_2SO_4$ (25 μl) was added to each well to stop the reaction. The absorbance at a wavelength of 450 nm was measured with Model 3550 Microplate Reader (BioRad).

Hybridomas producing human anti-human TβRII monoclonal antibodies were thus selected.

EXAMPLE 5

Preparation of Human Anti-Human TβRII Monoclonal Antibodies

<5-1> Preparation of Human Anti-Human TβRII Monoclonal Antibodies (Method 1)

The respective clones of hybridomas described above were cultured in flasks containing ASF104 medium (Ajinomoto) supplemented. with 10% Ultra Low Bovine IgG FBS (GIBCO-BRL). After the culture for 10 to 20-days, the supernatant of each hybridoma culture was collected.

The supernatant of each hybridoma culture (100 ml) was centrifuged (at 3,000 rpm for ten minutes). A solution (pH 7.6) consisting of 20 mM $KH_2PO_4$, 180 mM $Na_2HPO_4$, and 154 mM NaCl (1/10 volume for the supernatant) was added to the supernatant obtained by centrifugation.

Then, Protein A gel (Protein A Sepharose 4 Fast Flow; Amersham Pharmacia) was added to each sample of the supernatants obtained by centrifugation, and the mixture was incubated overnight with stirring. The mixture was then centrifuged (at 3,000 rpm for ten minutes) and the supernatant was discarded. A solution (pH 2.0 to 3.0) consisting of 100 mM citric acid and 150 mM NaCl was added to the Protein A gel to elute the antibody from the gel.

Each elution was centrifuged (at 3,000 rpm for ten minutes). The recovered supernatant was neutralized by adding a solution (pH 8.7) containing 500 mM $Na_2HPO_4$ and 50 mM $KH_2PO_4$ and filtered with a filter (Millipore) to remove white precipitation. The filtrate obtained was dialyzed against phosphate buffer (overnight). Thus, the human anti-human TβRII monoclonal antibodies were purified.

<5-2> Preparation of Human Anti-Human TβRII Monoclonal Antibodies (Method 2)

Each of the above-mentioned hybridoma clones (1 to $2\times10^6$ cell/ml each) conditioned in ASF104 medium (Ajinomoto) containing 10% Ultra Low Bovine IgG FBS (GIBCO-BRL) was plated and cultured in Integra Cell Line 1000 (INTEGRA CL1000, Integra Bioscience). After 7 to 10-days culture, when the density of culture cells reached about $1\times10^8$ cells/ml, the supernatant of each hybridoma culture was recovered.

Then, hybridoma cultures were centrifuged (at 3,000 rpm for ten minutes) and each of the obtained supernatants was loaded onto HiTrap Protein G Column (HiTrap affinity column Protein G; Amersham Pharmacia). Then, the column was washed with phosphate buffer, and a solution (pH 2.0) consisting of 100 mM citric acid and 150 mM NaCl was loaded onto the Protein G column to elute the antibody. The elution was neutralized by adding a solution (pH 9.0) containing 750 mM Tris-HCl, and then filtered with a filter (Millipore) to remove white precipitation. The obtained filtrate was dialyzed against phosphate buffer (overnight), and filtered with a filter (Millipore). Thus, the human anti-human TβRII monoclonal antibodies were purified.

EXAMPLE 6

Determination of the Isotype of the Monoclonal Antibodies

Determination of the isotype of the respective human anti-human TβRII monoclonal antibodies purified in Example 5 was carried out with human monoclonal antibody isotyping kit (American Qualex). The experiment was carried out according to the protocol attached to the kit.

It was demonstrated that the human anti-human TβRII monoclonal antibodies are IgG2/κ or IgG4/κ (FIG. 4).

The human anti-human TβRII monoclonal antibody producing hybridomas prepared as described above were named with the symbols as indicated below. The numeral immediately after TR in the symbol represents the isotype of the human anti-human TβRII monoclonal antibody produced by the hybridoma. When the numeral is "2", then the isotype is IgG2/κ; when it is "4", the isotype is IgG4/κ (FIG. 4).

<Hybridoma Clones Producing Human IgG2/κ Monoclonal Antibody>

TR2B19, TR2B64, TR2B209, TR2B518, TR2D245, and TR2D249

<Hybridoma Clones Producing Human IgG4/κ Monoclonal Antibody>

TR4B16, TR4C175, TR4D204, TR4D455, and TR4D465

The clone names as listed above are used in all the Examples hereinafter including this Example, as well as the figures and tables showing the test results obtained in the Examples.

EXAMPLE 7

Reactivity to Human TβRII and Crossreactivity to Rat TβRII

The various human anti-human TβRII monoclonal antibodies prepared as described above were analyzed by cell staining (by flow cytometry) for their reactivity against human TβRII using human lung cell line NHLF (Takara Shuzo; catalog No. CC-2512) expressing human TβRII on cell surface.

Further, similarly, the reactivity against rat TβRII of each of the various human anti-human TβRII monoclonal antibodies was analyzed by cell staining (by flow cytometry) using rat kidney-derived fibroblast cell line NRK-49F (ATCC CRL-1570) expressing rat TβRII on cell surface.

The respective cells cultured in flasks were harvested gently under a mild condition using phosphate buffer containing 10 mM EDTA and 0.1% BSA.

Each of the human anti-human TβRII monoclonal antibodies of the present invention or commercially available goat anti-human TβRII polyclonal antibody (R&D) (300 μl, 5 μg/ml) (diluted with phosphate buffer containing 0.1% BSA) was added to the respective cells (1 to $2 \times 10^4$ cells). The mixtures were incubated at 4° C. for one hour, and then centrifuged (at 1,500 rpm for three minutes). The supernatants were discarded, and the cells were washed twice with phosphate buffer. The biotin-labeled anti-human immunoglobulin (Fc) antibody (200 μl; American Qualex International Inc.) was added to the samples containing the human antibodies. The biotin-labeled anti-goat immunoglobulin antibody (200 μl; Amersham Pharmacia) was added to the samples containing the goat antibody. The samples were incubated at 4° C. for one hour.

Then, each sample was centrifuged (at 1,500 rpm for three minutes), and the supernatant was discarded. The cells were washed twice with phosphate buffer. Then, phycoerythrin (PE)-labeled streptavidin (200 μl; Becton Dickinson) (diluted with phosphate buffer containing 0.1% BSA) was added to the cells, and the cells were incubated at 4° C. for 30 minutes. The cells were then centrifuged (at 1,500 rpm for three minutes) and the supernatant was discarded. The cells were washed three times with phosphate buffer, and phosphate buffer (300 μl) was added thereto. The samples were fluorescently analyzed with FACStar fluorescence-activated cell sorter (Becton Dickinson) (fluorescence wavelength: a DF585/42 filter, excitation wavelength: 488 nm).

A negative control test was carried out by the same method as described above using anti-KLH human monoclonal antibody prepared by immunizing the human antibody-producing transgenic mouse described above with KLH (keyhole limpet hemocyanin; PIERCE).

The reactivity against human lung cell line NHLF is depicted in FIG. 5. The reactivity against rat kidney-derived fibroblast cell line NRK-49F is depicted in FIG. 6.

The monoclonal antibodies of the present invention were demonstrated to significantly react to the human TβRII and also have crossreactivity to rat TβRII.

EXAMPLE 8

The Inhibitory Activity of the Human Anti-Human TβRII Monoclonal Antibody on Cell Growth Induced by Stimulation with TGF-β

The TGF-β cell growth-promoting activity depends on the type of the cell. For example, the factor acts as a growth-suppressing factor rather than as a growth-promoting factor on a variety of cells including epithelial cells, vascular endothelial cells, and hemocytes, but enhances the growth of mesangial cells of various tissues, such as fibroblast cells and vascular smooth muscle cells (Roberts et al, The transforming growth factor-βs, In Peptide Growth Factors and Their Receptors, Part I, ed. by Sporn, M. B. & Roberts, A. B., Springer-Verlag, Berlin, 1990, p. 419-472).

According to the test, the inhibitory effects of the human anti-human TβRII monoclonal antibodies of the present invention on cell growth induced by the stimulation with TGF-β were analyzed as follows:

<8-1> Cell Growth-Promoting Activity of TGF-β1

Cells of human osteosarcoma cell line MG-63 (ATCC CRL-1427; $5 \times 10^3$ cells/well) were plated in a 96-well microtiter plate, and cultured at 37° C. for one day. Then, each well wherein the cells had been plated was washed twice with MEM Earle's salt medium (100 μl, GIBCO BRL) containing 0.1% FBS. Human TGF-β1, which had been diluted to various concentrations (R&D; conc., 0.0001525 to 10 ng/ml), was added to the wells, and the plate was incubated at 37° C. for 40 hours.

Then, [$^3$H]-thymidine was added to each well (1 μCi/well) and the cells were further incubated at 37° C. for six hours. The cells were harvested using MicroMate 196 cell harvester (PACKARD), and the amount of [$^3$H]-thymidine uptake of the cells was measured with Matrix 9600M (PACKARD).

A negative control test was carried out by the same method as described above in the absence of TGF-β1.

The result is depicted in FIG. 7.

The cells of human osteosarcoma cell line MG-63 (ATCC CRL-1427) were shown to grow in a TGF-β1 concentration dependent manner.

<8-2> The Inhibitory Activity of the Human Anti-Human TβRII Monoclonal Antibody on TGF-β-Induced Cell Growth Cells of human osteosarcoma cell line MG-63 (ATCC CRL-1427; $5 \times 10^3$ cells/well) were plated in a 96-well microtiter plate, and cultured at 37° C. for one day. Then, each well wherein the cells had been plated was washed twice with MEM Earle's salt medium (100 μl) containing 0.1% FBS. The human anti-human TβRII monoclonal antibody of the present invention or commercially available anti-human TβRII polyclonal antibody (R&D), which had been diluted to various concentrations (concentration: 0.078125 to 40 μg/ml), was then added to the wells, and the plates were pre-incubated at 37° C. for two hours.

Then, human TGF-β1 (final concentration: 0.3 ng/ml; R&D) was added to the plate, and the cells were cultured at 37° C. for 40 hours. [$^3$H]-thymidine was then added to each well (1 μCi/well), and further cultured at 37° C. for six hours. The cells were harvested using MicroMate 196 cell harvester (PACKARD), and the amount of [$^3$H]-thymidine uptake of the cells was measured with Matrix 9600M (PACKARD).

A positive control test was carried out by the same method as described above in the absence of any antibody. Further, a negative control test was carried out by the same method as described above in the absence of human TGF-β1 and any antibody. The results are depicted in FIG. 8 and FIG. 9.

FIG. 4 also demonstrates the result obtained by this test (in multiple experiments). Herein, the presence or absence of inhibitory activity of the human anti-human TβRII monoclonal antibodies of the present invention on TGF-β1-induced cell growth is simply represented with symbols.

The human anti-human TβRII monoclonal antibodies of the present invention were demonstrated to significantly inhibit the growth of human fibroblast-like cells induced by the stimulation with TGF-β.

EXAMPLE 9

The Inhibitory Activity of the Human Anti-Human TβRII Monoclonal Antibodies on the Suppression of TGF-β-Stimulated Cell Growth As described above, TGF-β has the activity to promote the growth of mesangial cells, such as fibroblast cells and vascular smooth muscle cells, in various tissue, but on the other hand, it also suppresses the growth of various cells, for example, epithelial cells, vascular endothelial cells, and hemocytes.

According to this test, the inhibitory effects of the human anti-human TβRII monoclonal antibodies of the present invention on TGF-β-induced suppression of cell growth were analyzed as follows.

<9-1> The Cell Growth-Suppressing Activity of TGF-β1

Cells of human lung cancer cell line A549 (ATCC CCL-185, 5×10³ cells/well) were plated in a 96-well microtiter plate, and cultured for one day. Then, each well wherein the cells had been plated was washed twice with a D-MEM medium containing 0.1% FBS (100 µl). Human TGF-β1, which had been diluted to various concentrations (R&D; concentration: 0.0001525 to 10 ng/ml), was added to the wells, and the plate was incubated for 40 hours.

Then, [³H]-thymidine was added to each well (1 µCi/well) and the cells were further incubated at 37° C. for six hours. The cells were harvested using MicroMate 196 cell harvester (PACKARD), and the amount of [³H]-thymidine uptake of the cells was measured with Matrix 9600M (PACKARD).

A negative control test was carried out by the same method as described above in the absence of TGF-β1. The result is depicted in FIG. 10.

Cell growth of human lung cancer cell line A-549 (ATCC CCL-185) were demonstrated to be suppressed depending on the concentration of TGF-β1.

<9-2> The Inhibitory Activity of the Human Anti-Human TβRII Monoclonal Antibodies on TGF-β-Induced Suppression of Cell Growth Cells of human lung cancer cell line A-549 (ATCC CCL-185, 5×10³ cells/well) were plated in a 96-well microtiter plate, and cultured for one day. Then, each well wherein the cells had been plated was washed twice with D-MEM medium containing 0.1% FBS (100 µl)

Each of the human anti-human TβRII monoclonal antibodies of the present invention or commercially available anti-human TβRII polyclonal antibody (R&D) (diluted to various concentrations (concentration: 0.625 to 40 µg/ml)) was added to each well, and the plate was pre-incubated at 37° C. for two hours.

Then, human TGF-β1 (final concentration: 0.1 ng/ml; R&D) was added to the plate, and the cells were cultured at 37° C. for 40 hours. [³H]-thymidine was then added to each well (1 µCi/well), and the cells were further cultured for six hours. The cells were harvested using MicroMate 196 cell harvester (PACKARD), and the amount of [³H]-thymidine uptake of the cells was measured with Matrix 9600M (PACKARD).

A positive control test was carried out by the same method as described above in the absence of any antibody. Further, a negative control test was carried out by the same method as described above in the absence of human TGF-β1 and any antibody. The result is depicted in FIG. 11.

FIG. 4 also demonstrates the result obtained by this test (in multiple experiments), in which the presence or absence of inhibitory activity of the human anti-human TβRII monoclonal antibodies of the present invention on the TGF-β1-induced suppression of cell growth is simply represented by symbols.

The human anti-human TβRII monoclonal antibodies of the present invention were demonstrated to significantly inhibit the TGF-β stimulation-induced growth suppression of human epithelial cells.

EXAMPLE 10

The Inhibitory Activity of the Human Anti-Human TβRII Monoclonal Antibodies on the Enhancement of Production of Extracellular Matrix and Cell Growth Factors Induced by the Stimulation with TGF-β

TGF-β not only regulates cell growth but also enhances production of extracellular matrix (ECM), such as collagen, fibronectin, and tenascin (Adv. Immunol., Vol. 55, p. 181, 1994 and Seminars in Cell Biol., Vol. 5, p. 389, 1994).

In addition, TGF-β not only enhances the production of ECM but also enhances production of cytokines and cell growth factors, such as FGF (fibroblast growth factor), TNF (tumor necrosis factor), IL-1 (interleukin-1), platelet-derived growth factor (PDGF), and connective tissue growth factor (CTGF; also called Hcs24; J. Cell Biology, Vol. 114, No. 6, p. 1285-1294, 1991; Int. J. Biochem. Cell Biol., Vol. 29, No. 1, p. 153-161, 1997; Circulation, Vol. 95, No. 4, p. 831-839, 1997; Cell Growth Differ., Vol. 7, No. 4, p. 469-480, 1996; J. Invest. Dermatol., Vol. 106, No. 4, p. 729-733, 1996; J. Invest. Dermatol., Vol. 105, No. 2, p. 280-284, 1995; J. Invest. Dermatol., Vol. 105, No. 1, p. 128-132, 1995).

According to this test, the inhibitory effects of the human anti-human TβRII monoclonal antibodies of the present invention on TGF-β stimulation-induced production of extracellular matrix and cell growth factors in fibroblast-like cells was analyzed as follows.

Cells of human osteosarcoma cellineMG-63 (ATCCCRL-1427, 1×10⁴ cells/well) were plated in a 96-well microtiter plate, and cultured for one day. Then, each well wherein the cells had been plated was washed twice with MEM Earle's salt medium containing 0.1% FBS (100 µl). MEM Earle's salt medium containing 0.1% FBS (100 µl) was added to each well, and the cells were allowed to stay under starvation condition for one day.

Then, each of the human anti-human TβRII monoclonal antibodies of the present invention or commercially available anti-human TβRII polyclonal antibody (R&D) (concentration: 50 µg/ml), was added to each well, and the plate was pre-incubated for two hours.

Then, human TGF-β1 (final concentration: 1 to 4 ng/ml; R&D) was added to the plate, and the cells were cultured for 65 to 72 hours. The culture supernatant was then recovered from each well.

The respective culture supernatants were assayed for the amount of fibronectin using Fibronectin EIA Kit (Takara Shuzo).

In addition, the amount of connective tissue growth factor (CTGF) in each culture supernatant was also determined by sandwich ELISA (Biochem. Biophys. Res. Commun., Vol. 251, p. 748-752, 1998; international publication WO 99-33878).

A positive control test was carried out by the same method as described above in the absence of any antibody. Further, a negative control test was carried out by the same method as described above in the absence of TGF-β1 and any antibody. The results are depicted in FIG. 12 and FIG. 13.

FIG. 4 also demonstrates the result obtained by this test (in multiple experiments) wherein the presence or absence of inhibitory activity of the human anti-human TβRII monoclonal antibodies of the present invention on TGF-β1-induced production enhancement of fibronectin and CTGF is simply represented with symbols.

The human anti-human TβRII monoclonal antibodies of the present invention were demonstrated to significantly inhibit the TGF-β-induced extracellular matrix production and cell growth factor production in human fibroblast-like cells.

EXAMPLE 11

The Therapeutic Effect of TGF-β Type II Receptor Inhibitor on Kidney Diseases According to the same method as described in a previous report, kidney diseases (symptoms of nephritis and kidney fibrosis, and so on) were induced in Wistar rats (female, 150 g (Charles River Laboratories Inc.); each group contains five or ten animals) by administering anti-Thy-1 monoclonal antibody to the rats at a dose of 500 μg/animal by intravenous injection (Nephron, Vol. 78, p. 453-463, 1998; Kidney Blood Press Res., Vol. 22, p. 5-12, 1999).

On the same day (0 day) and four days after the injection of the anti-Thy-1 antibody, the above-prepared human anti-human TGF-β type II receptor monoclonal antibody (Clone: TRC175) was intraperitoneally administered at a dose of 10 mg/kg.

Physiological saline was administered to the negative control group according to the same method as described above. Further, normal rats were used for control.

The therapeutic effect of the human anti-human TGF-β type II receptor monoclonal antibody on the kidney disease (inhibition of impairing kidney function) was analyzed by measuring the amounts of protein excreted in urine (on the seventh day) and serum creatinine levels (on the seventh day) according to conventional methods.

Further, seven days after the administration of the anti-Thy-1 antibody, the amounts of, the extracellular matrix, fibronectin and type I collagen, which increase depending on the progress of the symptoms of the kidney diseases, were determined by immuno-staining of frozen tissue section samples collected from kidneys of the subject animals by a conventional method.

The quantities of extracellular matrix were determined as scores based on the degrees of stain, as indicated below.

Score 0: No detectable stain on the sample of glomerulus.

Score 1: Less than one third of the sample of glomerulus was stained.

Score 2: Less than two third of the sample of glomerulus was stained.

Score 3: Two third or more of the sample of glomerulus was stained.

The result is depicted in FIGS. 14 to 17.

The increase in the amount of protein excreted in urine was significantly inhibited in the group subjected to the administration of the anti-TGF-β type II receptor antibody as compared with the negative control group. Further, the increase in the serum creatinine level was also significantly inhibited in the group subjected to the administration of the anti-TGF-β type II receptor antibody as compared with the negative control group, and the level was comparable to that of normal rats.

Furthermore, the production of extracellular matrix in the kidney glomerulus was significantly inhibited in the group subjected to the administration of the anti-TGF-β type II receptor antibody as compared with the negative control group. This indicates that fibrosis of kidney tissue was inhibited.

EXAMPLE 12

Determination of the Nucleotide Sequences and Amino Acid Sequences of the Human Anti-Human TβRII Monoclonal Antibodies The cDNA sequence encoding the heavy chain variable region, and the cDNA sequence encoding the light chain variable region and constant region of the various human monoclonal antibodies against human TGFβRII prepared in the above-mentioned Examples were determined as described below. The structural features of the genes were also analyzed.

The hybridomas (Clone: TR4C175, TR4D204, TR4D455, and TR4D465; about $1 \times 10^6$ cells each) prepared in the above Example, each of which produce the human monoclonal antibodies against human TGFβRII, were cultured, and then centrifuged. The precipitate were collected and stored at −80° C. until poly($A^+$) RNAs, were extracted from the cells as described hereinafter.

Extraction and purification of poly($A^+$) RNAs from respective hybridomas were carried out using commercially available poly($A^+$) RNAs quick kit (Amersham-Pharmacia) according to following method. Each frozen cells described above were dissolved in a cell lysis buffer, and solubilized by destruction with a syringe. Oligo(dT) resin was added to the solubilized material, and the mixture was gently agitated for about three minutes. Then, the oligo (dT) resin was washed, and poly ($A^+$) RNAs was eluted with an elution buffer. The eluted poly($A^+$) RNAs was ethanol-precipitated, and then dissolved in 20 μl of Tris-EDTA buffer. The concentration of the poly ($A^+$) RNAs so obtained was determined based on the absorbance at a wavelength of 260 nm.

The poly($A^+$) RNAs was converted to double-stranded cDNA using commercially available cDNA synthesis kit (GIBCO BRL) and the primer according to SEQ ID NO: 19 by the reverse transcriptase method. Specifically, first strand cDNA and second strand cDNA were successively synthesized using the poly($A^+$) RNAs (1 to 5 μg) purified from each hybridoma as a template. The cDNA was extracted once with phenol/chloroform/isoamyl alcohol and then once with chloroform. Then, the cDNA was ethanol-precipitated, and ligated to an adaptor DNA (SEQ ID NO: 20 and SEQ ID NO: 21) with commercially available DNA ligase (TOYOBO). Further, the DNA reactant was extracted once with phenol/chloroform/isoamyl alcohol and then once with chloroform.

Then, the DNA reactant was ethanol-precipitated, and digested with commercially available restriction enzyme NotI (TOYOBO). The 5' end of the DNA was phosphorylated with commercially available ATP solution (GIBCO BRL) and nucleotide kinase (TOYOBO). The resulting DNA reactant was then fractionated by polyacrylamide gel-electrophoresis, and DNA ranging from about 500 bp to 2000 bp was recovered. Each of the recovered DNA was ligated to commercially available lambda phage vector λEXcell (Amersham Pharmacia) using commercially available DNA ligase (TOYOBO). Then, each DNA reactant was packaged into lambda phage particles using commercially available lambda phage packaging kit Gigapack III Gold (STRATAGENE). cDNA libraries were constructed from the phage using *E. coli* NM522, attached to the vector λEXcell, as the host.

The respective cDNA libraries were screened using synthetic oligo DNA as probes by a conventional method. cDNAs encoding the antibody heavy chain and light chain were thus prepared. The probe for the antibody heavy chain was the synthetic oligo DNA of SEQ ID NO: 22. The probe for the antibody light chain was the synthetic oligo DNA of SEQ ID NO: 23.

The nucleotide sequences of the respective cDNA so obtained were determined with commercially available Dye Terminator Cycle Sequencing FS kit (PE-Applied Biosystems) on PRISM377 DNA Sequencer (PE-Applied Biosystems).

The sequencing primers used to determine these sequences were commercially available M13-20 primer (STRATAGENE) and M13 Reverse primer (STRATAGENE). Further, the sequencing primer of SEQ ID NO: 24, which corresponds to the sequence of the antibody heavy chain constant region, was used to determine the sequence of the antibody heavy chain; the sequencing primer of SEQ ID NO: 25, which corresponds to the sequence of the antibody light chain constant region, was used to determine the sequence of the antibody light chain.

The sequence listing indicated below shows the cDNA sequences encoding the heavy chain variable regions and cDNA sequence encoding the light chain variable regions of the human monoclonal antibodies against human TGFβRII produced by the above-mentioned hybridomas, and the amino acid sequences deduced from the respective cDNA sequences.

<Clone TR4C175>

(Variable Region of Heavy Chain)

DNA sequence: SEQ ID NO: 3 (signal sequence: nucleotide number 1 to 57; V region: nucleotide number 58 to 352)

Amino acid sequence: SEQ ID NO: 4 (signal sequence: amino acid number 0.1 to 19; variable region: including amino acid number 21 to 117)

(Variable Region of Light Chain)

DNA sequence: SEQ ID NO: 11 (signal sequence: nucleotide number 1 to 66; V region: nucleotide number 67 to 352)

Amino acid sequence: SEQ ID NO: 12 (signal sequence: amino acid number 1 to 22; variable region: including amino acid number 23 to 117)

<Clone TR4D204>

(Variable Region of Heavy Chain)

DNA sequence: SEQ ID NO: 5 (signal sequence: nucleotide number 1 to 3; V region: nucleotide number 4 to 295)

Amino acid sequence: SEQ ID NO: 6 (signal sequence: amino acid number 1; variable region: including amino acid number 2 to 98)

(Variable Region of Light Chain)

DNA sequence: SEQ ID NO: 13 (signal sequence: nucleotide number 1 to 57; V region: nucleotide number 58 to 348)

Amino acid sequence: SEQ ID NO: 14 (signal sequence: amino acid number 1 to 19; variable region: including amino acid number 21 to 116)

<Clone TR4D455>

(Variable Region of Heavy Chain)

DNA sequence: SEQ ID NO: 7 (signal sequence: nucleotide number 1 to 57; V region: nucleotide number 58 to 350)

Amino acid sequence: SEQ ID NO: 8 (signal sequence: amino acid number 1 to 19; variable region: including amino acid number 21 to 116)

(Variable Region of Light Chain)

DNA sequence: SEQ ID NO: 15 (signal sequence: nucleotide number 1 to 60; V region: nucleotide number 61 to 362)

Amino acid sequence: SEQ ID NO: 16 (signal sequence: amino acid number 1 to 20; variable region: including amino acid number 22 to 120)

<Clone TR4D465>

(Variable Region of Heavy Chain)

DNA sequence: SEQ ID NO: 9 (signal sequence: nucleotide number 1 to 57; V region: nucleotide number 58 to 353)

Amino acid sequence: SEQ ID NO: 10 (signal sequence: amino acid number 1 to 19; variable region: including amino acid number 21 to 117)

(Variable Region of Light Chain)

DNA sequence: SEQ ID NO: 17 (signal sequence: including nucleotide number 1 to 51; V region: nucleotide number 52 to 340)

Amino acid sequence: SEQ ID NO: 18 (signal sequence: including amino acid number 1 to 17; variable region: including amino acid number 18 to 113)

Based on the determined DNA sequences, the library V BASE Sequence, which contains the sequences of the genes of human immunoglobulin variable regions, produced by Tomlinson et al. (Immunol. Today, Vol. 16, No. 5, p. 237-242, 1995) was searched using analysis software for gene sequence.

The result demonstrated that the respective genes for the V region of the heavy chains and light chains of the above-mentioned human monoclonal antibodies consisted of the following segments.

<Heavy Chain V Region Gene>

| | |
|---|---|
| Clone TR4C175: | 3-21 (DP-77) |
| Clone TR4D204: | 3-07 (DP-54) |
| Clone TR4D455: | 5-51 (DP-73) |
| Clone TR4D465: | 3-07 (DP-54) |

<Light Chain V Region Gene>

| | |
|---|---|
| Clone TR4C175: | A30 |
| Clone TR4D204: | B-3 (DPK-24) |
| Clone TR4D455: | A19 (DPK-15) |
| Clone TR4D465: | A18 (DPK-28) |

EXAMPLE 13

Determination of the Affinity and Neutralizing Activity of the Human Anti-Human TGF-β Type II Receptor Monoclonal Antibodies to the Antigen (Human TGF-β type II Receptor)

The association rate constant (ka), dissociation rate constant (kd) and dissociation constant (Kd) of the binding between the various human anti-human TGF-β type II receptor monoclonal antibodies prepared as described above and human TGF-β type II receptor were determined with commercially available assay kit Biacore X (Amersham-Pharmacia).

The procedures except for the immobilization of the antigen (purified human soluble TβRII) on a sensor chip described below were carried out according to the instruction and experimental protocol attached to the commercially available assay kit Biacore X (Amersham-Pharmacia).

HBS buffer (containing 0.01 M HEPES, 0.15 M NaCl, 3 mM EDTA, and 0-0.005% Detergent P20, pH 7.0) was injected through a flow cell-1 attached to the kit at a flow rate of 5 μl/min. Then, 35 μl of a solution consisting of 0.005 M NHS (N-hydroxysuccinimide) and 0.2 M EDC (N-ethyl-N'-(dimethylaminopropyl)carbodiimide) was injected to activate the carboxyl groups of the CM coated on the sensor chip.

Then, 70 μl of purified soluble human TβRII (30 μg/ml; dissolved in 10 mM sodium acetate buffer (pH 5.0)) prepared in Example 2 was injected over the chip to be immobilized on the sensor chip.

Then, non-reacted activated carboxyl groups were blocked by adding 35 μl of 1 M ethanol amine hydrochloride. The amount of human soluble TβRII immobilized by this procedure was 5234 RU (resonance unit). RU represents mass per unit area: 1 RU=1 pg/mm$^2$.

Capping of flow cell-2 as a reference was carried out by the same treatment as described above in the absence of the human soluble TβRII.

Phosphate buffer was injected to the flow cell (sensor chip) at a flow rate of 20 μl/minute, and each of the purified human anti-human TGF-β type II receptor monoclonal antibody prepared in the above Example (40 to 100 μg/ml, 60 μl) was added thereto.

The standard assay condition comprised the association phase for three minutes and dissociation phase for 200 seconds. A sensorgram was obtained by measuring the amounts of the bound antibody and the amount of antibody dissociated from the antigen over time.

Based on the sensorgram data so obtained, the association rate constant (ka), dissociation rate constant (kd), and dissociation constant (Kd; Kd=kd/ka) were computed using analysis software (BIAevaluation 3.0) attached to the kit. Respective values are listed below.

| <Clone name> | <ka(1/M.Sec)> | <kd[1/Sec]> | <Kd(M)> |
| --- | --- | --- | --- |
| TR4C175 | $3.0 \times 10^5$ | $1.4 \times 10^{-2}$ | $5.1 \times 10^{-8}$ |
| TR4D455 | $5.2 \times 10^4$ | $1.2 \times 10^{-4}$ | $3.4 \times 10^{-9}$ |
| TR4D204 | $7.4 \times 10^3$ | $5.5 \times 10^{-4}$ | $7.5 \times 10^{-8}$ |
| TR4D465 | $1.2 \times 10^4$ | $2.3 \times 10^{-4}$ | $2.0 \times 10^{-8}$ |
| TR2B 19 | $4.5 \times 10^5$ | $3.2 \times 10^{-3}$ | $1.0 \times 10^{-8}$ |
| TR2B 64 | $5.2 \times 10^5$ | $3.6 \times 10^{-2}$ | $8.6 \times 10^{-8}$ |
| TR2D245 | $2.2 \times 10^5$ | $2.3 \times 10^{-4}$ | $1.1 \times 10^{-9}$ |

This result demonstrated that all the human anti-human TGF-β type II receptor monoclonal antibodies exhibit a very high binding affinity and very high neutralizing activity to human TGF-β type II receptor.

INDUSTRIAL APPLICABILITY

As the monoclonal antibodies of the present invention are from human, they have no antigenicity to the human host, which is a major therapeutic problem (side effect) in medical treatment with antibody pharmaceuticals comprising antibodies derived from non-human mammals, such as mice. This means the antibodies of the present invention do not induce severe host immune rejection caused by HAMA (human anti-mouse antigenicity), and, therefore, dramatically elevates the value of the antibody as a pharmaceutical.

Further, a substance that binds to TGF-β type II receptor to suppress or inhibit the signal transduction into cells mediated by the receptor, which is represented by the human monoclonal antibodies of the present invention that binds to the human TGF-β type II receptor (other examples include chemically synthesized low-molecular-weight compounds and natural compounds isolated from animals, plants, bacteria, microorganisms, etc.), and also a pharmaceutical composition comprising the substance are useful as a pharmaceutical for treating or preventing various types of diseases caused by the action of TGF-β by suppressing or inhibiting the onset and/or progress of the diseases. Such diseases are exemplified by kidney diseases (kidney fibrosis, nephritis, renal failure, nephrosclerosis, etc.); lung diseases (e.g., pulmonary fibrosis, pneumonia, etc.); liver diseases (e.g., liver tissue fibrosis, cirrhosis, hepatitis, etc.); skin diseases (e.g., wound, scleroderma, psoriasis, keloid, etc.) arthritis (e.g., rheumatoid arthritis, osteoarthritis, etc.); vascular diseases (e.g., vascular restenosis, rheumatic vasculitis, etc.); tissue fibroses in various organs (including tissue fibrosis accompanied by various cancers); arteriosclerosis (including accompanying tissue fibrosis); and so on.

The invention claimed is:

1. A human monoclonal antibody or monoclonal antibody fragment that binds to a human TGF-β type II receptor, wherein a heavy chain variable region of the human monoclonal antibody or monoclonal antibody fragment is encoded by a V region DNA derived from a V gene segment selected from 3-07 (DP-54), 5-51 (DP-73) and 3-21 (DP-77) and wherein the human monoclonal antibody or monoclonal antibody fragment has one or more activities selected from:
 (a) suppression of human TGF-β1 stimulus-induced cell growth of human osteosarcoma cell line MG-63;
 (b) suppression of human TGF-β1 stimulus-induced suppression of cell growth of human lung cancer cell line A549; and
 (c) suppression of human TGF-β1 stimulus-induced production of a fibronectin or connective tissue growth factor by human osteosarcoma cell line MG-63.

2. A method of inhibiting signal transduction into a cell induced by binding of a human TGF-β to a human TGF-β type II receptor of the cell, comprising providing a human monoclonal antibody or monoclonal antibody fragment according to claim 1 to the cell and allowing the human monoclonal antibody or monoclonal antibody fragment to bind to the human TGF-β type II receptor of the cell, to thereby inhibit the signal transduction into the cell.

3. The method of claim 2, wherein the human monoclonal antibody or monoclonal antibody fragment has variable region amino acid sequences selected from:
 (a) heavy chain variable region having an amino acid sequence from residues 21 to 117 of SEQ ID NO: 4 and light chain variable region having an amino acid sequence from residues 23 to 117 of SEQ ID NO: 12;
 (b) heavy chain variable region having an amino acid sequence from residues 2 to 98 of SEQ ID NO: 6 and light chain variable region having an amino acid sequence from residues 21 to 116 of SEQ ID NO: 14;
 (c) heavy chain variable region having an amino acid sequence from residues 21 to 116 of SEQ ID NO: 8 and light chain variable region having an amino acid sequence from residues 22 to 120 of SEQ ID NO: 16; and
 (d) heavy chain variable region having an amino acid sequence from residues 21 to 117 of SEQ ID NO: 10 and light chain variable region having an amino acid sequence from residues 18 to 113 of SEQ ID NO: 18.

4. The method of claim 2, wherein a light chain variable region of the human monoclonal antibody or monoclonal antibody fragment is encoded by a V region DNA derived from a V gene segment selected from A30, A19 (DPK-15), B-3 (DPK-24) and A-18 (DPK-28).

5. An isolated cell producing the human monoclonal antibody or monoclonal antibody fragment according to claim 1.

6. The isolated cell according to claim 5, wherein the cell is a fused cell produced by fusing a B cell from a mammal that produces the human monoclonal antibody or monoclonal antibody fragment with a myeloma cell derived from a mammal.

7. The isolated cell according to claim 5, wherein the cell is a recombinant cell, which has been transformed by either or both of DNA encoding the heavy chain and DNA encoding the light chain of the human monoclonal antibody or monoclonal antibody fragment.

8. The isolated cell according to claim 5, wherein a light chain variable region of the human monoclonal antibody or monoclonal antibody fragment is encoded by a V region DNA derived from a V gene segment selected from A30, A19 (DPK-15), B-3 (DPK-24) and A-18 (DPK-28).

9. The isolated cell according to claim 5, wherein the human monoclonal antibody or monoclonal antibody fragment has variable region amino acid sequences selected from:
 (a) heavy chain variable region having an amino acid sequence from residues 21 to 117 of SEQ ID NO: 4 and light chain variable region having an amino acid sequence from residues 23 to 117 of SEQ ID NO: 12;
 (b) heavy chain variable region having an amino acid sequence from residues 2 to 98 of SEQ ID NO: 6 and light chain variable region having an amino acid sequence from residues 21 to 116 of SEQ ID NO: 14;
 (c) heavy chain variable region having an amino acid sequence from residues 21 to 116 of SEQ ID NO: 8 and light chain variable region having an amino acid sequence from residues 22 to 120 of SEQ ID NO: 16; and
 (d) heavy chain variable region having an amino acid sequence from residues 21 to 117 of SEQ ID NO: 10 and light chain variable region having an amino acid sequence from residues 18 to 113 of SEQ ID NO: 18.

10. A pharmaceutical composition comprising the human monoclonal antibody or monoclonal antibody fragment according to claim 1, and a pharmaceutically acceptable carrier.

11. The pharmaceutical composition of claim 10, wherein a wherein a light chain variable region of the human monoclonal antibody or monoclonal antibody fragment is encoded by a V region DNA derived from a V gene segment selected from A30, A19 (DPK-15), B-3 (DPK-24) and A-18 (DPK-28).

12. The pharmaceutical composition of claim 10, wherein the human monoclonal antibody or monoclonal antibody fragment has variable region amino acid sequences selected from:
(a) heavy chain variable region having an amino acid sequence from residues 21 to 117 of SEQ ID NO: 4 and light chain variable region having an amino acid sequence from residues 23 to 117 of SEQ ID NO: 12;
(b) heavy chain variable region having an amino acid sequence from residues 2 to 98 of SEQ ID NO: 6 and light chain variable region having an amino acid sequence from residues 21 to 116 of SEQ ID NO: 14;
(c) heavy chain variable region having an amino acid sequence from residues 21 to 116 of SEQ ID NO: 8 and light chain variable region having an amino acid sequence from residues 22 to 120 of SEQ ID NO: 16; and
(d) heavy chain variable region having an amino acid sequence from residues 21 to 117 of SEQ ID NO: 10 and light chain variable region having an amino acid sequence from residues 18 to 113 of SEQ ID NO: 18.

13. A method of suppressing tissue fibrosis in a subject mediated by binding of a human TGF-β to a human TGF-β type II receptor of a cell of the subject, comprising administering a human monoclonal antibody or monoclonal antibody fragment according to claim 1 to the subject and allowing the human monoclonal antibody or monoclonal antibody fragment to bind to the TGF-β type II receptor of the cell of said subject, to thereby inhibit the signal transduction into the cells and thereby suppress the tissue fibrosis.

14. The method of suppressing tissue fibrosis in a subject according to claim 13, wherein the tissue fibrosis is fibrosis in the lung, liver, kidney, or skin.

15. The method of suppressing tissue fibrosis in a subject according to claim 14, wherein the tissue fibrosis is fibrosis in the kidney.

16. The method of claim 13, wherein a light chain variable region of the human monoclonal antibody or monoclonal antibody fragment is encoded by a V region DNA derived from a V gene segment selected from A30, A19 (DPK-15), B-3 (DPK-24) and A-18 (DPK-28).

17. The method of claim 13, wherein the human monoclonal antibody or monoclonal antibody fragment has variable region amino acid sequences selected from:
(a) heavy chain variable region having an amino acid sequence from residues 21 to 117 of SEQ ID NO: 4 and light chain variable region having an amino acid sequence from residues 23 to 117 of SEQ ID NO: 12;
(b) heavy chain variable region having an amino acid sequence from residues 2 to 98 of SEQ ID NO: 6 and light chain variable region having an amino acid sequence from residues 21 to 116 of SEQ ID NO: 14;
(c) heavy chain variable region having an amino acid sequence from residues 21 to 116 of SEQ ID NO: 8 and light chain variable region having an amino acid sequence from residues 22 to 120 of SEQ ID NO: 16; and
(d) heavy chain variable region having an amino acid sequence from residues 21 to 117 of SEQ ID NO: 10 and light chain variable region having an amino acid sequence from residues 18 to 113 of SEQ ID NO: 18.

18. A human monoclonal antibody or monoclonal antibody fragment that binds to a human TGF-β type II receptor, wherein a light chain variable region of the human monoclonal antibody or monoclonal antibody fragment is encoded by a V region DNA derived from a V gene segment selected from A30, A19 (DPK-15), B-3 (DPK-24) and A-18 (DPK-28) and wherein the human monoclonal antibody or monoclonal antibody fragment has one or more activities selected from:
(a) suppression of human TGF-β1 stimulus-induced cell growth of human osteosarcoma cell line MG-63;
(b) suppression of human TGF-β1 stimulus-induced suppression of cell growth of human lung cancer cell line A549; and
(c) suppression of human TGF-β1 stimulus-induced production of a fibronectin or connective tissue growth factor by human osteosarcoma cell line MG-63.

19. The human monoclonal antibody or monoclonal antibody fragment according to claim 1 wherein a light chain variable region of the human monoclonal antibody or monoclonal antibody fragment is encoded by a V region DNA derived from a V gene segment selected from A30, A19 (DPK-15), B-3 (DPK-24) and A-18 (DPK-28).

20. The human monoclonal antibody or monoclonal antibody fragment according to any one of claims 18-19, having variable region amino acid sequences selected from:
(a) heavy chain variable region having an amino acid sequence from residues 21 to 117 of SEQ ID NO: 4 and light chain variable region having an amino acid sequence from residues 23 to 117 of SEQ ID NO: 12;
(b) heavy chain variable region having an amino acid sequence from residues 2 to 98 of SEQ ID NO: 6 and light chain variable region having an amino acid sequence from residues 21 to 116 of SEQ ID NO: 14;
(c) heavy chain variable region having an amino acid sequence from residues 21 to 116 of SEQ ID NO: 8 and light chain variable region having an amino acid sequence from residues 22 to 120 of SEQ ID NO: 16; and
(d) heavy chain variable region having an amino acid sequence from residues 21 to 117 of SEQ ID NO: 10 and light chain variable region having an amino acid sequence from residues 18 to 113 of SEQ ID NO: 18.

21. A method of inhibiting signal transduction into a cell induced by binding of a human TGF-β to a human TGF-β type II receptor of the cell, comprising providing a human monoclonal antibody or monoclonal antibody fragment according to claim 18 to the cell and allowing the human monoclonal antibody or monoclonal antibody fragment to bind to the human TGF-β type II receptor of the cell, to thereby inhibit the signal transduction into the cell.

22. The method of claim 21, wherein a heavy chain variable region of the human monoclonal antibody or monoclonal antibody fragment is encoded by a V region DNA derived from a V gene segment selected from 3-07 (DP-54), 5-51 (DP-73) and 3-21 (DP-77).

23. An isolated cell producing the human monoclonal antibody or monoclonal antibody fragment according to claim 18.

24. The isolated cell according to claim 23, wherein the cell is a fused cell produced by fusing a B cell from a mammal that produces the human monoclonal antibody or monoclonal antibody fragment with a myeloma cell derived from a mammal.

25. The isolated cell according to claim 23, wherein the cell is a recombinant cell, which has been transformed by either or both of DNA encoding the heavy chain and DNA encoding the light chain of the human monoclonal antibody or monoclonal antibody fragment.

26. A pharmaceutical composition comprising the human monoclonal antibody or monoclonal antibody fragment according to claim 18, and a pharmaceutically acceptable carrier.

27. A method of suppressing tissue fibrosis in a subject mediated by binding of a human TGF-β to a human TGF-β type II receptor of a cell of the subject, comprising administering a human monoclonal antibody or monoclonal antibody fragment according to claim 18 to the subject and allowing the human monoclonal antibody or monoclonal antibody fragment to bind to the TGF-β type II receptor of the cell of said subject, to thereby inhibit the signal transduction into the cells and thereby suppress the tissue fibrosis.

28. The method of suppressing tissue fibrosis in a subject according to claim 27, wherein the tissue fibrosis is fibrosis in the lung, liver, kidney, or skin.

29. The method of suppressing tissue fibrosis in a subject according to claim 28, wherein the tissue fibrosis is fibrosis in the kidney.

\* \* \* \* \*

UNITED STATES PATENT AND TRADEMARK OFFICE
CERTIFICATE OF CORRECTION

PATENT NO.       : 7,579,186 B1
APPLICATION NO. : 10/130034
DATED            : August 25, 2009
INVENTOR(S)      : Sakamoto et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 414 days.

Signed and Sealed this

Fourteenth Day of December, 2010

David J. Kappos
*Director of the United States Patent and Trademark Office*